US008030328B2

(12) United States Patent
Stappenbeck et al.

(10) Patent No.: US 8,030,328 B2
(45) Date of Patent: Oct. 4, 2011

(54) IMIDAZOLONE PHENYLALANINE DERIVATIVES

(75) Inventors: Frank Stappenbeck, Seattle, WA (US); Andrei Konradi, Burlingame, CA (US); Jacek Jagodzinski, Redwood City, CA (US); Christopher M. Semko, Fremont, CA (US); Ying-zi Xu, Palo Alto, CA (US); Jenifer L. Smith, South San Francisco, CA (US); Kassandra Rossiter, San Jose, CA (US)

(73) Assignee: Elan Pharmaceuticals, Inc., So. San Francisco, CA (US)

( * ) Notice: Subject to any disclaimer, the term of this patent is extended or adjusted under 35 U.S.C. 154(b) by 941 days.

(21) Appl. No.: 11/438,659

(22) Filed: May 22, 2006

(65) Prior Publication Data
US 2007/0037804 A1 Feb. 15, 2007

Related U.S. Application Data

(60) Provisional application No. 60/683,509, filed on May 20, 2005.

(51) Int. Cl.
A61K 31/4166 (2006.01)
A61K 31/437 (2006.01)
C07D 235/26 (2006.01)
C07D 471/04 (2006.01)
(52) U.S. Cl. ...... 514/303; 514/387; 546/118; 548/302.7
(58) Field of Classification Search ............... 548/302.7; 546/118
See application file for complete search history.

(56) References Cited

U.S. PATENT DOCUMENTS

| | | | |
|---|---|---|---|
| 6,479,492 B1 | 11/2002 | Konradi et al. | |
| 6,489,300 B1 * | 12/2002 | Thorsett et al. | 514/19 |
| 6,492,372 B1 | 12/2002 | Konradi et al. | |
| 6,525,026 B2 | 2/2003 | Thorsett et al. | |
| 6,900,179 B2 | 5/2005 | Thorsett et al. | |
| 6,903,088 B2 | 6/2005 | Konradi et al. | |
| 6,911,439 B2 | 6/2005 | Konradi et al. | |
| 6,939,855 B2 | 9/2005 | Yednock et al. | |
| 7,005,433 B2 | 2/2006 | Konradi et al. | |
| 7,026,328 B2 | 4/2006 | Konradi et al. | |
| 7,049,306 B2 | 5/2006 | Konradi et al. | |
| 7,135,477 B2 | 11/2006 | Konradi et al. | |
| 7,205,310 B2 | 4/2007 | Konradi et al. | |
| 7,378,529 B2 | 5/2008 | Konradi et al. | |
| 7,427,628 B2 | 9/2008 | Konradi et al. | |
| 2005/0261293 A1 | 11/2005 | Konradi et al. | |
| 2006/0013799 A1* | 1/2006 | Konradi et al. | 424/78.27 |
| 2007/0037804 A1 | 2/2007 | Stappenbeck et al. | |
| 2007/0099921 A1 | 5/2007 | Konradi et al. | |

FOREIGN PATENT DOCUMENTS

| | | |
|---|---|---|
| EP | 0 503 548 | 9/1992 |
| WO | WO 99/06390 | 2/1999 |
| WO | WO 99/06391 | 2/1999 |
| WO | WO 00/43369 | 7/2000 |
| WO | WO 00/43372 | 7/2000 |
| WO | WO 01/54690 | 8/2001 |
| WO | WO 02/08202 | 1/2002 |
| WO | WO 03/084984 | 10/2003 |
| WO | WO 03/099809 | 12/2003 |
| WO | WO 2004/066931 | 8/2004 |
| WO | WO 2005/000246 | 1/2005 |
| WO | WO 2005/070921 | 8/2005 |
| WO | WO 2005/111020 | 11/2005 |
| WO | WO 2006/010054 | 1/2006 |
| WO | WO 2006/127584 | 11/2006 |

OTHER PUBLICATIONS

Gutteridge, et al. Bioorganic & Medicinal Chemistry Letters 13 (2003) 885-890.*
Cecil Textbook of Medicine, 20th edition (1996), vol. 2, pp. 2050-2057.*
Cecil Textbook of Medicine, 20th edition (1996), vol. 2, pp. 1992-1996.*
FDA mulls drug to slow late-stage Alzheimer's [online], [retrieved on Sep. 23, 2003]. Retrieved from the Internet, URL; http://www.cnn.com/2003/HEALTH/conditions/O9/24/alzheimers.drug.ap/indexhtml>.*
Dementia [online], [retrieved on May 24, 2007]. Retrieved from the Internet, URL; http://en.wikipedia.org/wiki/Dementia>.*
Huryn D. M., et al. "Synthesis, characterization and evaluation of pro-drugs of VLA-4 antagonists" *Bioorganic and Medicinal Chemistry Letters* Apr. 2004: 1651-1654 (2004). Jones D. S. et al. "Multivalent poly(ethylene glycol)-containing conjugates for in vivo antibody suppression" *Bioconjugate Chemistry* 14(6): 1067-1076 (2003).
Chen L. L. et al. "Evidence that ligand and metal ion binding to integrin α4β1 are regulated through a coupled equilibrium" *Journal of Biological Chemistry* 276: 36520-36529 (2001).
Pepinsky R. B. et al. "Design, synthesis and analysis of a polyethylene glycol-modified (PEGylated) small molecule inhibitor of integrin α4β1 with improved pharmaceutical properties" *Journal of Pharmacology and Experimental Therapeutics* 312(2): 742-750 (2005).
Haag R. et al. "Polymer Therapeutics: Concepts and Applications" *Angewandte Chemie International Edition* 45(8): 1198-1215 (2006).

* cited by examiner

*Primary Examiner* — Shawquia Young
(74) *Attorney, Agent, or Firm* — McDonnell Boehnen Hulbert & Berghoff LLP

(57) ABSTRACT

Disclosed are compounds of the formula:

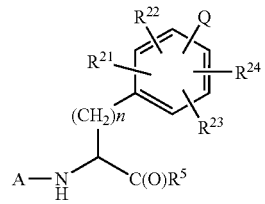

and the pharmaceutically acceptable salts thereof wherein the variables A, n, $R^5$, $R^{21}$-$R^{24}$ and Q are defined herein. These compounds bind VLA-4. Certain of these compound also inhibit leukocyte adhesion and, in particular, leukocyte adhesion mediated by VLA-4. Such compounds are useful in the treatment of inflammatory diseases in a mammalian patient, e.g., human, such as asthma, Alzheimer's disease, atherosclerosis, AIDS dementia, diabetes, inflammatory bowel disease, rheumatoid arthritis, tissue transplantation, tumor metastasis and myocardial ischemia. The compounds can also be administered for the treatment of inflammatory brain diseases such as multiple sclerosis.

27 Claims, No Drawings

IMIDAZOLONE PHENYLALANINE DERIVATIVES

CROSS-REFERENCE TO RELATED APPLICATIONS

This application claims priority to U.S. provisional application No. 60/683,509, filed May 20, 2005.

BACKGROUND OF THE INVENTION

1. Field of the Invention

This invention relates to imidazolone phenylalanine derivatives, and in particular, to such compounds that inhibit leukocyte adhesion and, in particular, leukocyte adhesion mediated by alpha 4 integrins.

2. Description of the Related Art

The physical interaction of inflammatory leukocytes with each other and other cells of the body plays an important role in regulating immune and inflammatory responses [Springer, T. A. Nature, 346, 425, (1990); Springer, T. A. Cell 76, 301, (1994)]. Many of these interactions are mediated by specific cell surface molecules collectively referred to as cell adhesion molecules. These adhesion molecules have been sub-divided into different groups on the basis of their structure. One family of adhesion molecules which is believed to play an important role in regulating immune and inflammatory responses is the integrin family. This family of cell surface glycoproteins has a typical non-covalently linked heterodimer structure.

The particular integrin subgroup of interest herein involves the alpha 4 ($\alpha$4) chain, which can pair with two different beta chains beta1 ($\beta$1) and beta7 ($\beta$7) [Sonnenberg, A. ibid]. The $\alpha$4$\beta$1 pairing occurs on many circulating leukocytes (for example lymphocytes, monocytes and eosinophils) although it is absent or only present at low levels on circulating neutrophils. VLA-4 (Very Late Antigen –4, also referred to as $\alpha_4\beta_1$ integrin and as CD49d/CD29), first identified by Hemler and Takada[1] is a member of the $\beta$1 integrin family of cell surface receptors. VLA-4 consists of an $\alpha$4 chain and a $\beta$1 chain. There are at least nine $\beta$1 integrins, all sharing the same $\beta$1 chain and each having a distinct a chain. These nine receptors all bind a different complement of the various cell matrix molecules, such as fibronectin, laminin, and collagen. VLA-4, for example, binds to fibronectin. VLA-4 also binds non-matrix molecules that are expressed by endothelial and other cells.

VLA-4 ($\alpha$4$\beta$1 integrin) binds to an adhesion molecule called Vascular Cell Adhesion Molecule-1 (or VCAM-1) which is frequently up-regulated on endothelial cells at sites of inflammation [Osborne, L. Cell, 62, 3 (1990)]. VCAM-1 is a non-matrix molecule which is an expressed receptor that is believed to be responsible for trafficking leukocytes into the central nervous system (CNS). $\alpha$4$\beta$1 has also been shown to bind to at least three sites in the matrix molecule fibronectin [Humphries, M. J. et al. Ciba Foundation Symposium, 189, 177, (1995)]. Distinct epitopes of VLA-4 are responsible for the fibronectin and VCAM-1 binding activities and each has been demonstrated to be independently inhibited.[2] Based on data obtained with monoclonal antibodies in animal models it is believed that the interaction between $\alpha$4$\beta$1 and ligands on other cells and the extracellular matrix plays an important role in leukocyte migration and activation [Yednock, T. A. et al, Nature, 356, 63, (1992).

The integrin generated by the pairing of $\alpha$4 and $\beta$7 has been termed LPAM-1 [Holzmann, B and Weissman, I. EMBO J. 8, 1735, (1989)] and like $\alpha$4$\beta$1, can bind to VCAM-1 and fibronectin. In addition, $\alpha$4$\beta$7 binds to an adhesion molecule believed to be involved in the homing of leukocytes to mucosal tissue termed MAdCAM-1 [Berlin, C. et al. Cell, 74, 185, (1993)]. The interaction between $\alpha$4$\beta$7 and MAd-CAM-1 also be important at sites of inflammation outside of mucosal tissue [Yang, X-D. et al. PNAS, 91, 12604 (1994)].

Intercellular adhesion mediated by VLA-4 and other cell surface receptors is associated with a number of inflammatory responses. At the site of an injury or other inflammatory stimuli, activated vascular endothelial cells express molecules that are adhesive for leukocytes. The mechanics of leukocyte adhesion to endothelial cells involve, in part, the recognition and binding of cell surface receptors on leukocytes to the corresponding cell surface molecules on endothelial cells. Once bound, the leukocytes migrate across the blood vessel wall to enter the injured site and release chemical mediators to combat infection. For reviews of adhesion receptors of the immune system, see, for example, Springer[3] and Osborn[4].

Inflammatory brain disorders, such as multiple sclerosis (MS), meningitis, encephalitis, and a disease model called experimental autoimmune encephalomyelitis (EAE), are examples of central nervous system disorders in which the endothelium/leukocyte adhesion mechanism results in destruction to otherwise healthy brain tissue. Large numbers of leukocytes migrate across the blood brain barrier (BBB) in subjects with these inflammatory diseases. The leukocytes release toxic mediators that cause extensive cell damage and death resulting in impaired nerve conduction and paralysis. Similar occurrences in encephalitis and meningitis indicate that these diseases can be treated with suitable cell adhesion inhibitors.

In other organ systems, tissue damage also occurs via an adhesion mechanism resulting in migration or activation of leukocytes. For example, inflammatory bowel disease[15] (including ulcerative colitis and Crohn's disease), are at least partially caused by leukocyte trafficking across the intestinal endothelium via an $\alpha$4$\beta$7 interaction with MadCAM and possibly $\alpha$4$\beta$1 interaction with VCAM-1 expressed in this tissue as well. Asthma[6-8], rheumatoid arthritis[18-21] and tissue transplant rejection[22] are all thought to have components based in interaction of $\alpha$4$\beta$1 with VCAM-1 and/or fibronectin, probably both. it has been shown that the initial insult following myocardial (heart tissue) ischemia can be further complicated by leukocyte entry to the injured tissue causing still further injury (Vedder et al.[5]). Other inflammatory or medical conditions mediated by an adhesion molecule mechanism include, by way of example, Alzheimer's disease, atherosclerosis[9-10], AIDS dementia[11], diabetes[12-14] (including acute juvenile onset diabetes, tumor metastasis[23-28], stroke, and other cerebral traumas, nephritis, retinitis, atopic dermatitis, psoriasis, and acute leukocyte-mediated lung injury such as that which occurs in adult respiratory distress syndrome.

Two groups of VLA-4 antagonists showing promise as anti-inflammatory agents is the class of sulfonylated-Pro-Phe and pyrimidinyl-Phe compounds as set forth in, for example, U.S. Pat. Nos. 6,489,300 and 6,492,372 respectively.[31] These compounds are very potent antagonists of VLA-4/VCAM-1 binding.

SUMMARY OF THE INVENTION

This invention provides compounds which bind to VLA-4. This invention provides compounds exhibiting VLA-4 antagonistic properties. Such compounds can be used, for example, to assay for the presence of VLA-4 in a sample and in pharmaceutical-compositions to inhibit cellular adhesion mediated by VLA-4, for example, binding of VCAM-1 to VLA-4. Preferred compounds of this invention have a binding affinity to VLA-4 as expressed by an $IC_{50}$ of about 15 μM or less (as measured using the procedures described in Example A below).

In one aspect, the invention provides compounds of formula I:

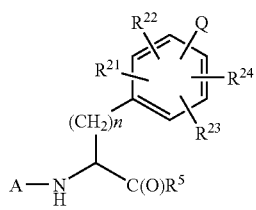

and pharmaceutically acceptable salts thereof, wherein

A is —H, optionally substituted aryl, optionally substituted heteroaryl or the group —C(X)D($R^3$)Z, wherein D is a carbon atom (when part of a substituted aryl or substituted heteroaryl), CH, N or O, with the proviso that if D is oxygen, then Z is not present;

Z is —H, —$NO_2$, haloalkyl or the group —N(Y$R^1$)$R^2$ where

Y is a covalent bond, —C(O)— or —$SO_2$—, $R^1$ is $R^{1'}$, N($R^{1'}$)$_2$, or —O$R^{1'}$, where each $R^{1'}$ is independently hydrogen, an optionally substituted straight or branched $C_1$-$C_6$alkyl, optionally substituted cycloalkyl, optionally substituted aryl, optionally substituted heterocyclic or an optionally substituted heteroaryl, wherein optional substitutions are halide, $C_1$-$C_6$alkyl, —O$C_1$-$C_6$alkyl, and $R^2$ is hydrogen or $R^{1'}$;

X is selected from the group consisting of oxygen, sulfur, CH$R^4$ and N$R^4$, wherein $R^4$ is —H, alkyl or substituted alkyl;

$R^3$ is hydrogen, alkyl, substituted alkyl, cycloalkyl, substituted cycloalkyl, aryl, substituted aryl, heteroaryl, substituted heteroaryl, heterocyclic, or substituted heterocyclic; or D, $R^3$ and Z together form a heterocyclic or a substituted heterocyclic group, wherein said group contains 1, 2, or 3 heteroatoms selected from O, N, and S; or X, D and $R^3$ together with the carbon atom carrying D and X form an optionally substituted carbocyclic or optionally substituted heterocyclic group, wherein said heterocyclic group contains 1, 2, or 3 heteroatoms selected from O, N, and S;

$R^3$ and $R^4$ together with the nitrogen atom bound to $R^4$ and the carbon atom bound to $R^3$ form a heterocyclic or a substituted heterocyclic group, wherein said group contains 1, 2, or 3 heteroatoms selected from O, N, and S;

$R^5$ is selected from the group consisting of amino, substituted amino, alkoxy, substituted alkoxy, cycloalkyloxy, substituted cycloalkyloxy, aryloxy and substituted aryloxy, and —OH;

n is 0 or an integer from 1 to 4;

Q is a group of the formula V

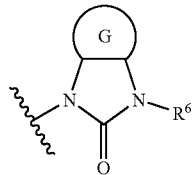

wherein G is an optionally substituted aryl or optionally substituted heteroaryl 5 or 6 membered ring containing 0 to 3 nitrogens; and $R^6$ is —H, alkyl, substituted alkyl, or —$CH_2$C(O)$R^7$ wherein $R^7$ is —OH, —O$R^8$, or —NH$R^8$ wherein $R^8$ is alkyl, substituted alkyl, aryl or substituted aryl;

$R^{21}$, $R^{22}$, $R^{23}$, and $R^{24}$ are independently selected from the group consisting of hydrogen, —$C_1$-$C_3$alkyl, —O$C_1$-$C_3$alkyl and halogen.

The invention also provides pharmaceutical compositions which comprise, for example, a pharmaceutically acceptable carrier and a compound of the invention or mixtures thereof.

The invention also provides methods for treating a disease mediated, at least in part, by VLA-4 in a patient, which method comprises administering a therapeutically effective amount of a compound of the invention, or a pharmaceutical composition comprising a pharmaceutically acceptable carrier and a compound of the invention or mixtures thereof.

The invention also includes the use of a compound of the invention, and pharmaceutically acceptable salts thereof, for the manufacture of a medicament for use in treating a disease mediated, at least in part, by VLA-4 in a patient.

The compounds and pharmaceutical compositions may be used to treat disease conditions mediated, at least in part, by VLA-4 or leukocyte adhesion. Such disease conditions include, by way of example, asthma, Alzheimer's disease, atherosclerosis, AIDS dementia, diabetes (including acute juvenile onset diabetes), inflammatory bowel disease (including ulcerative colitis and Crohn's disease), multiple sclerosis, rheumatoid arthritis, tissue transplantation, tumor metastasis, meningitis, encephalitis, stroke, and other cerebral traumas, nephritis, retinitis, Sjogren's disease, atopic dermatitis, psoriasis, myocardial ischemia and acute leukocyte-mediated lung injury such as that which occurs in adult respiratory distress syndrome.

Other disease conditions which may be treated using compounds and compositions of the present invention include, but are not limited to, inflammatory conditions such as erythema nodosum, allergic conjunctivitis, optic neuritis, uveitis, allergic rhinitis, ankylosing spondylitis, psoriatic arthritis, vasculitis, Reiter's syndrome, systemic lupus erythematosus, progressive systemic sclerosis, polymyositis, dermatomyositis, Wegner's granulomatosis, aortitis, sarcoidosis, lymphocytopenia, temporal arteritis, pericarditis, myocarditis, congestive heart failure, polyarteritis nodosa, hypersensitivity syndromes, allergy, hypereosinophilic syndromes, Churg-Strauss syndrome, chronic obstructive pulmonary disease, hypersensitivity pneumonitis, chronic active hepatitis, interstitial cystitis, autoimmune endocrine failure, primary biliary cirrhosis, autoimmune aplastic anemia, chronic persistent hepatitis and thyroiditis.

Preferably, the compounds and pharmaceutically compositions of this invention are used in methods for treating asthma, rheumatoid arthritis and multiple sclerosis. As to this latter disease, the compounds of this invention not only provide an anti-inflammatory effect when administered in vivo but further find use in treating conditions and diseases associated with demyelination.

The invention also provides methods of preparing the compounds of the invention and the intermediates used in those methods.

DETAILED DESCRIPTION OF THE INVENTION

As noted above, this invention provides compounds of formula I. Compounds of Formula I inhibit leukocyte adhesion and, in particular, leukocyte adhesion mediated, at least in part, by VLA-4.

Preferred are compounds of formula I wherein

A is H, optionally substituted alkyl, optionally substituted cycloalkyl, optionally substituted aryl, optionally substituted heteroaryl or optionally substituted acyl;

n is an integer from 0-3;

$R^{21}$, $R^{22}$, $R^{23}$, and $R^{24}$ are independently selected from the group consisting of hydrogen, —$C_1$-$C_3$alkyl, —$OC_1$-$C_3$alkyl and halogen; and Q is a group of the formula V,

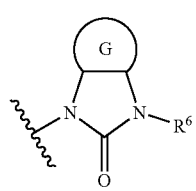

G is an optionally substituted aryl or optionally substituted heteroaryl 5 or 6 membered ring containing 0 to 3 nitrogens; and $R^6$ is —H, alkyl, substituted alkyl, —$CH_2C(O)R^7$ wherein $R^7$ is —OH, —$OR^8$, —$NHR^8$ wherein $R^8$ is alkyl, substituted alkyl, aryl or substituted aryl.

Other preferred compounds of formula I include compounds where A is selected from the group:

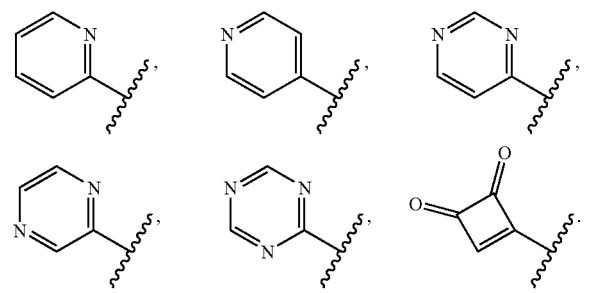

Other preferred compounds of formula I include compounds where Q is selected from the group:

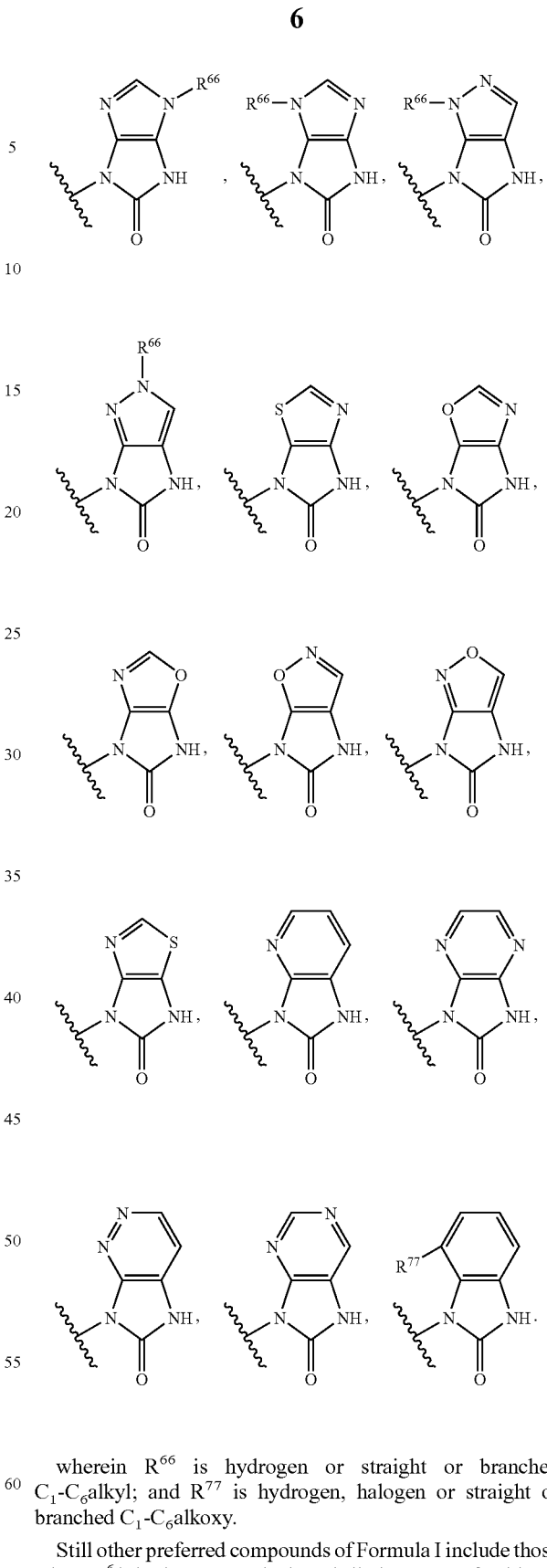

wherein $R^{66}$ is hydrogen or straight or branched $C_1$-$C_6$alkyl; and $R^{77}$ is hydrogen, halogen or straight or branched $C_1$-$C_6$alkoxy.

Still other preferred compounds of Formula I include those where $R^6$ is hydrogen or substituted alkyl. More preferably $R_6$ is hydrogen or alkyl substituted with amino, aminocarbonyl, $C_1$-$C_4$ alkoxy($C_1$-$C_4$)alkylaminocarbonyl, hydroxy($C_1$-$C_4$) alkylaminocarbonyl, or aminoalkoxyalkoxyalkyl.

Still other preferred compounds of formula I include compounds of formulas Ia and Ib:

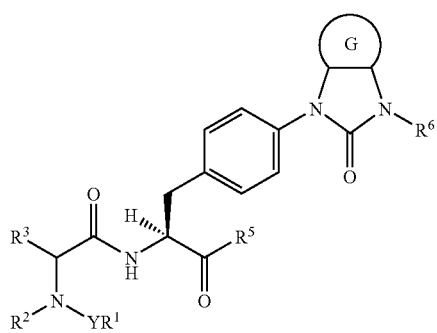

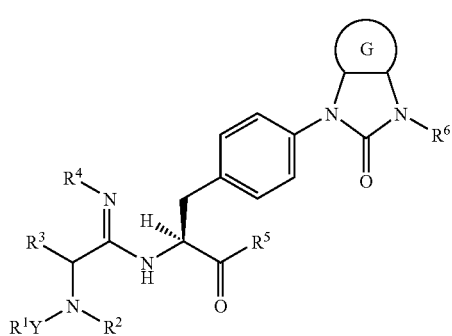

where in formula Ia, $R^2$ and $R^3$ together with the nitrogen atom bound to $R^2$ and the carbon atom bound to $R^3$ form a heterocyclic or a substituted heterocyclic group, and said cyclic group contains 1, 2, or 3 heteroatoms selected from O, N, and S; and in formula Ib, $R^3$ and $R^4$ together with the nitrogen atom bound to $R^4$ and the carbon atom bound to $R^3$ form a heterocyclic or a substituted heterocyclic group, and said cyclic group contains 1, 2, or 3 heteroatoms selected from O, N, and S;

and further wherein formula Ia and formula Ib are optionally substituted, on any ring atom or position capable of substitution, with 1-5, preferably 1-3 substituents selected from the group consisting of alkyl, substituted alkyl, alkoxy, substituted alkoxy, acyl, acylamino, thiocarbonylamino, acyloxy, amino, substituted amino, amidino, alkyl amidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, cyano, halogen, hydroxyl, nitro, oxo, carboxyl, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkyloxy, substituted cycloalkyloxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where each R is independently hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, —N[S(O)—R']$_2$ and —N[S(O)$_2$—NR']$_2$ where each R' is independently selected from the group consisting of alkyl, substituted alkyl, aryl, substituted aryl, heteroaryl, substituted heteroaryl, heterocyclic and substituted heterocyclic.

Preferred compounds of formula I include compounds of formula II

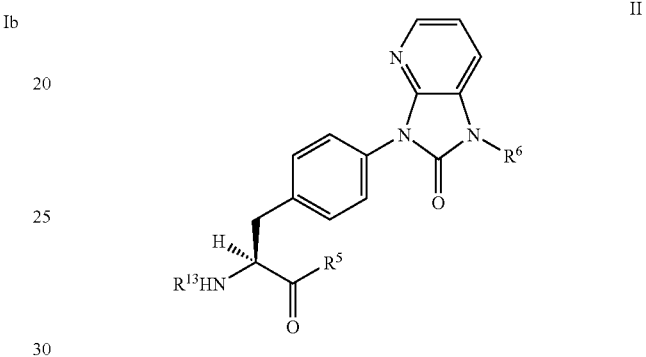

and pharmaceutically acceptable salts thereof, wherein $R^{13}$ is —H, the group —C(O)OR$^{13'}$, optionally substituted cycloalkyl, optionally substituted aryl, or optionally substituted heteroaryl;

wherein $R^{13'}$ is an optionally substituted alkyl, optionally substituted aryl, or an optionally substituted heteroaryl group.

Preferred compounds of formula Ia include compounds of formula III:

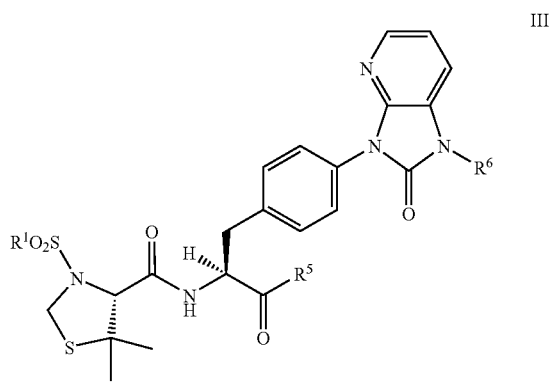

and pharmaceutically acceptable salts thereof, wherein $R^1$ is selected from the group consisting of alkyl, substituted alkyl, aryl, substituted aryl, cycloalkyl, substituted cycloalkyl, heterocyclic, substituted heterocyclic, heteroaryl and substituted heteroaryl.

Preferred compounds of Formula II include those where $R^6$ is hydrogen or substituted alkyl. More preferably, in compounds of Formula II, $R_6$ is hydrogen or alkyl substituted with hydroxy, halogen, amino, aminocarbonyl, $C_1$-$C_4$ alkoxy($C_1$-$C_4$) alkylaminocarbonyl, hydroxy($C_1$-$C_4$)alkylaminocarbonyl, or aminoalkoxyalkoxyalkyl.

Other preferred compounds of Formula II include those where Y is —SO$_2$—; and R$^1$ is phenyl or a 5- or 6-membered heteroaryl group having at least one nitrogen atom, each of which is optionally substituted with halogen, hydroxy, C$_1$-C$_6$ alkoxy, C$_1$-C$_6$ alkyl, nitro, trifluoromethyl, amino, mono- or di(C$_1$-C$_6$)alkylamino, amino(C$_1$-C$_6$)alkyl, C$_2$-C$_6$ acyl, C$_2$-C$_6$ acylamino, or amino(C$_1$-C$_6$)acyl. More preferably, Y is —SO$_2$— and R$^1$ is pyridyl optionally substituted with halogen, hydroxy, C$_1$-C$_6$ alkyl, C$_1$-C$_6$ alkoxy, nitro, trifluoromethyl, amino, mono- or di(C$_1$-C$_6$)alkylamino, amino(C$_1$-C$_6$) alkyl, C$_2$-C$_6$ acyl, C$_2$-C$_6$ acylamino, or amino(C$_1$-C$_6$)acyl. Particularly preferred compounds of Formula III include those where Y is —SO$_2$— and R$^1$ is pyridyl optionally substituted with C$_1$-C$_6$ alkyl, hydroxy, halogen, C$_1$-C$_6$ alkoxy, nitro, trifluoromethyl, amino, or mono- or di(C$_1$-C$_6$)alkylamino. Preferred compounds of formula Ib include compounds of formula IV:

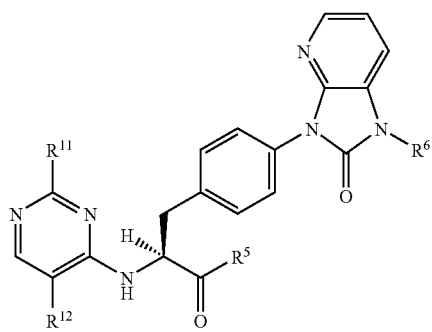

IV and pharmaceutically acceptable salts thereof, wherein R$^{11}$ is —H, R$^{11'}$, —NH$_2$, —NHR$^{11'}$ or —N(R$^{11'}$)$_2$, —NC$_3$-C$_6$cyclic, —OR$^{11'}$, —SR$^{11'}$, wherein each R$^{11'}$ is independently an optionally substituted straight or branched C$_1$-C$_6$alkyl, optionally substituted C$_3$-C$_6$cycloalkyl, optionally substituted aryl, optionally substituted heteroaryl, and R$^{12}$ is —H, —NO$_2$, haloalkyl or the group —N(YR$^1$) R$^2$ wherein Y is a covalent bond, —C(O)— or —SO$_2$—, R$^1$ is R$^{1'}$, N(R$^{1'}$)$_2$, or —OR$^{1'}$, wherein each R$^{1'}$ is independently hydrogen, an optionally substituted straight or branched C$_1$-C$_6$alkyl, optionally substituted cycloalkyl, optionally substituted aryl, optionally substituted heterocyclic or an optionally substituted heteroaryl, wherein optional substitutions are halide, C$_1$-C$_6$alkyl, —OC$_1$-C$_6$alkyl, and R$^2$ is hydrogen or R$^{1'}$.

Preferred compounds of Formula IV include those where R$^6$ is hydrogen or substituted alkyl. More preferably, in compounds of Formula IV, R$_6$ is hydrogen or alkyl substituted with amino, hydroxy, aminocarbonyl, C$_1$-C$_4$ alkoxy(C$_1$-C$_4$) alkylaminocarbonyl, hydroxy(C$_1$-C$_4$)alkylaminocarbonyl, or aminoalkoxyalkoxyalkyl.

Other preferred compounds of Formula IV include those where R$^{11}$ is amino or mono- or di(C$_1$-C$_6$)alkylamino; and R$^{12}$ is —H, —NO$_2$ or haloalkyl, more preferably trifluoromethylmethyl.

Still other preferred compounds of Formula IV are those where

R$^{11}$ is amino or mono- or di(C$_1$-C$_6$)alkylamino; and
R$^{12}$ is —N(YR$^1$)R$^2$; where
Y is —SO$_2$— or —CO—;
R$^1$ is
  C$_1$-C$_6$ alkyl optionally substituted with halogen, hydroxy, C$_1$-C$_6$ alkoxy, amino, or mono- or di(C$_1$-C$_6$) alkylamino; or
  phenyl or a 5- or 6-membered heteroaryl containing at least one nitrogen, each of which is optionally substituted with halogen, hydroxy, C$_1$-C$_6$ alkyl, C$_1$-C$_6$ alkoxy, C$_3$-C$_7$ cycloalkyl, amino, nitro, trifluoromethyl, or mono- or di(C$_1$-C$_6$)alkylamino; and R$^2$ is hydrogen, C$_1$-C$_6$alkyl, or C$_3$-C$_7$cycloalkyl. Preferred R$^1$ groups within Formula IV, R$^1$ is
  C$_1$-C$_4$ alkyl optionally substituted with halogen, hydroxy, C$_1$-C$_6$ alkoxy, amino, or mono- or di(C$_1$-C$_6$) alkylamino; or
  pyridyl or pyrimidinyl, each of which is optionally substituted with halogen, hydroxy, C$_1$-C$_3$ alkyl, C$_1$-C$_3$ alkoxy, amino, or mono- or di(C$_1$-C$_4$) alkylamino; and
R$^2$ is hydrogen, C$_1$-C$_4$alkyl, or C$_3$-C$_7$cycloalkyl.

A more preferred A group in compounds of Formula I is:

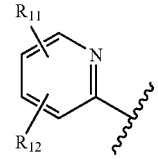

Formula A.1.

Another more preferred A group in compounds of Formula I is:

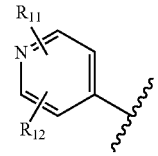

Formula A.2.

Still another more preferred A group in compounds of Formula I is:

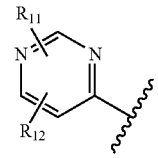

Formula A.3.

Still another more preferred A group in compounds of Formula I is:

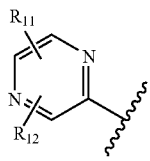

Formula A.4.

Still another more preferred A group in compounds of Formula I is:

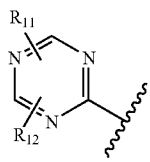

Formula A.5.

Still another more preferred A group in compounds of Formula I is:

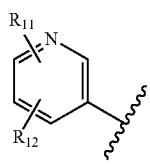

Formula A.6.

Still another more preferred A group in compounds of Formula I is:

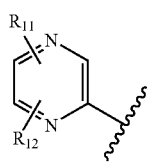

Formula I.7.
In each of Formulae A.1-A.7, $R^{11}$ and $R^{12}$ are as defined above for Formula IV.
In particularly preferred compounds having Formulae A.1-A.7,
  $R^{11}$ is amino or mono- or di($C_1$-$C_6$)alkylamino; and
  $R^{12}$ is —N(YR$^1$)R$^2$; where
    Y is —SO$_2$— or —CO—;
    $R^1$ is
      $C_1$-$C_6$ alkyl optionally substituted with halogen, hydroxy, $C_1$-$C_6$ alkoxy, amino, or mono- or di($C_1$-$C_6$) alkylamino; or
      phenyl or a 5- or 6-membered heteroaryl containing at least one nitrogen, each of which is optionally substituted with halogen, hydroxy, $C_1$-$C_6$ alkyl, $C_1$-$C_6$ alkoxy, $C_3$-$C_7$ cycloalkyl, amino, nitro, trifluoromethyl, or mono- or di($C_1$-$C_6$)alkylamino; and $R^2$ is hydrogen, $C_1$-$C_6$alkyl, or $C_3$-$C_7$cycloalkyl. Preferred $R^1$ groups within Formula IV, $R^1$ is
    $C_1$-$C_4$ alkyl optionally substituted with halogen, hydroxy, $C_1$-$C_6$ alkoxy, amino, or mono- or di($C_1$-$C_6$) alkylamino; or
    pyridyl or pyrimidinyl, each of which is optionally substituted with halogen, hydroxy, $C_1$-$C_3$ alkyl, $C_1$-$C_3$ alkoxy, amino, or mono- or di($C_1$-$C_4$) alkylamino; and
  $R^2$ is hydrogen, $C_1$-$C_4$alkyl, or $C_3$-$C_7$cycloalkyl.

A more preferred Q group in compounds of Formula I is:

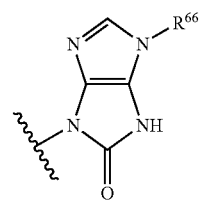

Formula Q.1.

Another more preferred Q group in compounds of Formula I is:

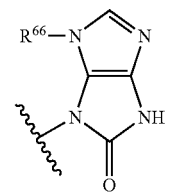

Formula Q.2.

Still another more preferred Q group in compounds of Formula I is:

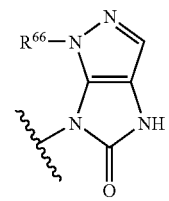

Formula Q.3.

Still another more preferred Q group in compounds of Formula I is:

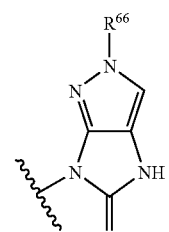

Formula Q.4.

Still another more preferred Q group in compounds of Formula I is:

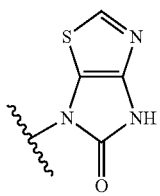

Formula Q.5.

Still another more preferred Q group in compounds of Formula I is:

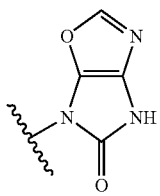

Formula Q.6.

Still another more preferred Q group in compounds of Formula I is:

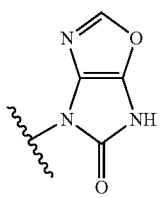

Formula Q.7.

Still another more preferred Q group in compounds of Formula I is:

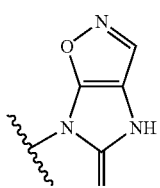

Formula Q.8.

Still another more preferred Q group in compounds of Formula I is:

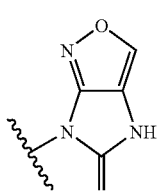

Formula Q.9.

Still another more preferred Q group in compounds of Formula I is:

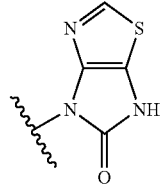

Formula Q.10.

Still another more preferred Q group in compounds of Formula I is:

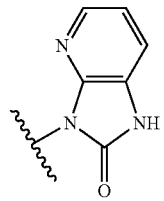

Formula Q.11.

Still another more preferred Q group in compounds of Formula I is:

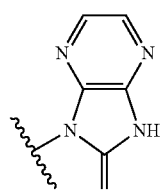

Formula Q.12.

Still another more preferred Q group in compounds of Formula I is:

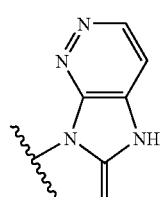

Formula Q.13.

Still another more preferred Q group in compounds of Formula I is:

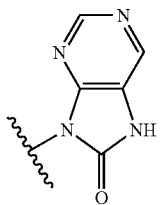

Formula Q.14.

Still another more preferred Q group in compounds of Formula I is:

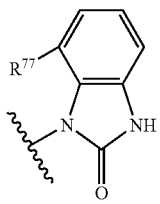

Formula Q.15.

In each of Formula Q.1-Q.15, $R^{66}$ is hydrogen or straight or branched $C_1$-$C_6$alkyl; and $R^{77}$ is hydrogen, halogen or straight or branched $C_1$-$C_6$alkoxy.

Preferably the compounds of the invention are of the L isomer as shown below:

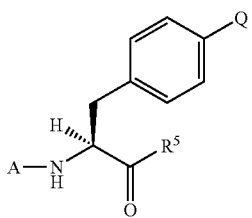

L-stereoisomer

In these compounds, A is defined as for formula I and Q is -(1-$R^6$-2-oxo-1,2-dihydroimidazo[4,5-b]pyridin-3-yl) wherein $R^6$ is —H, alkyl, substituted alkyl, or —CH$_2$C(O)$R^7$; $R^7$ is —OH, —O$R^8$, —NH$R^8$, and $R^8$ is alkyl, substituted alkyl, aryl or substituted aryl.

DEFINITIONS

As used herein, "alkyl" refers to linear and branched alkyl groups having from 1 to 10 carbon atoms and more preferably 1 to 6 carbon atoms. This term includes groups such as methyl, ethyl, propyl, isopropyl, n-butyl, t-butyl, n-heptyl, octyl and the like. Inclusion of $C_x$ wherein x is an integer, before the term alkyl denotes the number of carbon atoms in the alkyl chain, where a range is specified, both the smaller integer and the larger are included in the range.

"Optionally substituted alkyl" refers to an alkyl group that is unsubstituted or substituted with from 1 to 5 substituents independently selected from the group consisting of alkoxy, substituted alkoxy, acyl, acylamino, acyloxy, amino, substituted amino, aminoacyl, aminocarbonylamino, aminocarbonyloxy, aryl, substituted aryl, aryloxy, substituted aryloxy, carboxyl, carboxyl esters, cyano, cycloalkyl, substituted cycloalkyl, cycloalkyloxy, substituted cycloalkyloxy, halogen, heteroaryl, substituted heteroaryl, heteroaryloxy, substituted heteroaryloxy, heterocyclic, substituted heterocyclic, hydroxyl, nitro, and oxycarbonylamino.

"Alkylene" refers to linear and branched divalent alkylene groups having from 1 to 10 carbon atoms and more preferably 1 to 6 carbon atoms. This term is exemplified by groups such as methylene, 1,6-heptylene, 1,8-octylene and the like which are optionally substituted with from 1 to 5 substituents as defined for substituted alkyl above.

"Alkoxy" refers to the group "alkyl-O—" which includes, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

"Substituted alkoxy" refers to the group "substituted alkyl-O—".

Each alkyl of "alkyl-O-alkyl" is optionally independently substituted with 1 to 5 substituents independently selected from the group consisting of alkoxy, substituted alkoxy, acyl, acylamino, acyloxy, amino, substituted amino, aminoacyl, aminocarbonylamino, aminocarbonyloxy, aryl, substituted aryl, aryloxy, substituted aryloxy, carboxyl, carboxyl esters, cyano, cycloalkyl, substituted cycloalkyl, cycloalkyloxy, substituted cycloalkyloxy, halogen, heteroaryl, substituted heteroaryl, heteroaryloxy, substituted heteroaryloxy, heterocyclic, substituted heterocyclic, hydroxyl, nitro, and oxycarbonylamino.

"Alkenyl" refers to alkenyl groups having from 2 to 10 carbon atoms and more preferably 2 to 6 carbon atoms and having at least 1 and preferably from 1-2 sites of alkenyl unsaturation.

"Optionally substituted alkenyl" refers to alkenyl groups that are unsubstituted or substituted with from 1 to 5 substituents independently selected from the group consisting of alkoxy, substituted alkoxy, acyl, acylamino, acyloxy, amino, substituted amino, aminoacyl, aminocarbonylamino, aminocarbonyloxy, aryl, substituted aryl, aryloxy, substituted aryloxy, carboxyl, carboxyl esters, cyano, cycloalkyl, substituted cycloalkyl, cycloalkyloxy, substituted cycloalkyloxy, halogen, heteroaryl, substituted heteroaryl, heteroaryloxy, substituted heteroaryloxy, heterocyclic, substituted heterocyclic, hydroxyl, nitro, and oxycarbonylamino.

"Acyl" refers to the groups H—C(O)—, alkyl-C(O)—, substituted alkyl-C(O)—, alkenyl-C(O)—, substituted alkenyl-C(O)—, cycloalkyl-C(O)—, substituted cycloalkyl-C(O)—, aryl-C(O)—, substituted aryl-C(O)—, heteroaryl-C(O)—, substituted heteroaryl-C(O), heterocyclic-C(O)—, and substituted heterocyclic-C(O)—.

"Acylamino" refers to the group —C(O)N$R^{30}R^{30}$ where each $R^{30}$ is independently selected from the group consisting of hydrogen, alkyl, substituted alkyl, alkenyl, substituted alkenyl, aryl, substituted aryl, cycloalkyl, substituted cycloalkyl, heteroaryl, substituted heteroaryl, heterocyclic, substituted heterocyclic and where each $R^{30}$ is joined to form together with the nitrogen atom a heterocyclic or substituted heterocyclic ring.

"Acyloxy" refers to the groups alkyl-C(O)O—, substituted alkyl-C(O)O—, alkenyl-C(O)O—, substituted alkenyl-C(O)O—, aryl-C(O)O—, substituted aryl-C(O)O—, cycloalkyl-C(O)O—, substituted cycloalkyl-C(O)O—, heteroaryl-C(O)

O—, substituted heteroaryl-C(O)O—, heterocyclic-C(O)O—, and substituted heterocyclic-C(O)O—.

"Amino" refers to the group —NH$_2$.

"Substituted amino" refers to the group —NR$^{31}$R$^{31}$, where each R$^{31}$ group is independently selected from the group consisting of hydrogen, alkyl, substituted alkyl, alkenyl, substituted alkenyl, cycloalkyl, substituted cycloalkyl, aryl, substituted aryl, heteroaryl, substituted heteroaryl, heterocyclic, and substituted heterocyclic, provided that both R$^{31}$ groups are not hydrogen; or where the R$^{31}$ groups can be joined together with the nitrogen atom to form a heterocyclic or substituted heterocyclic ring.

"Aminoacyl" refers to the groups —NR$^{32}$C(O)alkyl, —NR$^{32}$C(O) substituted alkyl, —NR$^{32}$C(O)cycloalkyl, —NR$^{32}$C(O) substituted cycloalkyl, —NR$^{32}$C(O)alkenyl, —NR$^{32}$C(O) substituted alkenyl, —NR$^{32}$C(O)aryl, —NR$^{32}$C(O) substituted aryl, —NR$^{32}$C(O)heteroaryl, —NR$^{32}$C(O) substituted heteroaryl, —NR$^{32}$C(O)heterocyclic, and —NR$^{32}$C(O) substituted heterocyclic where each R$^{32}$ is hydrogen or alkyl.

"Aminocarbonyloxy" refers to the groups —NR$^{32}$C(O)O-alkyl, —NR$^{32}$C(O)O-substituted alkyl, —NR$^{32}$C(O)O-alkenyl, —NR$^{32}$C(O)O-substituted alkenyl, —NR$^{32}$C(O)O-cycloalkyl, —NR$^{32}$C(O)O-substituted cycloalkyl, —NR$^{32}$C(O)O-aryl, —NR$^{32}$C(O)O-substituted aryl, —NR$^{32}$C(O)O-heteroaryl, —NR$^{32}$C(O)O-substituted heteroaryl, —NR$^{32}$C(O)O-heterocyclic, and —NR$^{32}$C(O)O-substituted heterocyclic where R$^{32}$ is hydrogen or alkyl.

"Oxycarbonylamino" refers to the groups —OC(O)—amino and —OC(O)-substituted amino.

"Aminocarbonylamino" refers to the groups —NR$^{32}$C(O)-amino and —NR$^{32}$C(O)-substituted amino where R$^{32}$ is hydrogen or alkyl.

"Aryl" or "Ar" refers to an unsaturated aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7yl, and the like) provided that the point of attachment is through an aromatic ring atom. Preferred aryls include phenyl, naphthyl and 5,6,7,8-tetrahydronaphth-2-yl. Particular preferred aryl groups are phenyl groups.

"Optionally substituted aryl" refers to aryl groups that are unsubstituted or substituted with from 1 to 5, preferably 1-3 substituents selected from the group consisting of hydroxy, acyl, acylamino, acyloxy, alkyl, substituted alkyl, alkoxy, substituted alkoxy, alkenyl, substituted alkenyl, amino, substituted amino, aminoacyl, aminocarbonyloxy, aminocarbonylamino, aryl, substituted aryl, aryloxy, substituted aryloxy, cycloalkyloxy, substituted cycloalkyloxy, heteroaryloxy, substituted heteroaryloxy, heterocyclyloxy, substituted heterocyclyloxy, carboxyl, carboxyl esters, cyano, cycloalkyl, substituted cycloalkyl, halo, nitro, heteroaryl, substituted heteroaryl, heterocyclic, substituted heterocyclic, and oxycarbonylamino. Particular preferred optionally substituted aryl groups are optionally substituted phenyl groups.

"Aryloxy" refers to the group aryl-O— which includes, by way of example, phenoxy, naphthoxy, and the like.

"Substituted aryloxy" refers to substituted aryl-O— groups.

"Carboxyl" refers to the group —COOH and pharmaceutically acceptable salts thereof.

"Carboxyl esters" refers —C(O)O-alkyl, —C(O)O-substituted alkyl, —C(O)O-alkenyl, —C(O)O-substituted alkenyl, —C(O)O-aryl, —C(O)O-substituted aryl, —C(O)O-cycloalkyl, —C(O)O-substituted cycloalkyl, —C(O)O-heteroaryl —C(O)O-substituted heteroaryl, —C(O)O-heterocyclic, and —C(O)O-substituted heterocyclic.

"Cycloalkyl" refers to cyclic alkyl groups of from 3 to 12 carbon atoms having a single or multiple condensed rings including, by way of example, adamantyl, cyclopropyl, cyclobutyl, cyclopentyl, cyclohexyl, cyclooctyl and the like.

"Optionally substituted cycloalkyl" refers to a cycloalkyl group that is unsubstituted or substituted with from 1 to 5, preferably 1-3, substituents selected from the group consisting of oxo (=O), thioxo (=S), alkyl, substituted alkyl, alkoxy, substituted alkoxy, acyl, acylamino, acyloxy, amino, substituted amino, aminoacyl, aminocarbonylamino, aminocarbonyloxy, aryl, substituted aryl, aryloxy, substituted aryloxy, carboxyl, carboxyl esters, cyano, cycloalkyl, substituted cycloalkyl, cycloalkyloxy, substituted cycloalkyloxy, halogen, heteroaryl, substituted heteroaryl, heteroaryloxy, substituted heteroaryloxy, heterocyclic, substituted heterocyclic, hydroxyl, nitro, and oxycarbonylamino.

"Cycloalkyloxy" refers to cycloalkyl-O— groups.

"Substituted cycloalkyloxy" refers to cycloalkyl groups that are substituted on the cycloalkyl portion.

"Halo" or "halogen" refers to fluoro, chloro, bromo and iodo and preferably is fluoro, chloro or bromo.

"Heteroaryl" refers to an aromatic group of from 2 to 10 carbon atoms and 1 to 4 heteroatoms selected from oxygen, nitrogen and sulfur within the ring or oxides thereof. Such heteroaryl groups can have a single ring (e.g., pyridyl or furyl) or multiple condensed rings wherein one or more of the condensed rings may or may not be aromatic provided that the point of attachment is through an aromatic ring atom. Additionally, the heteroatoms of the heteroaryl group may be oxidized, i.e., to form pyridine N-oxides or 1,1-dioxo-1,2,5-thiadiazoles and the like. Preferred heteroaryls include pyridyl, pyrrolyl, indolyl, furyl, pyridazinyl, pyrimidinyl, pyrazinyl, 1-oxo-1,2,5-thiadiazolyl and 1,1-dioxo-1,2,5-thiadiazolyl.

"Optionally substituted heteroaryl" refers to heteroaryl groups that are unsubstituted or substituted with from 1 to 5, preferably 1-3 substituents selected from the group consisting of those defined above for substituted aryl.

"Heteroaryloxy" refers to the group —O-heteroaryl and "substituted heteroaryloxy" refers to the group —O-substituted heteroaryl.

"Heterocycle," "heterocyclic" or "heterocyclyl" refers to a saturated or unsaturated group having a single ring or multiple condensed rings, from 1 to 10 carbon atoms and from 1 to 4 hetero atoms selected from nitrogen, sulfur or oxygen within the ring wherein, in fused ring systems, one or more of the rings can be aryl or heteroaryl, provided that the point of attachment is through a heterocyclic ring atom.

The term "—NC$_3$-C$_6$cyclic" as used herein means 4-7 membered heterocyclic groups where the point of attachment to a parent group is the nitrogen atom in the heterocyclic ring. Examples of —NC$_3$-C$_6$cyclic groups are piperidin-1-yl, homopiperidin-1-yl, and azetidin-1-yl, and pyrrolidin-1-yl. Each of these —NC$_3$-C$_6$cyclic groups can be substituted on the ring with C$_1$-C$_6$ alkyl, C$_1$-C$_6$ alkoxy, hydroxy, halogen, amino, mono- and di-(C$_1$-C$_6$)alkylamino, nitro, and trifluoromethyl.

"Optionally substituted heterocycle," "substituted heterocyclic" and "substituted heterocyclyl" refer to heterocycle groups that are unsubstituted or substituted with from 1 to 5, preferably 1-3 substituents selected from the group consisting of those defined for substituted cycloalkyl.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholino, thiomorpholino, piperidinyl, pyrrolidine, tetrahydrofuranyl, and the like.

"Heterocyclyloxy" refers to the group —O-heterocyclic and "substituted heterocyclyloxy" refers to the group —O-substituted heterocyclic.

The terms "compound" and "active compound" are used to refer to the VLA-4 antagonist.

"Pharmaceutically acceptable salt" refers to salts which retain the biological effectiveness and properties of the compounds of this invention and which are not biologically or otherwise undesirable. In many cases, the compounds of this invention are capable of forming acid and/or base salts by virtue of the presence of amino and/or carboxyl groups or groups similar thereto.

Pharmaceutically-acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and triamines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group.

Examples of suitable amines include, by way of non-limiting example only, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like. It should also be understood that other carboxylic acid derivatives would be useful in the practice of this invention, for example, carboxylic acid amides, including carboxamides, lower alkyl carboxamides, dialkyl carboxamides, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

The term "pharmaceutically-acceptable cation" refers to the cation of a pharmaceutically-acceptable salt.

It is understood that in all substituted groups defined herein, polymers arrived at by defining substituents with further substituents to themselves (e.g., substituted aryl having a substituted aryl group as a substituent which is itself substituted with a substituted aryl group, etc.) are not intended for inclusion herein. In such cases, the maximum number of such substituents is three. That is to say that each of the above definitions is constrained by a limitation that, for example, substituted aryl groups are limited to -substituted aryl-(substituted aryl)-(substituted aryl).

Similarly, it is understood that the above definitions are not intended to include impermissible substitution patterns (e.g., methyl substituted with 5 fluoro groups or a hydroxyl group alpha to ethylenic or acetylenic unsaturation). Such impermissible substitution patterns are well known to the skilled artisan.

When employed as pharmaceuticals, the compounds of this invention are usually administered in the form of pharmaceutical compositions. These compositions can be administered by a variety of routes including oral, rectal, transdermal, subcutaneous, intravenous, intramuscular, and intranasal. Preferred administration routes include subcutaneous and intravenous. Particularly preferred is subcutaneous. Such compositions are prepared in a manner well known in the pharmaceutical art and comprise at least one active compound.

The invention also provides pharmaceutical compositions comprising a compound according to the invention, e.g., a compound of Formula I, in combination with a separate compound which is an $\alpha_4\beta_7$ inhibitor. Such compositions will also comprise a pharmaceutically acceptable carrier or excipient and may be administered as discussed elsewhere herein.

This invention also includes pharmaceutical compositions which contain, as the active ingredient, one or more of the compounds of formula I above associated with pharmaceutically acceptable carriers. In making the compositions of this invention, the active ingredient is usually mixed with an excipient, diluted by an excipient or enclosed within such a carrier which can be in, sterile injectable solutions, and sterile packaged powders. For subcutaneous administration, a simple carrier may comprise a sterile solution of water, Na2HPO4, NaH2PO4, and NaCl, in proportions that provide an isotonic and physiologically acceptable pH, also know as PBS or phosphate-buffered saline. Other options are known to those of skill in the art and include mixed solvent systems that can affect the rate of absorption and total exposure. These options include mixed solvent systems containing glycerin, Polyethylene glycol 400, and cottonseed oil. Also of potential use are ethanol, N,N'-dimethylacetamide, propylene glycol and benzyl alcohol all of which may be used to manipulate permeability enhancement and hypertonicity.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

Administration of therapeutic agents by subcutaneous or intravenous formulation is well known in the pharmaceutical industry. A subcutaneous or intravenous formulation should possess certain qualities aside from being just a composition in which the therapeutic agent is soluble. For example, the formulation should promote the overall stability of the active ingredient(s), also, the manufacture of the formulation should be cost effective. All of these factors ultimately determine the overall success and usefulness of an intravenous formulation.

Other accessory additives that may be included in pharmaceutical formulations of compounds of the present invention as follow: solvents: ethanol, glycerol, propylene glycol; stabilizers: EDTA (ethylene diamine tetraacetic acid), citric acid; antimicrobial preservatives: benzyl alcohol, methyl paraben, propyl paraben; buffering agents: citric acid/sodium citrate, potassium hydrogen tartrate, sodium hydrogen tartrate, acetic acid/sodium acetate, maleic acid/sodium maleate, sodium hydrogen phthalate, phosphoric acid/potassium dihydrogen phosphate, phosphoric acid/disodium hydrogen phosphate; and tonicity modifiers: sodium chloride, mannitol, dextrose.

The presence of a buffer is necessary to maintain the aqueous pH in the range of from about 4 to about 8 and more preferably in a range of from about 4 to about 6. The buffer system is generally a mixture of a weak acid and a soluble salt thereof, e.g., sodium citrate/citric acid; or the monocation or dication salt of a dibasic acid, e.g., potassium hydrogen tartrate; sodium hydrogen tartrate, phosphoric acid/potassium dihydrogen phosphate, and phosphoric acid/disodium hydrogen phosphate.

The amount of buffer system used is dependent on (1) the desired pH; and (2) the amount of drug. Generally, the amount of buffer used is in a 0.5:1 to 50:1 mole ratio of buffer: alendronate (where the moles of buffer are taken as the combined moles of the buffer ingredients, e.g., sodium citrate and citric acid) of formulation to maintain a pH in the range of 4 to 8 and generally, a 1:1 to 10:1 mole ratio of buffer (combined) to drug present is used.

A useful buffer in the invention is sodium citrate/citric acid in the range of 5 to 50 mg per ml. sodium citrate to 1 to 15 mg per ml. citric acid, sufficient to maintain an aqueous pH of 4-6 of the composition.

The buffer agent may also be present to prevent the precipitation of the drug through soluble metal complex formation with dissolved metal ions, e.g., Ca, Mg, Fe, Al, Ba, which may leach out of glass containers or rubber stoppers or be present in ordinary tap water. The agent may act as a competitive complexing agent with the drug and produce a soluble metal complex leading to the presence of undesirable particulates.

In addition, the presence of an agent, e.g., sodium chloride in an amount of about of 1-8 mg/ml, to adjust the tonicity to the same value of human blood may be required to avoid the swelling or shrinkage of erythrocytes upon administration of the intravenous formulation leading to undesirable side effects such as nausea or diarrhea and possibly to associated blood disorders. In general, the tonicity of the formulation matches that of human blood which is in the range of 282 to 288 mOsm/kg, and in general is 285 mOsm/kg, which is equivalent to the osmotic pressure corresponding to a 0.9% solution of sodium chloride.

The intravenous formulation can be administered by direct intravenous injection, i.v. bolus, or can be administered by infusion by addition to an appropriate infusion solution such as 0.9% sodium chloride injection or other compatible infusion solution.

The compositions are preferably formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The compound is effective over a wide dosage range and is generally administered in a pharmaceutically effective amount. It, will be understood, however, that the amount of the compound actually administered will be determined by a physician, in the light of the relevant circumstances, including the condition to be treated, the chosen route of administration, the actual compound administered, the age, weight, and response of the individual patient, the severity of the patient's symptoms, and the like.

For preparing solid compositions such as tablets, the principal compound is mixed with a pharmaceutical excipient to form a solid preformulation composition containing a homogeneous mixture of a compound of the present invention. When referring to these preformulation compositions as homogeneous, it is meant that the compound is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be breathed directly from the nebulizing device or the nebulizing device may be attached to a face masks tent, or intermittent positive pressure breathing machine. Solution, suspension, or powder compositions may be administered, preferably orally or nasally, from devices which deliver the formulation in an appropriate manner.

The compounds of this invention are VLA-4 antagonists and some have a partial affinity for alpha4 beta7 integrins. The drug formulation may be administered less frequently to the patient while achieving a similar or improved therapeutic effect.

The compounds of this invention have improved inhibition, in vivo, of adhesion of leukocytes to endothelial cells mediated by VLA-4 by competitive binding to VLA-4. Preferably, the compounds of this invention can be used, e.g., by infusion, or by subcutaneous or oral administration, for the treatment of diseases mediated by VLA-4 or leucocyte adhesion. The compounds of the invention can be used to treat a variety of inflammatory brain disorders, especially central nervous system disorders in which the endothelium/leukocyte adhesion mechanism results in destruction to otherwise healthy brain tissue. Thus, the compounds of the invention can be used for, e.g., the treatment of experimental autoimmune encephalomyelitis (EAE), multiple sclerosis (MS), meningitis, and encephalitis.

The compounds of the invention can also be used to treat disorders and diseases due to tissue damage in other organ systems, i.e., where tissue damage also occurs via an adhesion mechanism resulting in migration or activation of leukocytes. Examples of such diseases in mammalian patients are inflammatory diseases such as asthma, Alzheimer's disease, atherosclerosis, AIDS dementia, diabetes (including acute juvenile onset diabetes), inflammatory bowel disease (including ulcerative colitis and Crohn's disease), rheumatoid arthritis, tissue transplantation rejection, tumor metastasis, stroke, and other cerebral traumas, nephritis, retinitis, atopic dermatitis, psoriasis, myocardial ischemia and acute leukocyte-mediated lung injury such as that which occurs in adult respiratory distress syndrome.

Still other disease conditions which may be treated using compounds of the invention include erythema nodosum, allergic conjunctivitis, optic neuritis, uveitis, allergic rhinitis, ankylosing spondylitis, psoriatic arthritis, vasculitis, Reiter's syndrome, systemic lupus erythematosus, progressive systemic sclerosis, polymyositis, dermatomyositis, Wegner's granulomatosis, aortitis, sarcoidosis, lymphocytopenia, temporal arteritis, pericarditis, myocarditis, congestive heart failure, polyarteritis nodosa, hypersensitivity syndromes, allergy, hypereosinophilic syndromes, Churg-Strauss syndrome, chronic obstructive pulmonary disease, hypersensitivity pneumonitis, chronic active hepatitis, interstitial cystitis, autoimmune endocrine failure, primary biliary cirrhosis, autoimmune aplastic anemia, chronic persistent hepatitis and thyroiditis.

The invention also provides methods for treating a disease state caused or exacerbated at least in part by alpha 4 integrin-mediated lekocyte binding in a patient, which methods comprise co-administration of an effective amount of a compound of the invention, e.g., a compound of Formula I, and an effective amount of a separate compound which is an $\alpha_4\beta_7$ inhibitor. The co-administration can be carried out simultaneously or sequentially. For example, administration of the compound of the invention can precede administration of the $\alpha_4\beta_7$ inhibitor by minutes or hours. Alternatively, the $\alpha_4\beta_7$ inhibitor can be administered prior to the compounds of the invention.

Appropriate in vivo models for demonstrating efficacy in treating inflammatory responses include EAE (experimental autoimmune encephalomyelitis) in mice, rats, guinea pigs or primates, as well as other inflammatory models dependent upon $\alpha 4$ integrins.

Inflammatory bowel disease is a collective term for two similar diseases referred to as Crohn's disease and ulcerative colitis. Crohn's disease is an idiopathic, chronic ulceroconstrictive inflammatory disease characterized by sharply delimited and typically transmural involvement of all layers of the bowel wall by a granulomatous inflammatory reaction. Any segment of the gastrointestinal tract, from the mouth to the anus, may be involved, although the disease most commonly affects the terminal ileum and/or colon. Ulcerative colitis is an inflammatory response limited largely to the colonic mucosa and submucosa. Lymphocytes and macrophages are numerous in lesions of inflammatory bowel disease and may contribute to inflammatory injury.

Asthma is a disease characterized by increased responsiveness of the tracheobronchial tree to various stimuli potentiating paroxysmal constriction of the bronchial airways. The stimuli cause release of various mediators of inflammation from IgE-coated mast cells including histamine, eosinophilic and neutrophilic chemotactic factors, leukotrines, prostaglandin and platelet activating factor. Release of these factors recruits basophils, eosinophils and neutrophils, which cause inflammatory injury.

Atherosclerosis is a disease of arteries (e.g., coronary, carotid, aorta and iliac). The basic lesion, the atheroma, consists of a raised focal plaque within the intima, having a core of lipid and a covering fibrous cap. Atheromas compromise arterial blood flow and weaken affected arteries. Myocardial and cerebral infarcts are a major consequence of this disease. Macrophages and leukocytes are recruited to atheromas and contribute to inflammatory injury.

Rheumatoid arthritis is a chronic, relapsing inflammatory disease that primarily causes impairment and destruction of joints. Rheumatoid arthritis usually first affects the small joints of the hands and feet but then may involve the wrists, elbows, ankles and knees. The arthritis results from interaction of synovial cells with leukocytes that infiltrate from the circulation into the synovial lining of the joints. See e.g., Paul, Immunology (3d ed., Raven Press, 1993).

Another indication for the compounds of this invention is in treatment of organ or graft rejection mediated by VLA-4. Over recent years there has been a considerable improvement in the efficiency of surgical techniques for transplanting tissues and organs such as skin, kidney, liver, heart, lung, pancreas and bone marrow. Perhaps the principal outstanding problem is the lack of satisfactory agents for inducing immunotolerance in the recipient to the transplanted allograft or organ. When allogeneic cells or organs are transplanted into a host (i.e., the donor and donee are different individuals from the same species), the host immune system is likely to mount an immune response to foreign antigens in the transplant (host-versus-graft disease) leading to destruction of the transplanted tissue. CD8$^+$ cells, CD4 cells and monocytes are all involved in the rejection of transplant tissues. Compounds of this invention which bind to alpha-4 integrin are useful, inter alia, to block alloantigen-induced immune responses in the donee thereby preventing such cells from participating in the destruction of the transplanted tissue or organ. See, e.g., Paul et al., Transplant International 9, 420-425 (1996); Georczynski et al., Immunology 87, 573-580 (1996); Georcyznski et al., Transplant. Immunol. 3, 55-61 (1995); Yang et al., Transplantation 60, 71-76 (1995); Anderson et al., APMIS 102, 23-27 (1994).

A related use for compounds of this invention which bind to VLA-4 is in modulating the immune response involved in "graft versus host" disease (GVHD). See e.g., Schlegel et al., J. Immunol. 155, 3856-3865 (1995). GVHD is a potentially fatal disease that occurs when immunologically competent cells are transferred to an allogeneic recipient. In this situation, the donor's immunocompetent cells may attack tissues in the recipient. Tissues of the skin, gut epithelia and liver are frequent targets and may be destroyed during the course of GVHD. The disease presents an especially severe problem when immune tissue is being transplanted, such as in bone marrow transplantation; but less severe GVHD has also been reported in other cases as well, including heart and liver transplants. The therapeutic agents of the present invention are used, inter alia, to block activation of the donor T-cells thereby interfering with their ability to lyse target cells in the host.

The formulations of the present invention are especially useful in the treatment of multiple sclerosis, rheumatoid arthritis and asthma.

A further use of the compounds of this invention is inhibiting tumor metastasis. Several tumor cells have been reported to express VLA-4 and compounds which bind VLA-4 block adhesion of such cells to endothelial cells. Steinback et al., Urol. Res. 23, 175-83 (1995); Orosz et al., Int. J. Cancer 60, 867-71 (1995); Freedman et al., Leuk. Lymphoma 13, 47-52 (1994); Okahara et al., Cancer Res. 54, 3233-6 (1994).

Compounds having the desired biological activity may be modified as necessary to provide desired properties such as improved pharmacological properties (e.g., in vivo stability, bio-availability), or the ability to be detected in diagnostic applications. Stability can be assayed in a variety of ways such as by measuring the half-life of the proteins during incubation with peptidases or human plasma or serum. A number of such protein stability assays have been described (see, e.g., Verhoef et al., Eur. J. Drug Metab. Pharmacokinet., 1990, 15(2):83-93).

A further use of the compounds of this invention is in treating multiple sclerosis. Multiple sclerosis is a progressive neurological autoimmune disease that affects an estimated 250,000 to 350,000 people in the United States. Multiple sclerosis is thought to be the result of a specific autoimmune reaction in which certain leukocytes attack and initiate the destruction of myelin, the insulating sheath covering nerve fibers. In an animal model for multiple sclerosis, murine monoclonal antibodies directed against VLA-4 have been shown to block the adhesion of leukocytes to the endothelium, and thus prevent inflammation of the central nervous system and subsequent paralysis in the animals[16].

Pharmaceutical compositions of the invention are suitable for use in a variety of drug delivery systems. Suitable formulations for use in the present invention are found in Remington's Pharmaceutical Sciences, Mace Publishing Company, Philadelphia, Pa., 17th ed. (1985).

The amount administered to the patient will vary depending upon what is being administered, the purpose of the administration, such as prophylaxis or therapy, the state of the patient, the manner of administration, and the like. In therapeutic applications, compositions are administered to a patient already suffering from a disease in an amount sufficient to cure or at least partially arrest the symptoms of the disease and its complications. An amount adequate to accomplish this is defined as "therapeutically effective dose."

Amounts effective for this use will depend on the disease condition being treated as well as by the judgment of the attending clinician depending upon factors such as the severity of the inflammation, the age, weight and general condition of the patient, and the like.

The compositions administered to a patient are in the form of pharmaceutical compositions described above. These compositions may be sterilized by conventional sterilization techniques, or may be sterile filtered. The resulting aqueous solutions may be packaged for use as is, or lyophilized, the lyophilized preparation being combined with a sterile aqueous carrier prior to administration.

The therapeutic dosage of the compounds of the present invention will vary according to, for example, the particular use for which the treatment is made, the manner of administration of the compound, the health and condition of the patient, and the judgment of the prescribing physician. For example, for intravenous administration, the dose will typically be in the range of about 20 µg to about 2000 µg per kilogram body weight, preferably about 20 µg to about 500 µg, more preferably about 100 µg to about 300 µg per kilogram body weight. Suitable dosage ranges for intranasal administration are generally about 0.1 pg to 1 mg per kilogram body weight. Effective doses can be extrapolated from dose-response curves derived from in vitro or animal model test systems.

Compounds of this invention are also capable of binding or antagonizing the actions of $\alpha_6\beta_1$, $\alpha_9\beta_1$, $\alpha_4\beta_7$, $\alpha_d\beta_2$, $\alpha_e\beta_7$ integrins (although $\alpha_4\beta_1$ and $\alpha_9\beta_1$ are preferred in this invention). Accordingly, compounds of this invention are also useful for preventing or reversing the symptoms, disorders or diseases induced by the binding of these integrins to their respective ligands.

For example, International Publication Number WO 98/53817, published Dec. 3, 1998 (the disclosure of which is incorporated herein by reference in its entirety) and references cited therein describe disorders mediated by $\alpha_4\alpha_7$. This reference also describes an assay for determining antagonism of $\alpha_4\beta_7$ dependent binding to VCAM-Ig fusion protein.

Additionally, compounds that bind $\alpha_d\beta_2$ and $\alpha_e\beta_7$ integrins are particularly useful for the treatment of asthma and related lung diseases. See, for example, M. H. Grayson et al., *J. Exp. Med.* 1998, 188 (11) 2187-2191. Compounds that bind $\alpha_e\beta_7$ integrin are also useful for the treatment of systemic lupus erythematosus (see, for example, M. Pang et al., *Arthritis Rheum.* 1998, 41 (8), 1456-1463); Crohn's disease, ulcerative colitis and inflammatory bowel disease (IBD) (see, for example, D. Elewaut et al., *Scand J. Gastroenterol* 1998, 33 (7) 743-748); Sjogren's syndrome (see, for example, U. Kroneld et al., *Scand J. Gastroenterol* 1998, 27 (3), 215-218); and rheumatoid arthritis (see, for example, *Scand J. Gastroenterol* 1996, 44 (3), 293-298). And compounds that bind $\alpha_6\beta_1$ may be useful in preventing fertilization (see, for example, H. Chen et al., *Chem. Biol.* 1999, 6, 1-10).

In another aspect of the invention, the compounds and compositions described herein can be used to inhibit immune cell migration from the bloodstream to the central nervous system in the instance of, for example, multiple sclerosis, or to areas which result in inflammatory-induced destruction of the myelin. Preferably, these reagents inhibit immune cell migration in a manner that inhibits demyelination and that further may promote remyelination. The reagents may also prevent demyelination and promote remyelination of the central nervous system for congenital metabolic disorders in which infiltrating immune cells affect the development myelin sheath, mainly in the CNS. The reagents preferably also reduce paralysis when administered to a subject with paralysis induced by a demyelinating disease or condition.

Inflammatory diseases that are included for treatment by the compositions, compounds and methods disclosed herein include generally conditions relating to demyelination. Histologically, myelin abnormalities are either demyelinating or dysmyelinating. Demyelination implies the destruction of myelin. Dysmyelination refers to defective formation or maintenance of myelin resulting from dysfunction of the oligodendrocytes. Preferably, the compositions and methods disclosed herein are contemplated to treat diseases and conditions relating to demyelination and aid with remyelination. Additional diseases or conditions contemplated for treatment include meningitis, encephalitis, and spinal cord injuries and conditions generally which induce demyelination as a result of an inflammatory response. The compounds, compositions and methods disclosed herein are not directed towards diseases and conditions wherein there is, for example, a genetic defect leading to improper myelin formation, e.g., dysmyelination.

The compositions, compounds and cocktails disclosed herein are contemplated for use in treating conditions and diseases associated with demyelination. Diseases and conditions involving demyelination include, but are not limited to, multiple sclerosis, congenital metabolic disorders (e.g., phenylketonuria, Tay-Sachs disease, Niemann-Pick disease, Gaucher's disease, Hurler's syndrome, Krabbe's disease and other leukodystrophies), neuropathies with abnormal myelination (e.g., Guillain Barré, chronic immune demyelinating polyneuropathy (CIDP), multifocal CIDP, anti-MAG syndrome, GALOP syndrome, anti-sulfatide antibody syndrome, anti-GM2 antibody syndrome, POEMS syndrome, perineuritis, IgM anti-GD1b antibody syndrome), drug related demyelination (e.g., caused by the administration of chloroquine, FK506, perhexiline, procainamide, and zimeldine), other hereditary demyelinating conditions (e.g., carbohydrate-deficient glycoprotein, Cockayne's syndrome, congenital hypomyelinating, congenital muscular dystrophy, Farber's disease, Marinesco-Sjögren syndrome, metachromatic leukodystrophy, Pelizaeus-Merzbacher disease, Refsum disease, prion related conditions, and Salla disease) and other demyelinating conditions (e.g., meningitis, encephalitis or spinal cord injury) or diseases.

There are various disease models that can be used to study these diseases in vivo. For example, animal models include but are not limited to:

TABLE III

| Disease Model | Species |
| --- | --- |
| EAE | Mouse, rat, guinea pig |
| Myelin-oligodendrocyte glycoprotein (MOG) induced EAE | Rat |
| TNF-α transgenic model of demyelination | Mouse |

Multiple Sclerosis

The most common demyelinating disease is multiple sclerosis, but many other metabolic and inflammatory disorders result in deficient or abnormal myelination. MS is a chronic neurologic disease, which appears in early adulthood and progresses to a significant disability in most cases. There are approximately 350,000 cases of MS in the United States alone. Outside of trauma, MS is the most frequent cause of neurologic disability in early to middle adulthood.

The cause of MS is yet to be determined. MS is characterized by chronic inflammation, demyelination and gliosis (scarring). Demyelination may result in either negative or positive effects on axonal conduction. Positive conduction abnormalities include slowed axonal conduction, variable conduction block that occurs in the presence of high-but not low-frequency trains of impulses or complete conduction block. Positive conduction abnormalities include ectopic impulse generation, spontaneously or following mechanical stress and abnormal "cross-talk" between demyelinated exons.

T cells reactive against myelin proteins, either myelin basic protein (MBP) or myelin proteolipid protein (PLP) have been observed to mediate CNS inflammation in experimental allergic encephalomyelitis. Patients have also been observed as having elevated levels of CNS immunoglobulin (Ig). It is further possible that some of the tissue damage observed in MS is mediated by cytokine products of activated T cells, macrophages or astrocytes.

Today, 80% patients diagnosed with MS live 20 years after onset of illness. Therapies for managing MS include (1) treatment aimed at modification of the disease course, including treatment of acute exacerbation and directed to long-term suppression of the disease; (2) treatment of the symptoms of MS; (3) prevention and treatment of medical complications, and (4) management of secondary personal and social problems.

The onset of MS may be dramatic or so mild as to not cause a patient to seek medical attention. The most common symptoms include weakness in one or more limbs, visual blurring due to optic neuritis, sensory disturbances, diplopia and ataxia. The course of disease may be stratified into three general categories: (1) relapsing MS, (2) chronic progressive MS, and (3) inactive MS. Relapsing MS is characterized by recurrent attacks of neurologic dysfunction. MS attacks generally evolve over days to weeks and may be followed by complete, partial or no recovery. Recovery from attacks generally occurs within weeks to several months from the peak of symptoms, although rarely some recovery may continue for 2 or more years.

Chronic progressive MS results in gradually progressive worsening without periods of stabilization or remission. This form develops in patients with a prior history of relapsing MS, although in 20% of patients, no relapses can be recalled. Acute relapses also may occur during the progressive course.

A third form is inactive MS. Inactive MS is characterized by fixed neurologic deficits of variable magnitude. Most patients with inactive MS have an earlier history of relapsing MS.

Disease course is also dependent on the age of the patient. For example, favourable prognostic factors include early onset (excluding childhood), a relapsing course and little residual disability 5 years after onset. By contrast, poor prognosis is associated with a late age of onset (i.e., age 40 or older) and a progressive course. These variables are interdependent, since chronic progressive MS tends to begin at a later age that relapsing MS. Disability from chronic progressive MS is usually due to progressive paraplegia or quadriplegia (paralysis) in patients. In one aspect of the invention, patients will preferably be treated when the patient is in remission rather then in a relapsing stage of the disease.

Short-term use of either adrenocorticotropic hormone or oral corticosteroids (e.g., oral prednisone or intravenous methylprednisolone) is the only specific therapeutic measure for treating patients with acute exacerbation of MS.

Newer therapies for MS include treating the patient with interferon beta-1b, interferon beta-1a, and Copaxone® (formerly known as copolymer 1). These three drugs have been shown to significantly reduce the relapse rate of the disease. These drugs are self-administered intramuscularly or subcutaneously.

However, none of the current treatment modalities inhibit demyelination, let alone promotes or allows spontaneous remyelination or reduces paralysis. One aspect of the invention contemplates treating MS with agents disclosed herein either alone or in combination with other standard treatment modalities.

Congenital Metabolic Disorders

Congenital metabolic disorders include phenylketonuria (PKU) and other aminoacidurias, Tay-Sachs disease, Niemann-Pick disease, Gaucher's disease, Hurler's syndrome, Krabbe's disease and other leukodystrophies that impact the developing sheath as described more fully below.

PKU is an inherited error of metabolism caused by a deficiency in the enzyme phenylalanine hydroxylase. Loss of this enzyme results in mental retardation, organ damage, unusual posture and can, in cases of maternal PKU, severely compromise pregnancy. A model for studying PKU has been discovered in mice. Preferably infants identified with PKU are sustained on a phenylalanine free or lowered diet. An aspect of the invention would be to combine such diets with the compounds and compositions disclosed herein to prevent demyelination and remyelinate cells damaged due to PKU.

Classical Tay-Sachs disease appears in the subject at about age 6 months and will eventually result in the death of the subject by age 5 years. The disease is due to the lack of the enzyme, hexoaminidase A (hex A), which is necessary for degrading certain fatty substances in the brain and nerve cells. The substances in the absence of the enzyme accumulate and lead to the destruction of nerve cells. Another form of hex A enzyme deficiency occurs later in life and is referred to as juvenile, chronic and adult onset forms of hex A deficiency. Symptoms are similar to those that characterize classical Tay-Sachs disease. There is also an adult onset form of the enzyme deficiency. Currently there is no cure or treatment for the disease/deficiency, only the preventative measure of in utero testing of the fetus for the disease. Thus, the compounds and compositions disclosed herein may be useful in ameliorating or preventing the destruction of the cells.

Niemann-Pick disease falls into three categories: the acute infantile form, Type B is a less common, chronic, non-neurological form, and Type C is a biochemically and genetically distinct form of the disease. In a normal individual, cellular cholesterol is imported into lysosomes for processing, after which it is released. Cells taken from subjects with Niemann-Pick have been shown to be defective in releasing cholesterol from lysosomes. This leads to an excessive build-up of cholesterol inside lysosomes, causing processing errors. NPC1 was found to have known sterol-sensing regions similar to those in other proteins, which suggests it plays a role in regulating cholesterol traffic. No successful therapies have been identified for Types A and C forms of Neumann-Pick. For Type C, patients are recommended to follow a low-cholesterol diet. Thus, the compounds and compositions disclosed herein may be useful in ameliorating or preventing the destruction of the cells.

Gaucher's disease is an inherited illness caused by a gene mutation. Normally, this gene is responsible for an enzyme called glucocerebrosidase that the body needs to break down the fat, glucocerebroside. In patients with Gaucher's disease, the body is not able to properly produce this enzyme and the fat cannot be broken down. Like Tay-Sachs disease, Gaucher's disease is considerably more common in the descendants of Jewish people from Eastern Europe (Ashkenazi), although individuals from any ethnic group may be affected. Among the Ashkenazi Jewish population, Gaucher's disease is the most common genetic disorder, with an incidence of approximately 1 in 450 persons. In the general public, Gaucher's disease affects approximately 1 in 100,000 persons.

In 1991, enzyme replacement therapy became available as the first effective treatment for Gaucher's disease. The treatment consists of a modified form of the glucocerebrosidase enzyme given intravenously. It is contemplated that the compositions and compounds disclosed herein can be used alone or more preferably in combination with glycocerebrosidase administration to treat the disease in an afflicted subject.

Hurler's syndrome, also known as mucopolysaccharidosis type I, is a class of overlapping diseases. These genetic diseases share in common the cellular accumulation of mucopolysaccharides in fibroblasts. The diseases are genetically distinguishable. Fibroblast and bone marrow transplantation does not seem to be helpful, thus compounds and compositions useful in ameliorating disease severity and progression are needed. The compounds and compositions disclosed herein may be administered to a subject to ameliorate disease progression and/or severity.

Krabbe's disease (also known as Globoid cell leukodystrophy) is an autosomal recessive condition resulting from galactosylceramidase (or galactocerebrosidase) deficiency, a lysosomal enzyme that catabolises a major lipid component of myelin. Incidence in France is an estimated 1:150,000 births. The disease leads to demyelination of the central and peripheral nervous system. Onset generally occurs during the first year of life and the condition is rapidly progressive, but juvenile, adolescent or adult onset forms have also been reported, with a more variable rate of progression. Diagnosis is established from enzyme assay (galactosylceramidase deficiency). There are several natural animal models (mouse, dog, monkey). Krabbe's disease, like all leukodystrophies, has no known cures or effective treatments. One embodiment of the invention is to use the compositions and compounds disclosed herein to treat or ameliorate Krabbe's disease and other leukodystrophies.

Leukodystrophies are a group of genetically determined progressive disorders that affect the brain, spinal cord and peripheral nerves. They include adrenoleukodystrophy (ALD), adrenomyeloneuropathy (AMN), Aicardi-Goutiers syndrome, Alexander's disease, CACH (i.e., childhood ataxia with central nervous system hypomyelination or vanishing white matter disease), CADASIL (i.e., cerebral autosomal dominant arteriopathy with subcortical infarcts and leukoencephalopathy), Canavan disease (spongy degeneration), Cerebrotendinous Xanthomatosis (CTX), Krabbe's disease (discussed above), metachromatic leukodystrophy (MLD), neonatal adrenoleukodystrophy, ovarioleukodystrophy syndrome, Pelizaeus-Merzbacher disease (X-linked spastic paraplegia), Refsum disease, van der Knaap syndrome (vaculating leukodystrophy with subcortical cysts) and Zellweger syndrome. None of the diseases have effective treatments let alone cures. Consequently, means of treating or ameliorating the symptoms of the disease, such as by using the compositions and compounds disclosed herein, is needed.

Neuropathies with Abnormal Myelination

A variety of chronic immune polyneuropathies exist which result in demyelination in the patient. The age of onset for the conditions varies by condition. Standard treatments for these diseases exist and could be combined with the compositions and compounds disclosed herein. Alternatively, the compositions and compounds disclosed can be used alone. Existing standard therapies include the following:

TABLE IV

| Neuropathy | Clinical Features | Treatment |
|---|---|---|
| Chronic Immune Demyelinating Polyneuropathy (CIDP) | Onset between 1-80 years. Characterized by weakness, sensory loss, and nerve hypertrophy. | T-cell immunosuppression with prednisone, cyclosporine A or methotrexate, HIG, plasma exchange |
| Multifocal CIDP | Onset between 28 to 58 years and characterized by asymmetric weakness, sensory loss with a course that is slowly progressive or relapsing-remitting. | T cell immunosuppression with prednisone Human immunoglobulin (HIG) |
| Multifocal Motor Neuropathy (MMN) | Onset ranges from 25 to 70 years, with twice as many men as women. Features include weakness, muscle atrophy, fasciculations, and cramps which are progressive over 1-30 years. | HIG B cell immunosuppression with plasma exchange cyclophosphamide, Rituxan |
| Neuropathy with IgM binding to Myelin-Associated Glycoprotein (MAG) | Onset is usually over age 50 and is characterized by sensory loss (100%), weakness, gain disorder, tremor which is all slowly progressive. | B-cell immunosuppression plasma exchange cyclophosphamide Rituxan α-interferon cladribine or fludarabine prednisone |
| GALOP Syndrome (Gait disorder, Autoantibody, Late-age, Onset, Polyneuropathy) | A gait disorder with polyneuropathy | HIG Plasma exchange cyclophosphamide |
| POEMS Syndrome (Polyneuropathy, Organomegaly, Endocrinopathy, M-Protein and Skin changes) also known as Crow-Fukase Syndrome and Takatsuki disease | Onset occurs between 27 and 80 years with weakness, sensory loss, reduced or absent tendon reflexes, skin disorders and other features. | Osteosclerotic lesions are treated with irradiation. Widespread lesions with chemotherapy (Melphalan and prednisone). |

Drug and Radiation Induced Demyelination

Certain drugs and radiation can induce demyelination in subjects. Drugs that are responsible for demyelination include but are not limited to chloroquine, FK506, perhexiline, procainamide, and zimeldine.

Radiation also can induce demyelination. Central nervous system (CNS) toxicity due to radiation is believed to be cause by (1) damage to vessel structures, (2) deletion of oligodendrocyte-2 astrocyte progenitors and mature oligodendrocytes, (3) deletion of neural stem cell populations in the hippocampus, cerebellum and cortex, and generalized alterations of cytokine expression. Most radiation damage results from radiotherapies administered during the treatment of certain cancers. See for review Belka et al., 2001 Br. J. Cancer 85: 1233-9. However, radiation exposure may also be an issue for astronauts (Hopewell, 1994 Adv. Space Res. 14: 433-42) as well as in the event of exposure to radioactive substances.

Patients who have received drugs or been exposed accidentally or intentionally to radiation may experience a benefit by administered one of the compounds or compositions disclosed herein to prevent demyelination or to promote remyelination.

Conditions Involving Demyelination

Additional inherited syndromes/diseases that result in demyelination include Cockayne's syndrome, congenital hypomyelinating, Farber's disease, metachromatic leukodystrophy, Peliszaeus-Merzbacher disease, Refsum, prion related conditions and Salla disease.

Cockayne's syndrome (CS) is a rare inherited disorder in which people are sensitive to sunlight, have short stature and have the appearance of premature aging. In the classical form of Cockayne's syndrome (Type I), the symptoms are progressive and typically become apparent after the age of one year. An early onset or congenital form of Cockayne's syndrome (Type II) is apparent at birth. Interestingly, unlike other DNA repair diseases, Cockayne's syndrome is not linked to cancer. CS is a multi-system disorder that causes both profound growth failure of the soma and brain and progressive cachexia, retinal, cochlear, and neurologic degeneration, with a leukodystrophy and demyelinating neuropathy without an increase in cancer. After exposure to UV (e.g., sunlight), subjects with Cockayne's syndrome can no longer perform transcription-coupled repair. Two genes defective in Cockayne's syndrome, CSA and CSB, have been identified so far. The CSA gene is found on chromosome 5. Both genes code for proteins that interacts with components of the transcriptional machinery and with DNA repair proteins.

To date, no cures or effective treatments for patients with this disease have been identified. Thus, one aspect of the invention is treatment of this disease with the compounds and compositions disclosed herein.

Congenital hypomyelination has several names including congenital dysmyelinating neuropathy, congenital hypomyelinating polyneuropathy, congenital hypomyelination (Onion Bulb) polyneuropathy, congenital hypomyelination neuropathy, congenital neuropathy caused by hypomyelination, hypomyelination neuropathy and CHN. Hereditary peripheral neuropathies, among the most common genetic disorders in humans, are a complex, clinically and genetically heterogeneous group of disorders that produce progressive deterioration of the peripheral nerves. Congenital hypomyelination is one of a group of disorders. This group includes hereditary neuropathy with liability to pressure palsies, Charcot-Marie-Tooth disease, Dejerine-Sottas syndrome, and congenital hypomyelinating neuropathy. There are no known cures or effective treatments for any of these disorders.

Farber's disease has several names include: Farber lipogranulomatosis, ceremidase deficiency, acid ceramidase deficiency, AC deficiency, N-laurylsphingosine deacylase deficiency, and N-acylsphingosine amidohydrolase. As certain names reveal, the disease occurs due to a deficiency of acid ceramidase (also known as N-acylsphingosine amidohydrolase, ASAH). The lack of the enzyme results in an accumulation of non-sulfonated acid mucopolysaccharide in the neurons and glial cells. Patients with the disease usually die before the age of 2 years.

Metachromatic leukodystrophy (MLD) is a genetic disorder caused by a deficiency of the enzyme arylsulfatase A. It is one of a group of genetic disorders called the leukodystrophies that affect growth of the myelin sheath. There are three forms of MLD: late infantile, juvenile, and adult. In the late infantile form, which is the most common, onset of symptoms begins between ages 6 months and 2 years. The infant is usually normal at birth, but eventually loses previously gained abilities. Symptoms include hypotonia (low muscle tone), speech abnormalities, loss of mental abilities, blindness, rigidity (i.e., uncontrolled muscle tightness), convulsions, impaired swallowing, paralysis, and dementia. Symptoms of the juvenile form begin between ages 4 and 14, and include impaired school performance, mental deterioration, ataxia, seizures, and dementia. In the adult form, symptoms, which begin after age 16, may include impaired concentration, depression, psychiatric disturbances, ataxia, tremor, and dementia. Seizures may occur in the adult form, but are less common than in the other forms. In all three forms mental deterioration is usually the first sign.

Peliszaeus-Merzbacher disease (also known as perinatal sudanophilic leukodystrophy) is an X-linked genetic disorder that causes an abnormality of a proteolipid protein. The abnormality results in an infant's death typically before the age of one year. There are no known treatments or cures for the disease.

Refsum disease (also referred to as phytanic acid oxidase deficiency, heredopathia atactica polyneuritiformis or hereditary motor and sensory neuropathy IV, HMSN IV) is caused by mutations in the gene, which encodes phytanoyl-CoA hydroxylase (PAHX or PHYH). The major clinical features are retinitis pigmentosa, chronic polyneuropathy and cerebellar signs. Phytanic acid, an unusual branched chain fatty acid (3,7,11,15-tetramethyl-hexadecanoic acid) accumulates in the tissues and body fluids of patients with the disease and is unable to be metabolised due to the lack of PAHX. Plasmapheresis performed once or twice monthly effectively removes the acid from the body and permits liberalization of dietary restrictions limiting phytanic acid intake.

Prion related conditions include Gerstmann-Straussler disease (GSD), Creutzfeldt-Jakob disease (CJD), familial fatal insomnia and aberrant isoforms of the prion protein can act as infectious agents in these disorders as well as in kuru and scrapie (a disease found in sheep). The term prion derives from "protein infectious agent" (Prusiner, Science 216: 136-44, 1982). There is a proteolytic cleavage of the prion related protein (PRP) which results in an amyloidogenic peptide that polymerises into insoluble fibrils.

Salla disease and other types of sialurias are diseases involving problems with sialic acid storage. They are autosomal recessive neurodegenerative disorders that may present as a severe infantile form (i.e., ISSD) or as a slowly progressive adult form that is prevalent in Finland (i.e., Salla disease). The main symptoms are hypotonia, cerebellar ataxia and mental retardation. These conditions and diseases are also contemplated for palliative or ameliorating treatments.

Other conditions that result in demyelination include post-infectious encephalitis (also known as acute disseminated encephalomyelitis, ADEM), meningitis and injuries to the spinal cord. The compositions and compounds disclosed herein are also contemplated for use in treating these other demyelinating conditions.

Compound Preparation

The compounds of this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, Protecting Groups in Organic Synthesis, Second Edition, Wiley, N.Y., 1991, and references cited therein.

Furthermore, the compounds of this invention will typically contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of this invention, unless otherwise indicated. Pure stereoisomers (or enriched mixtures) may be prepared using, for example, optically active starting materials or stereoselective reagents well known in the art. Alternatively, racemic mixtures of such compounds can be separated using, for example, chiral column chromatography, chiral resolving agents and the like.

Compounds of formula I can be prepared using known synthetic procedures. Representative syntheses of compounds within the invention are presented below.

Compounds of formula II can be prepared by first coupling a protected 4-aminophenylalanine with 2-chloro-3-nitropyridine followed by reduction of the resulting coupled nitro compound. Cyclization of the resulting diaminopyridine with 1,1'-Carbonyldiimidazole (CDI) followed by alkylation of the resulting imidazolone affords compounds of formula II as exemplified in Scheme 1 below:

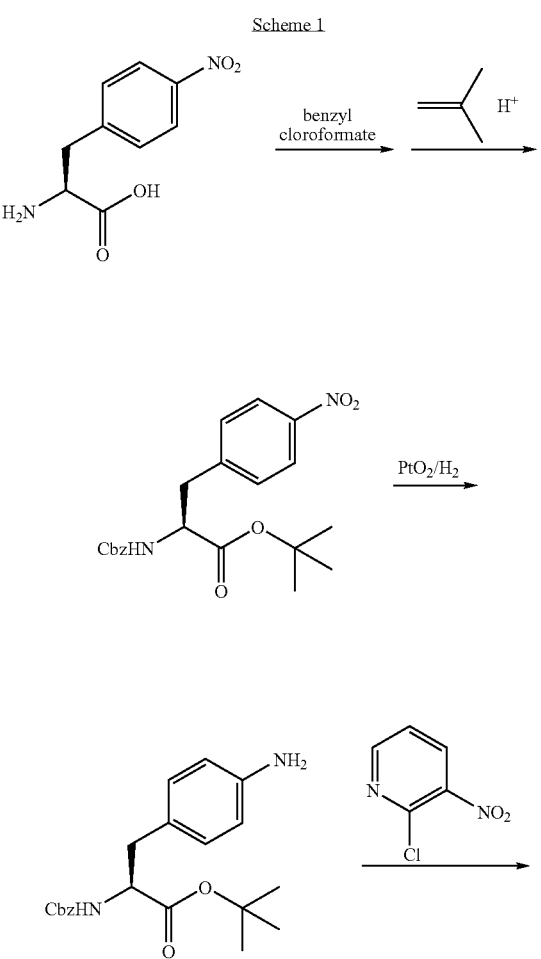

-continued

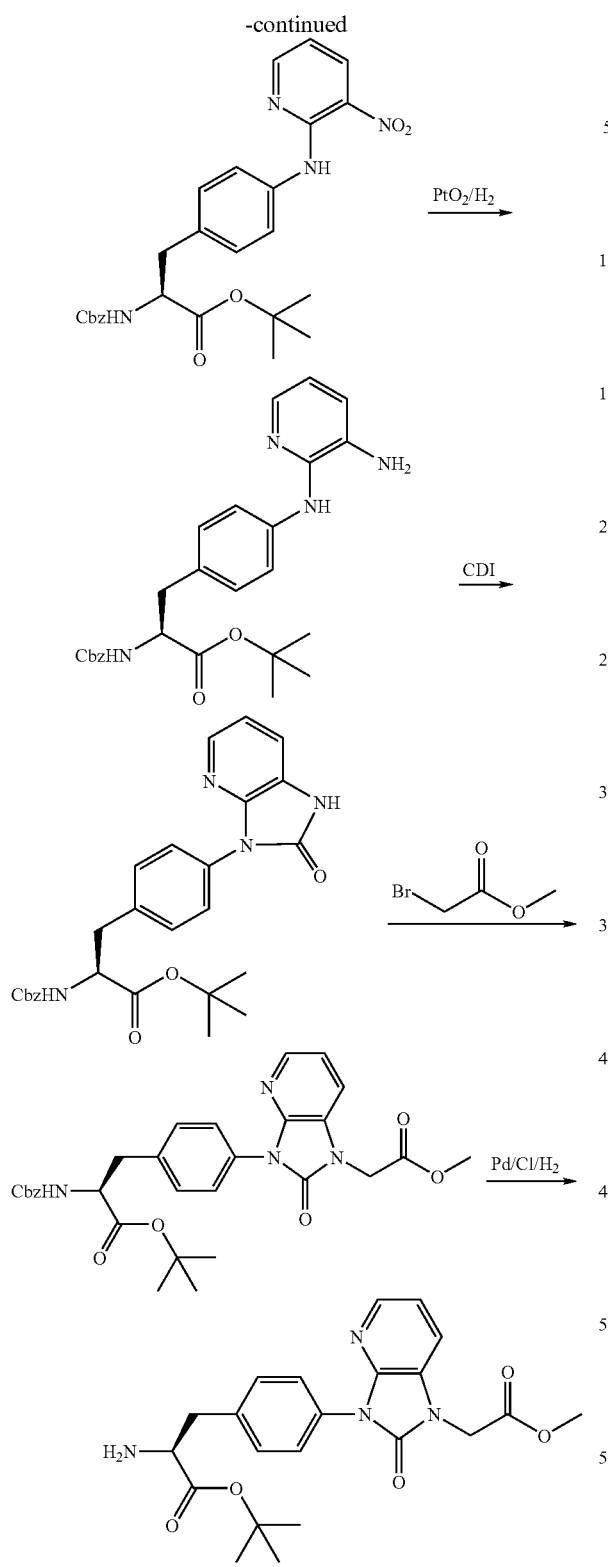

The resulting products can be recovered by conventional methods, such as chromatography, filtration, evaporation, crystallization, and the like or, alternatively, used without purification and/or isolation.

Compounds of formula III may be prepared by utilizing the aminoimidazalone product from Scheme 1 which can then coupled to substituted thiazolidinecarboxylic acids yielding compounds of formula III as exemplified in Scheme 2 below:

Scheme 2

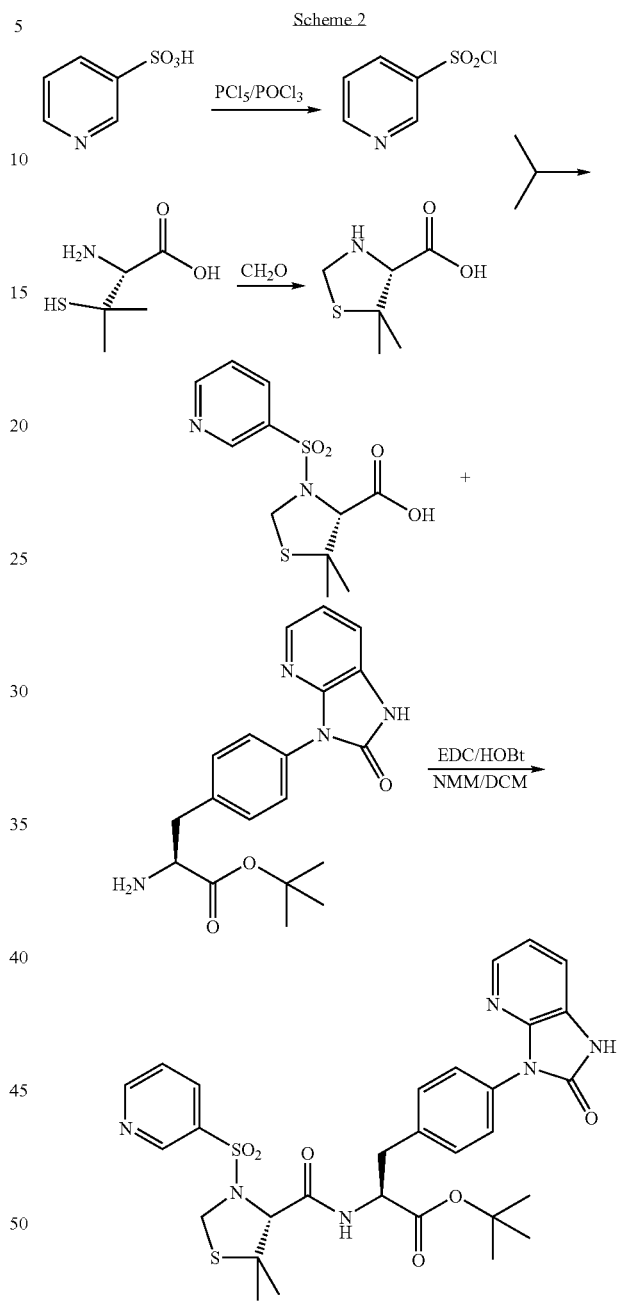

Additionally, an imidazolone nitrogen substituent, $R^6$, may be introduced prior to or after the coupling sequence employing standard alkylation reactions with standard alkylating reagents such as methyl iodide or methyl bromoacetate or by employing an appropriate coupling procedure. The resulting products can be recovered by conventional methods, such as chromatography, filtration, evaporation, crystallization, and the like or, alternatively, used in the without purification and/or isolation.

Compounds of formula IV, unsubstituted at the 2 position of the pyrimidine, may be prepared by coupling an imidazalone substituted phenylalanine derivative to an N,N-disubstituted 4-chloro-5-aminopyrimidine derived from 4,6- dichloro-5-aminopyrimidine and upon further elaboration of the coupled product, yields compounds of formula IV as exemplified in Scheme 3:

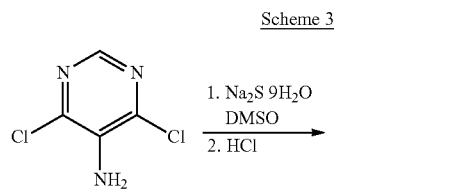
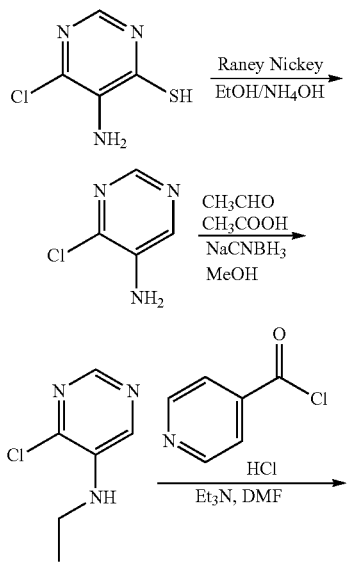
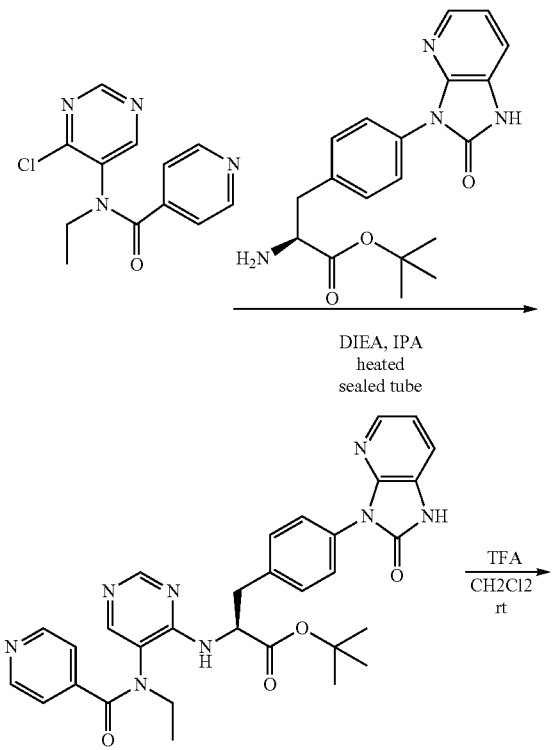

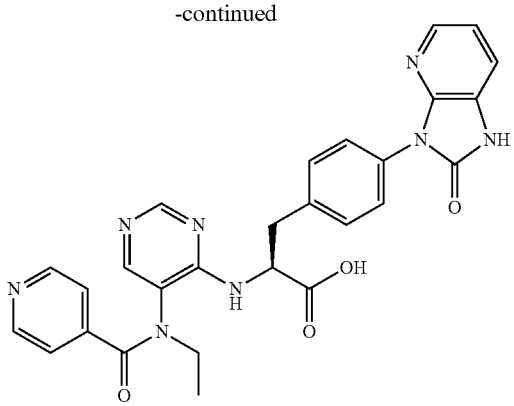

4,6-dichloro-5-aminopyrimidine is converted to a mecapto substituted 4-aminopyrimidine followed by Raney Nickel desulfurization. Introduction of an alkyl group by a reductive amination process followed by acylation with an acid chloride (or alternatively sulfonylation with a sulfonyl chloride) gives an N,N-disubstituted chloropyrimidine. Coupling with a phenylalanine derivative followed by hydrolysis of the ester affords the product.

Additionally, an imidazolone nitrogen substituent, $R^6$, may be introduced during the reaction sequence, if desired, employing standard alkylation reactions with standard alkylating reagents such as methyl iodide or methyl bromoacetate or by employing alcohols utilizing an appropriate coupling procedure.

Alternatively, compounds of formula IV, substituted at the 2 position of the pyrimidine, are prepared as shown in Scheme 4 below:

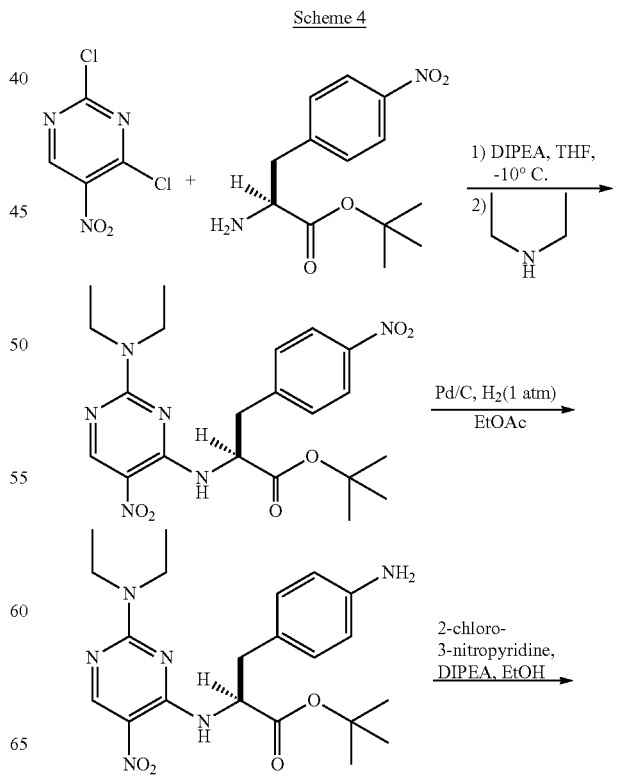

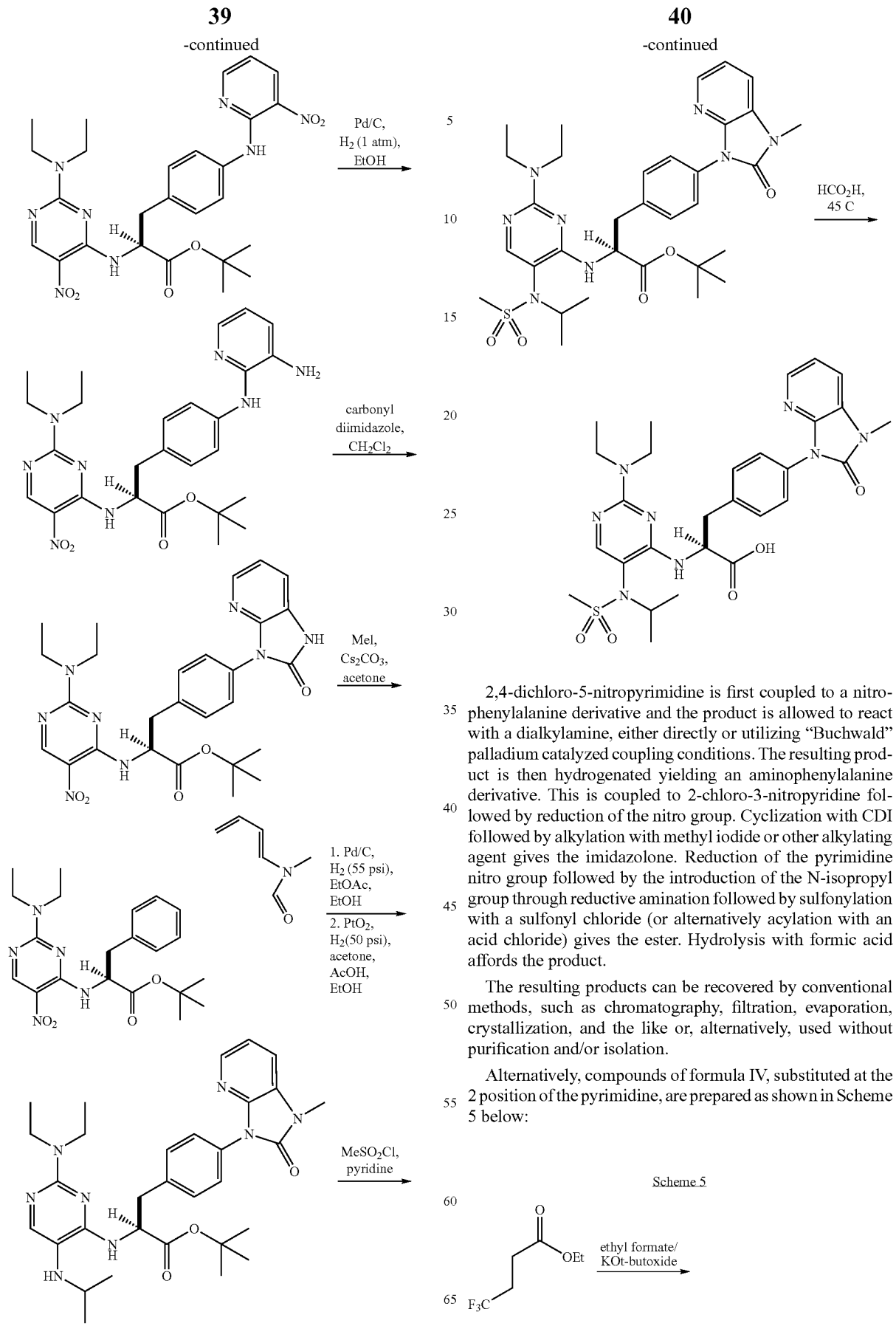

2,4-dichloro-5-nitropyrimidine is first coupled to a nitrophenylalanine derivative and the product is allowed to react with a dialkylamine, either directly or utilizing "Buchwald" palladium catalyzed coupling conditions. The resulting product is then hydrogenated yielding an aminophenylalanine derivative. This is coupled to 2-chloro-3-nitropyridine followed by reduction of the nitro group. Cyclization with CDI followed by alkylation with methyl iodide or other alkylating agent gives the imidazolone. Reduction of the pyrimidine nitro group followed by the introduction of the N-isopropyl group through reductive amination followed by sulfonylation with a sulfonyl chloride (or alternatively acylation with an acid chloride) gives the ester. Hydrolysis with formic acid affords the product.

The resulting products can be recovered by conventional methods, such as chromatography, filtration, evaporation, crystallization, and the like or, alternatively, used without purification and/or isolation.

Alternatively, compounds of formula IV, substituted at the 2 position of the pyrimidine, are prepared as shown in Scheme 5 below:

Scheme 5

-continued

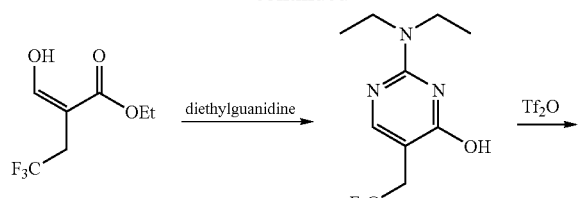
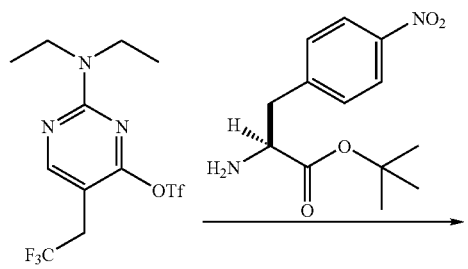
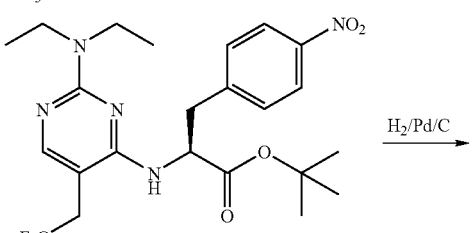
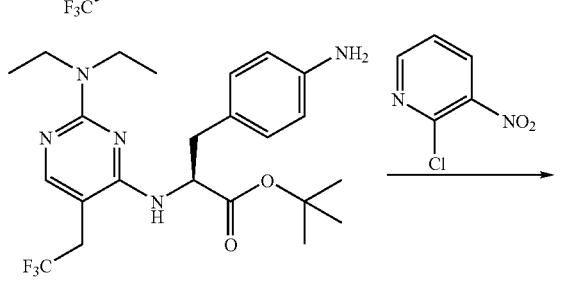
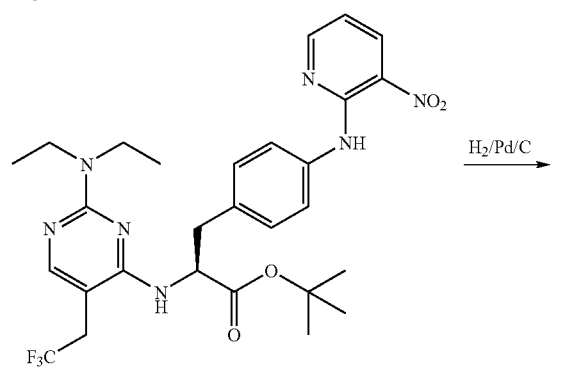
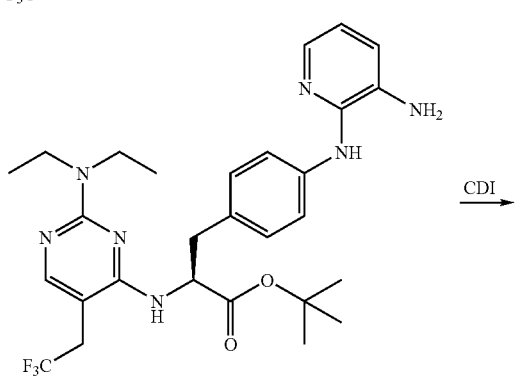

-continued

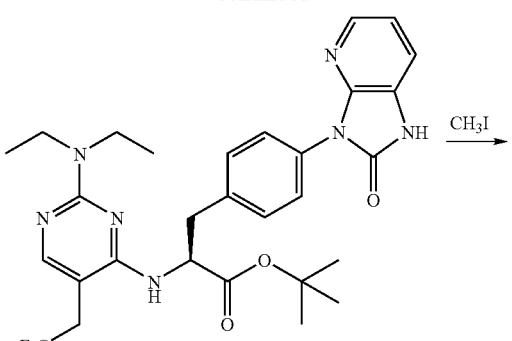
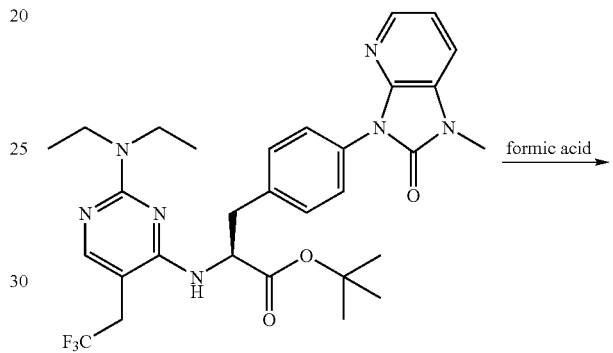
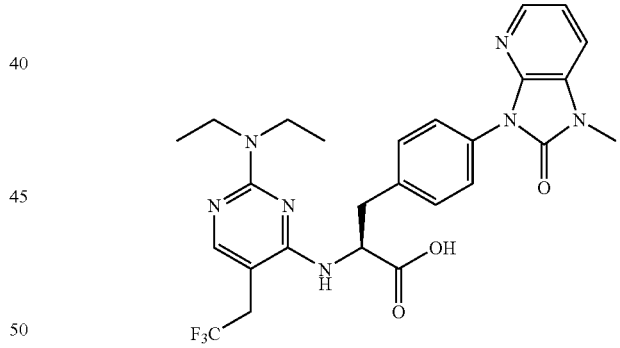

Ethyl formate is transformed into a substituted 4-hydroxypyrimidine which is then converted to a triflate. This is coupled to a nitrophenylalanine derivative and the resulting nitro product is reduced to the aminophenylalanine derivative. This is coupled to 2-chloro-3-nitropyridine followed by reduction of the nitro group. Cyclization with CDI followed by alkylation with methyl iodide or other alkylating agent gives the imidazolone. Hydrolysis with formic acid affords the product.

The resulting products can be recovered by conventional methods, such as chromatography, filtration, evaporation, crystallization, and the like or, alternatively, used without purification and/or isolation.

Compounds formula I prepared as described above are shown in TABLE I, Table II and Table III below:

TABLE I

Compounds prepared according to Scheme 1

II

| R⁵ | R⁶ | R¹³ |
|---|---|---|
| (CH₃)₃CO— | H— | PhCH₂OC(O)— |
| (CH₃)₃CO— | H— | H— |

TABLE II

Compounds prepared according Scheme 2

III

| R⁵ | R⁶ |
|---|---|
| HO— | CH₃OCH₂CH₂NHC(O)CH₂— |
| (CH₃)₃CO— | HOC(O)CH₂— |
| (CH₃)₃CO— | 4-NO₂PhOC(O)CH₂— |
| (CH₃)₃CO— | H— |
| HO— | H— |
| HO— | NH₂CH₂CH₂OCH₂CH₂OCH₂CH₂— |

TABLE III

Compounds prepared according Scheme 3, Scheme 4 and Scheme 5

IV

| R⁵ | R⁶ | R¹¹ | R¹² |
|---|---|---|---|
| HO— | CH₃— | (CH₃CH₂)₂N— | ((CH₃)₂CH) (CH₃SO₂)N— |
| HO— | CH₃— | (CH₃CH₂)₂N— | ((CH₃)₂CH) (CH₃C(O))N— |
| (CH₃)₃CO— | CH₃— | (CH₃CH₂)₂N— | NO₂— |
| HO— | CH₃— | (CH₃CH₂)₂N— | CF₃CH₂— |
| HO— | H— | H— | (Pyridin-4-yl)—C(O))(CH₃CH₂)N— |

The following synthetic and biological examples are offered to illustrate this invention and are not to be construed in any way as limiting the scope of this invention. Unless otherwise stated, all temperatures are in degrees Celsius.

EXAMPLES

In the examples below, the following abbreviations have the following meanings. If an abbreviation is not defined, it has its generally accepted meaning.

ACN=acetonitrile
bs=broad singlet
Boc=N-tert-butoxylcarbonyl
BOP=benzotriazol-1-yloxy-tris(dimethylamino)phosphonium hexafluorophosphate
Cbz=carbobenzyloxy
$CH_2Cl_2$=dichloromethane
d=doublet
dd=doublet of doublets
DCC=1,3-dicyclohexylcarbodiimide
DMAP=4-N,N-dimethylaminopyridine
EDC=1-(3-dimethylaminopropyl)-3-ethylcarbodiimide hydrochloride
$Et_3N$=triethylamine
FmocONSu=N-(9-fluorenylmethoxycarbonyl)succinimide
g=grams
h and hr=hour
$H_2O$=water
HOBT=1-hydroxybenzotriazole hydrate
HPLC=High performance (or pressure) liquid chromatography
kq=kilogram
$K_2CO_3$=potassium carbonate
kDa=kilodalton
L=liter
m=multiplet
MeOH=methanol
M=Molar
mg=milligram
min=minute mL=milliliter
mm=millimeter
mM=millimolar
mmol=millimol
N=normal
NaHCO$_3$=sodium bicarbonate
nM=nanomolar
q=quartet
s=singlet
sat.=saturated
t=triplet
t-BuOH=tert-butanol
TFA=trifluoroacetic acid
TLC or tlc=thin layer chromatography
Ts=tosyl
TsCl=tosyl chloride
TsOH=tosylate
μL=microliter
μg=microgram
μm=micron or micrometer Scheme 5 outlines reaction sequences that illustrate methods that may be used to prepare the compounds of this invention. Scheme 5 also illustrates the relationship of intermediates common to the products shown in tables 1 thru 3. The methods outlined in Schemes 1 thru 5 above and Scheme 6 below are general and illustrative and the invention is not limited to the use of these exact reaction sequences and methods.

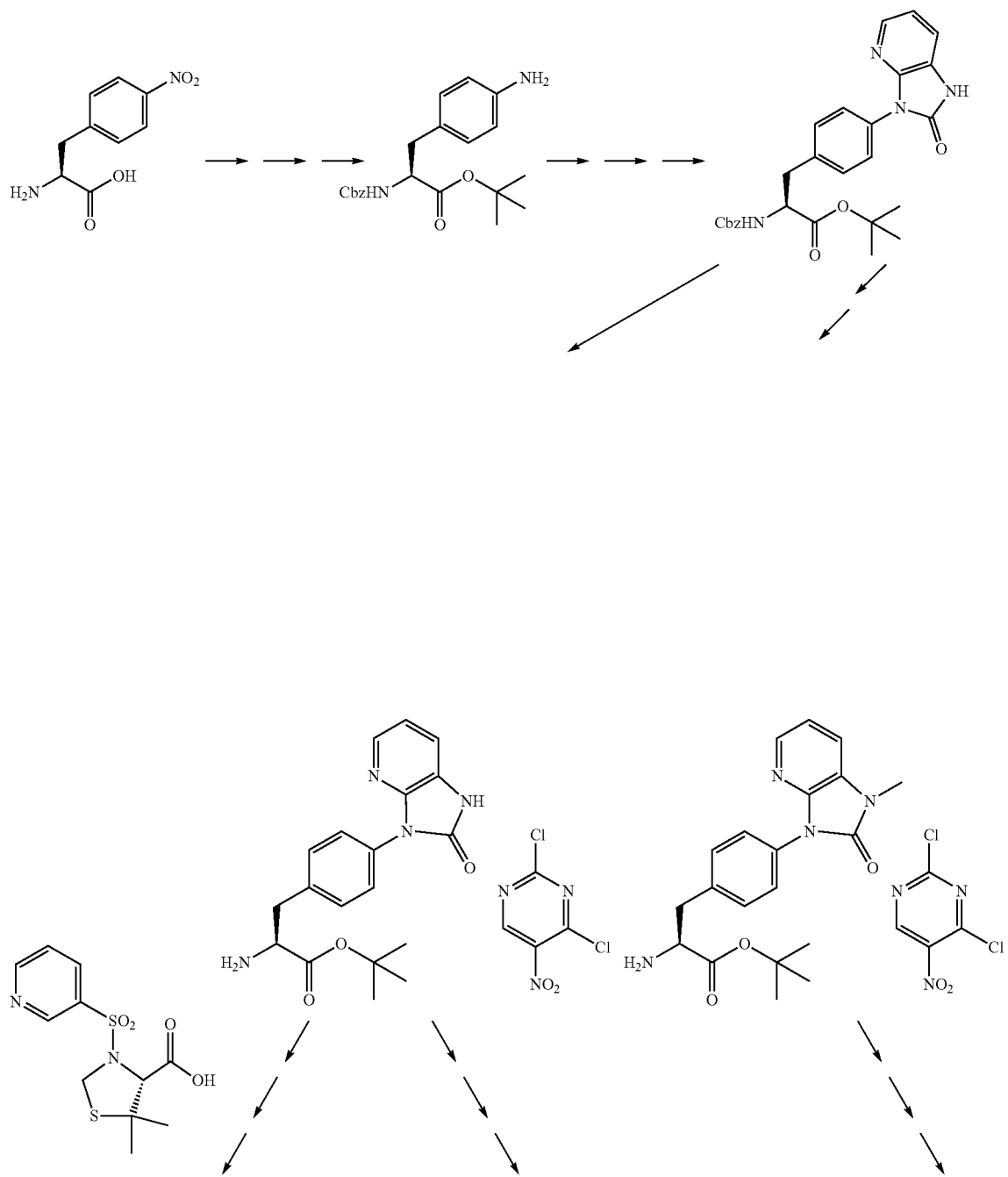

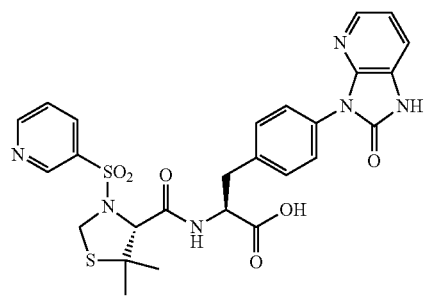
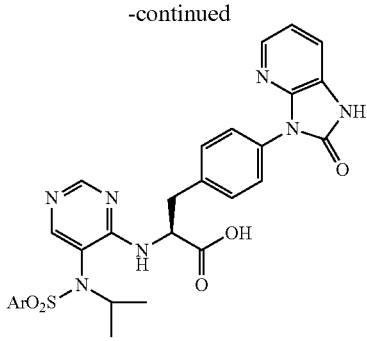
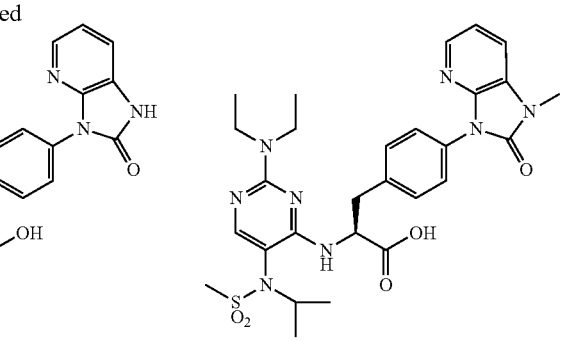

The following Examples describe methods for preparing the compounds shown in Schemes 1 thru 5 above.

Example 1

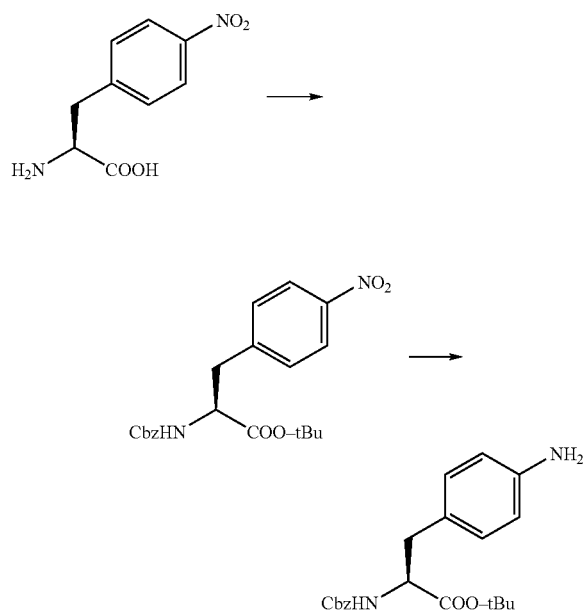

Sodium hydroxide (10 g, 0.25 m) is dissolved in water (300 ml). To this solution 4-nitrophenylalanine (50.3 g, 0.22 m) is added and stirred until complete dissolution. To the resulting solution the sodium carbonate (28.8 g, 0.26 m) is added and stirred suspension is cooled in an ice bath to +8° C. Benzyl chloroformate (44.7 g, 0.26 m) is added dropwise with vigorous stirring, maintaining internal temperature in +6° to +9° C. range. The mixture is stirred at +6° C. for additional 1 hr, transferred to the separatory funnel and washed with ether (2×150 ml). Aqueous phase is placed in a large Erlenmeyer flask (2 L) and is cautiously acidified with dil. aq. HCl to pH=2 and extracted with ethyl acetate (4×500 ml). The combined extracts are washed with water and dried with MgSO4. The solution is filtered and filtrate evaporated, residue is dissolved in ethyl acetate (150 ml) and diluted with hexane (500 ml). Crystalline material is filtered off and rinsed with cold solvent, air dried to give Cbz-4-nitrophenylalanine, 75 g (99.5% yield). $^1$H-NMR, DMSO-d6, (δ): 12.85 (bs, 1H), 8.12 (d, 2H, J=9 Hz), 7.52 (d, 2H, J=9 Hz), 7.30 (m, 5H), 4.95 (s, 2H), 4.28 (m, 1H), 3.32 (bs, 1H), 3.10 (m, 2H). $^{13}$C-NMR (δ): 173.1, 156.3, 146.6, 137.3, 130.8, 128.5, 128.0, 127.8, 123.5, 65.6, 55.1, 36.6. MS (m/z): 367.1 [M+23].

The Cbz-4-nitrophenylalanine (75 g, 0.22 m) is dissolved in dioxane (300 ml). The resulted stirred solution is cooled in Dry Ice bath to −20° C. (internal). The liquefied isobutylene (approx. 290 ml) is added followed by conc. sulfuric acid (35 ml) added in three equal portions, 30 min apart. The addition of acid is a very exothermic process, accompanied by substantial degree of polymerization. Efficient mechanical stirring is essential at this stage. Resulted mixture is stirred for 20 hr, allowing to warm up to ambient temperature then is cautiously poured into sat. aq. sodium carbonate solution (2 L) and diluted with ethyl acetate (600 ml). Organic layer is separated and aqueous layer is extracted with ethyl acetate (2×200 ml). Combined extracts are washed with water and dried with sodium sulfate. The solution is filtered and evaporated to dryness. The residue is taken up in ethyl acetate/hexane mixture (500 ml; 1:1) and filtered through plug of silica gel (ca. 2×2 in). The silica is rinsed with an additional amount of the same solvent (2 L total) and the filtrates are evaporated to give fully protected 4-nitrophenylalanine as a viscous oil, 73 g (83% after two steps). $^1$H-NMR, CDCl$_3$, (δ): 8.12 (d, 2H, J=8.4 Hz), 7.36 (m, 7H), 5.35 (m, 1H), 5.10 (m, 2H), 4.57 (m, 1H), 3.31 (m, 2H), 1.43 (s, 9H). $^{13}$C-NMR, CDCl$_3$, (δ): 169.7, 155.3, 146.9, 143.9, 136.0, 130.2, 128.4, 128.2, 128.0, 123.3, 82.9, 66.9, 54.7, 38.2, 31.4, 27.8, 13.9. MS (m/z): 423.1 [M+23].

Protected 4-nitrophenylalanine (73 g, 0.18 m) is dissolved in ethanol (500 ml) and platinum oxide catalyst (1.5 g) is added. The resulting solution is vigorously stirred in hydrogen atmosphere (50-60 psi) at ambient temperature until further hydrogen adsorption ceased (3 hr). The catalyst is filtered off and the filtrate is evaporated to dryness, the residue is taken up in ethyl acetate (200 ml) and filtered through plug of silica gel (2×2 in) using ethyl acetate-hexane mixture (3:2, 2 L) to rinse silica. The filtrate is concentrated to approx. 200 ml and hexane (500 ml) is added. The crystalline product is filtered off, rinsed with cold solvent and air-dried. Yield ~56 g, 84%. $^1$H-NMR, CDCl$_3$, (δ): 7.30 (bs, 5H), 6.92 (d, 2H, J=8.1 Hz), 6.58 (d, 2H, J=8.1 Hz), 5.21 (m, 1H), 5.10 (d, 2H, J=2.1 Hz), 4.46 (m, 1H), 3.59 (bs, 2H), 2.97 (s, 2H, J=5.4 Hz), 1.42 (s, 9H). $^{13}$C-NMR, CDCl$_3$, (δ): 170.6, 145.1, 136.3, 130.2, 128.3, 127.9, 125.6, 115.0, 81.9, 66.6, 55.2, 37.4, 27.8 MS (m/z): 393.1 [M+23].

Example 2

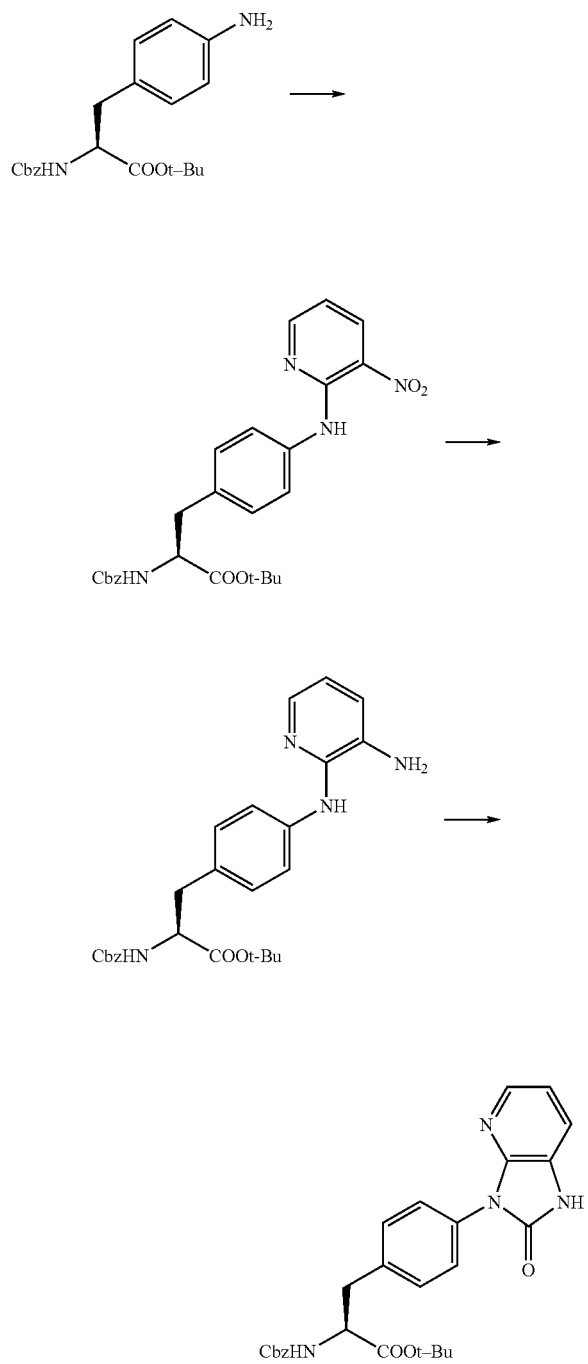

The product of Example 1, 4-aminophenylalanine, (20 g, 0.054 m) was dissolved in ethanol (200 ml) and treated with Hunig's base (21 g, 0.162 m, 3 eq) and 2-chloro-3-nitropyridine (10.3 g, 0.65 m, 1.2 eq). Resulted solution was stirred under nitrogen atmosphere and heated to reflux for 24 hr. LC analysis indicated presence of small amount of unreacted amine. The small additional amount of chloronitropyridine (1.1 g, 0.13 eq) was added and reflux continued for another 24 hr. Reaction mixture was cooled and evaporated to dryness. Residue was dissolved in ethyl acetate (600 ml) and obtained solution was washed with water (1×200 ml), dil. aq. citric acid (0.2 N, 2×200 ml), brine (1×200 ml) and dried with sodium sulfate. Solids were filtered off and filtrate evaporated to give 37 g of deep-red oil, containing expected product contaminated with excess of chloronitropyridine. Impure product was purified by flash chromatography (Biotage 75 L system) eluting with ethyl acetate:hexane (3:17) mixture. Fractions containing pure product were combined and evaporated to give deep-red, viscous oil, 26 g (99%). $^1$H-NMR, CDCl$_3$, (δ): 10.10 (s, 1H), 8.49 (m, 2H), 7.57 (d, 2H, J=9 Hz), 7.35 (bs, 5H), 7.19 (d, 2H, J=9 Hz), 6.84 (m, 1H), 5.30 (m, 1H), 5.13 (d, 2H, J=3 Hz), 4.57 (m, 1H), 3.11 (m, 2H), 1.45 (s, 9H). $^{13}$C-NMR, CDCl$_3$, (δ): 170.4, 155.5, 155.1, 150.0, 136.7, 136.3, 135.4, 132.4, 129.9, 128.5, 128.3, 128.0, 127.9, 122.2, 113.7, 82.2, 66.7, 55.1, 37.7, 27.8, 20.9. MS (m/z): 493.1 [M+1], 515.1 [M+23].

The red nitro compound (26 g, 0.054 m) was dissolved in THF (350 ml) and platinum oxide catalyst (1.35 g) was added. Resulted mixture was vigorously stirred under hydrogen atmosphere (50-60 psi) until hydrogen adsorption ceased (2 hr). Catalyst was filtered off and filtrate evaporated to dryness. Residue was dissolved in ethyl acetate (100 ml) and diluted with hexane (50 ml) till beginning of crystallization. Mixture was further diluted with ethyl acetate/hexane (1:1) mixture (300 ml) and was left standing in refrigerator for 3 hr. Crystalline solids were filtered off, rinsed with cold solvent and air-dried to give product, 23 g, 94%. $^1$H-NMR, CDCl$_3$, (δ): 7.81 (dd, 1H, J1=1.5 Hz, J2=4.8 Hz), 7.33 (bs, 5H), 7.17 (d, 2H, J=8.4 Hz), 7.03 (d, 2H, J=8.4 Hz), 6.96 (dd, 1H, J1=1.5 Hz, J2=7.5 Hz), 6.75 (dd, 1H, J1=5.0 Hz, J2=7.7 Hz), 6.22 (s, 1H), 5.31 (m, 1H), 5.09 (bs, 2H), 4.50 (m, 1H), 3.41 (bs, 2H), 3.02 (m, 2H), 1.43 (s, 9H). $^{13}$C-NMR, CDCl$_3$, (δ): 170.6, 155.6, 145.5, 140.21, 138.8, 136.3, 130.8, 129.9, 128.5, 128.3, 127.9, 123.4, 118.2, 117.0, 82.0, 66.6, 55.2, 37.4, 27.9. MS (m/z): 407.1 [M−56], 463.1 [M+1], 485.1 [M+23].

The aminopyridine (19 g, 0.041 m) was suspended in dichloromethane (200 ml) and CDI (12 g, 0.074 m, 1.8 eq) was added. Resulted mixture was stirred at ambient temperature for 20 hr. Reaction mixture was washed with sat. aq. bicarbonate (2×100 ml), brine (1×100 ml) and dried with sodium sulfate. Solids were filtered off and filtrate evaporated to dryness. Residue was dissolved in ethyl acetate (hot, 300 ml) and set to crystallize. Crystalline product was filtered off, rinsed with cold ethyl acetate and air-dried to give 19.9 g, 81% of the imidazolone. $^1$H-NMR, CDCl$_3$, (δ): 10.63 (s, 1H), 8.06 (d, 1H, J=3 Hz), 7.66 (d, 2H, J=9 Hz), 7.32 (m, 8H), 7.05 (m, 1H), 5.36 (m, 1H), 5.13 (s, 2H), 4.59 (m, 1H), 3.17 (m, 2H), 1.45 (s, 9H). $^{13}$C-NMR, CDCl$_3$, (δ): 170.4, 155.6, 154.3, 143.8, 141.0, 136.2, 135.8, 131.8, 130.2, 128.3, 128.0, 125.9, 122.2, 118.3, 116.0, 82.4, 66.8, 55.0, 37.7, 27.8. MS (m/z): 433.1 [M−56], 489.2 [M+1], 511.2 [M+23].

Example 3

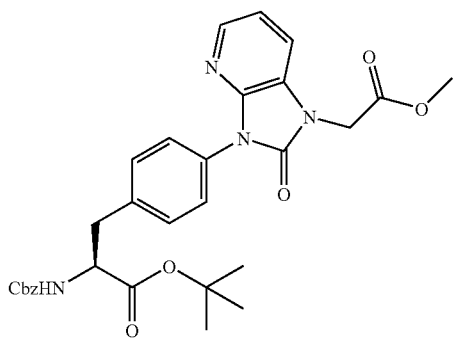

To a solution of the product of Example 2 (4.0 g, 8.19 mmol) in DMF (40 ml) crushed potassium carbonate (1.58 g, 11.47 mmol) was added followed by the addition of methyl bromoacetate (1.0 ml, 11.47 mmol). The reaction mixture was stirred under nitrogen at room temperature over night. The reaction mixture was concentrated in vacuo and the residue was taken up in ethyl acetate (100 ml). The organic phase was washed with $H_2O$, brine, dried over $Na_2SO_4$, filtered, and concentrated in vacuo. The crude material was purified by column chromatography (100% ethyl acetate) to yield 4.5 g (100%) of the title compound as a white foam. $R_f$=0.42 (5% $MeOH/CH_2Cl_2$). MS m/z=561, (M+H)$^+$. $^1H$ NMR (CDCl$_3$) δ 8.10-8.08 (d, 1H), δ 7.67-7.65 (d, 2H), δ 7.37-7.30 (m, 7H), δ 7.20-7.17 (m, 1H), δ 7.10-7.05 (m, 1H), δ 5.30-5.27 (d, 1H), δ 5.11 (s, 2H), δ 4.58-4.55 (q, 1H), δ 3.81 (s, 3H), δ 3.16-3.14 (d, 2H), δ 1.42 (s, 9H).

Example 4

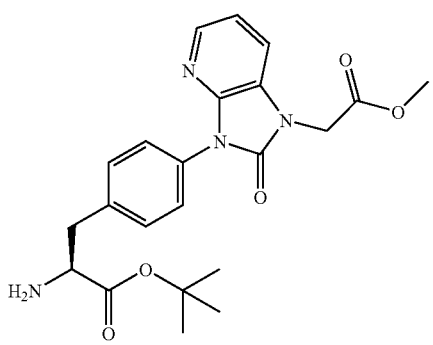

A solution of the product of Example 3 (2.25 g, 4.01 mmol) in MeOH (20 ml) with Degussa Pd/C catalyst (113 mgs) was placed under $H_2$ (55 psi) over night. The reaction mixture was filtered through Celite and concentrated in vacuo to yield 1.65 g (97%) of the title compound as a brown oil. $R_f$=0.32 (5% $MeOH/CH_2Cl_2$). MS m/z=449, (M+Na)$^+$. $^1H$ NMR (CDCl$_3$) δ 8.11-8.09 (d, 1H), δ 7.68-7.65 (d, 2H), δ 7.41-7.38 (d, 2H), δ 7.20-7.17 (m, 1H), δ 7.10-7.06 (m, 1H), δ 4.73 (s, 2H), δ 3.81 (s, 3H), δ 3.67-3.62 (m, 1H), δ 3.16-3.09 (m, 1H), δ 2.91-2.84 (m, 1H), δ 1.46 (s, 9H).

Example 5

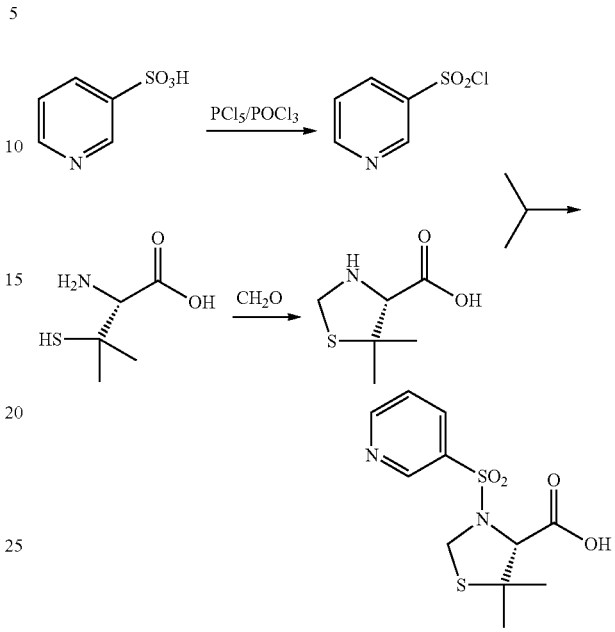

Pyridine-3-sulfonic acid (125 g, 0.78 m) was placed in a 1 L, 3-necked flask equipped with mechanical stirrer, reflux condenser, thermometer and nitrogen inlet. Next, the phosphorus pentachloride (250 g, 1.19 m, 1.5 eq) was added, followed immediately by the phosphorus oxychloride (330 ml, 3.8 m, 4.5 eq). The contents of flask were initially stirred at ambient temperature for 30 min, then brought slowly to gentle reflux (internal temp. approx. 110° C.) over the next hour, kept at this temperature for approx. 3.5 hr then allowed over the next 12 hr to cool back to ambient temperature. Gas evolution was observed during this time. The volatiles were stripped under reduced pressure (at 12 mmHg/40° C.) and yellow semi-solid residue was diluted with DCM (1 L). The slurry was poured slowly into the stirred, ice-cold sat. aq. bicarbonate, maintaining pH=7. Gas evolution was observed. The organic layer was separated and aqueous layer was back-extracted with DCM. The combined extracts were washed with cold sat. aq. bicarbonate, brine and dried with magnesium sulfate. The solids were filtered off and filtrate evaporated, leaving pyridine-3-sulfonyl chloride as a pale yellow, oily liquid, 123 g (93% pure; 88% theory). $^1H$-NMR, CDCl$_3$, (δ): 9.26 (d, 1H), 8.98 (dd, 1H), 8.34 (m, 1H), 7.62 (m, 1H). $^{13}C$-NMR, CDCl$_3$, (δ): 155.3, 147.4, 140.9, 134.6, 124.2.
MS (m/z): 178.0 [M+1].

L-penicillamine (150 g, 1.0 m) was dissolved with stirring in DI water (1500 ml), cooled in ice-bath to +8° C. and treated with formalin (150 ml, 37% aq.). The reaction mixture was stirred at +8° C. for 2 hr, then cooling bath was removed and stirring continued for 12 hr. The clear solution was concentrated under reduced pressure (14 mmHg/50°) leaving white residue. The solids were re-suspended, then dissolved in hot MeOH (2500 ml) and left standing at ambient temperature for 12 hr. The white, fluffy precipitate was filtered off and rinsed with cold methanol. The filtrate was concentrated and set to crystallize again. The collected precipitate was combined with the first crop and dried in vacuum oven for 24 hr at 55° C. at 45 mmHg. The yield of (R)-5,5-dimethylthiazolidine-4-carboxylic acid was 138 g (>99% pure; 86% theory).

¹H-NMR, DMSO-d6, (δ): 4.25 (d, 1H), 4.05 (d, 1H), 3.33 (s, 1H), 1.57 (s, 3H), 1.19 (s, 3H). ¹³C-NMR, DMSO-d6, (δ): 170.8, 74.4, 57.6, 51.8, 28.9, 27.9. MS (m/z): 162.3 [M+1].

In a 4 L reactor equipped with mechanical stirrer and thermometer, a buffer solution was prepared from potassium monobasic phosphate (43 g, 0.31 m) and potassium dibasic phosphate (188.7 g, 1.08 m) in DI water (2 L). The (R)-5,5-dimethylthiazolidine-4-carboxylic acid (107 g, 0.675 m) was added and stirred until complete dissolution. The solution was cooled in an ice-bath to +8° C. A separately prepared solution of pyridine-3-sulfonyl chloride (124 g, 0.695 m) in DCM (125 ml) was added dropwise to the reactor with vigorous stirring over the 1 hr. The pH of reaction mixture was monitored and after 4 hr, found to be pH=5 and adjusted to pH=6 by addition of solid bicarbonate. The mixture was allowed to warm up to ambient temperature over 18 hr. The pH was adjusted to 2 with dil. aq. sulfuric acid, stirred for 1 hr and precipitated yellow solids were filtered off, rinsed with water to neutral. The solid cake was transferred into 2 L Erlenmayer flask, suspended in DCM (500 ml) with occasional swirling for 5 min and filtered off again. The filter cake was washed with DCM and air-dried. The yield of the title compound, (R)-5,5-dimethyl-3-(pyridin-3-ylsulfonyl)thiazolidine-4-carboxylic acid was 148.9 g (98% pure; 73% theory). ¹H-NMR, DMSO-d6, (δ): 9.05 (d, 1H), 8.89 (m, 1H), 8.32 (m, 1H), 7.69 (m, 1H), 4.68 (q, 2H), 4.14 (s, 1H), 1.35 (s, 3H), 1.29 (s, 3H). ¹³C-NMR, DMSO-d6, (δ): 170.0, 154.3, 147.9, 135.8, 134.1, 124.8, 72.6, 54.3, 50.2, 29.4, 25.0. MS (m/z): 303.2 [M+1].

Example 6

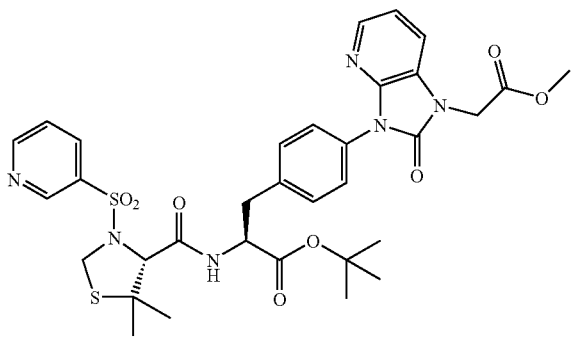

To a solution of the product of Example 4 (1.65 g, 3.88 mmol) in acetonitrile (35 ml) was added the product of Example 5 (1.06 g, 3.53 mmol), HATU (1.75 g, 3.88 mmol), and triethylamine (5.3 ml). The homogeneous brown solution was stirred under nitrogen for 72 hours. The organic reaction mixture was concentrated in vacuo, taken up in ethyl acetate (40 ml), washed with 1N HCl, sat. NaHCO₃, and brine. The organic layer was dried over Na₂SO₄, filtered, and concentrated in vacuo to yield 2.67 g (97%) 3 as an orange foam. $R_f$=0.36 (5% MeOH/CH₂Cl₂). MS m/z=711, (M+H)⁺. ¹H NMR (CDCl₃) δ 9.09-9.08 (d, 1H), δ 8.86-8.84 (m, 1H), δ 8.18-8.15 (m, 1H), δ 8.07-8.05 (m, 1H), δ 7.66-7.63 (d, 2H), δ 7.52-7.48 (m, 1H), δ 7.41-7.38 (d, 2H), δ 7.19-7.16 (m, 1H), δ 7.08-7.04 (m, 1H), δ 6.93-6.90 (d, 1H), δ 4.83-4.76 (q, 1H), δ 4.71 (s, 2H), δ 4.62-4.59 (d, 1H), δ 4.49-4.46 (d, 1H), δ 3.91 (s, 1H), δ 3.80 (s, 3H), δ 3.22-3.08 (m, 2H), δ 1.46 (s, 9H), δ 1.20-1.17 (d, 6H).

Example 7

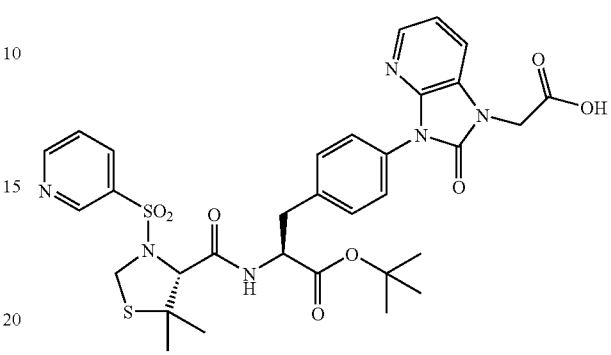

To a solution of the product of Example 6 (2.67 g, 3.75 mmol) in THF (12 ml) was added a solution of LiOH.H₂O (245 mgs, 5.97 mmol) in H₂O (3 ml). The reaction mixture was stirred at room temperature over night under nitrogen. Upon completion the reaction mixture was concentrated in vacuo, dissolved in H₂O (100 ml), and acidified to pH 4 with a 1M HCl solution. The desired product precipitated out as a white solid and was filtered and rinsed with H₂O to yield 1.87 g (72%) of the title compound. MS m/z=697, (M+H)⁺. ¹H NMR (CD₃OD) δ 9.02 (s, 1H), δ 9.80 (s, 1H), δ 8.47-8.44 (d, 1H), δ 8.21-8.19 (d, 1H), δ 7.98-7.96 (d, 1H), δ 7.63-7.59 (m, 3H), δ 7.52-7.48 (m, 3H), δ 7.17-7.13 (m, 1H), δ 4.75 (s, 2H), δ 4.72-4.61 (m, 3H), δ 4.14 (s, 1H), δ 3.22-3.16 (m, 2H), δ 1.45 (s, 9H), δ 1.25-1.19 (d, 6H). ¹³C NMR (CD₃OD) δ 169.9, 169.5, 168.9, 153.1, 152.8, 147.5, 142.8, 140.2, 136.6, 135.8, 134.0, 131.7, 129.9, 126.0, 124.2, 123.9, 117.8, 114.9, 81.8, 72.6, 54.1, 49.9, 41.3, 36.4, 28.5, 26.6, 23.4.

Example 8

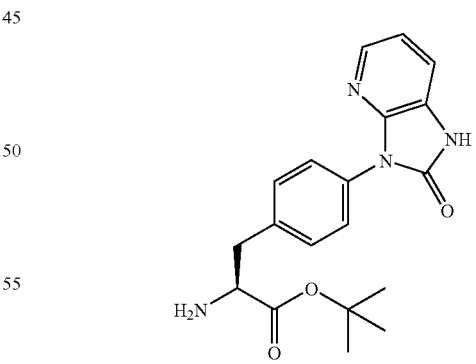

The product of Example 2 (52 g, 0.106 m) was slurried in MeOH (450 ml), hydrogenation catalyst (8.7 g, 5% Pd/C, Degussa) was added and the mixture was stirred under the hydrogen atmosphere (60 psi) until further absorption ceased (ca. 2 hrs). THF (150 ml) was added to dissolve precipitated solids and the solution was filtered through plug of Celite, using DCM to rinse the filter. The filtrate was evaporated to dryness, re-dissolved in DCM (300 ml) and stripped again.

This operation was repeated twice. The foamy solids were kept under high vacuum for 3 hrs. The yield of title compound was 38.3 g (101% of theory). $^1$H-NMR, CDCl$_3$, (δ): 8.08 (m, 1H), 7.56 (AB q, 4H) 7.37 (m, 1H), 7.06 (m, 1H), 3.68 (m, 1H), 2.03 (m, 2H), 1.49 (s, 9H). $^{13}$C-NMR, CDCl$_3$, (δ): 173.8, 154.6, 143.9, 141.0, 137.4, 131.5, 130.2, 126.1, 122.3, 118.0, 116.1, 81.4, 56.0, 40.6, 27.9. MS (m/z): 299.3 [M−56], 355.4 [M+1], 377.4 [M+23].

Example 9

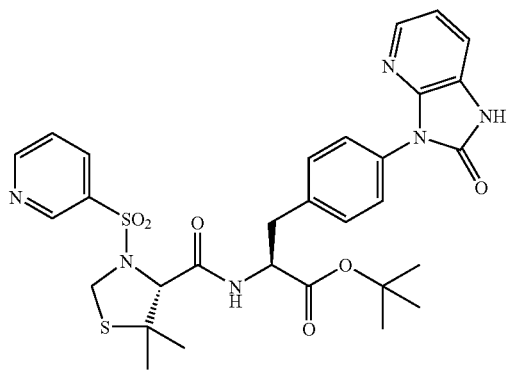

The product of Example 8 (38.3 g, assume 0.106 m) was dissolved in DCM (500 ml) and treated successively with: N-methylmorpholine (27 g, 30 ml, 0.266 m; 2.5 eq), HOBt (17.3 g, 0.128 m; 1.2 eq), and the product of Example 5 (33.8 g, 0.112 m; 1.06 eq). The resulting non-homogenous solution was cooled in an ice-bath to +4° C. and treated with EDC (22.5 g, 0.117 m; 1.1 eq) in one portion. The reaction mixture was stirred, allowing it to warm up to ambient temperature over the next 4 hr and then for 18 hr more. The solvent was stripped and residue dissolved in ethyl acetate (1.2 L), washed with sat. aq. bicarbonate (2×250 ml), water (250 ml), brine (300 ml) and dried with magnesium sulfate. The solution was filtered and evaporated to dryness, leaving a light orange, viscous oil, 76 g (>>100%). The crude product was purified by flash chromatography on silica gel (Biotage 75 L, in ethyl-acetate/methanol (3%) mixture. Fractions, containing pure product, were combined and evaporated to give 54 g of the title compound (yield 83%). $^1$H-NMR, CDCl$_3$, (δ): 10.37 (s, 1H), 9.11 (s, 1H), 8.87 (m, 1H), 8.19 (m, 1H), 8.05 (m, 1H), 7.56 (AB q, 4H), 7.52 (m, 1H), 7.36 (m, 1H), 7.06 (m, 2H), 4.83 (m, 1H), 4.58 (AB a, 2H), 3.96 (s, 1H), 3.19 (m, 2H), 1.49 (s, 9H), 1.22 (s, 3H), 1.18 (s, 3H). $^{13}$C-NMR, CDCl$_3$, (δ): 169.7, 167.6, 153.9, 148.4, 143.8, 140.9, 135.8, 135.6, 132.9, 131.9, 130.2, 125.9, 123.8, 122.1, 118.0, 115.9, 82.8, 73.6, 60.3, 54.8, 53.7, 50.6, 37.8, 29.1, 27.8, 23.9, 14.1. MS (m/z): 583.3[M−56], 639.4 [M+1], 661.3 [M+23].

Example 10

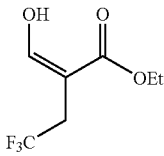

To an ice chilled solution of ethyl trifluorobutyrate (15 g, 89 mmol) and ethyl formate (36 mL, 444 mmol) in THF (200 mL) under N$_2$ was added a solution of 1 M KOtBu in THF (107 mmol, 107 mL) over a 25-minute period. After 15 minutes the ice bath was removed and the reaction mixture was stirred one hour at room temperature. Additional ethyl formate (18 mL, 222 mmol) was then added and the reaction mixture was stirred overnight. The reaction mixture was concentrated and the residue partitioned between cold ether (100 mL) and cold water (300 mL). The pH of the aqueous phase was adjusted to 2 with concentrated HCl. The product was extracted with dichloromethane (1×100 mL, 45×75 mL) and the combined organic extracts were washed with brine (1×100 mL), dried (MgSO$_4$), filtered, and concentrated to yield the title compound as thick oil which solidified upon standing, 10.2 g (58.5%). MS (m/z)=198 (M+H)$^+$.

Example 11

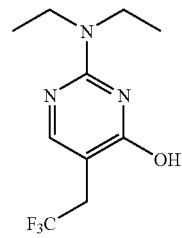

To a solution of the product of Example 10 (10 g, 51 mmol) and diethylguanidine sulfate (8.3 g, 25.2 mmol) in EtOH (60 mL) under N$_2$, was added NaOEt, 21% solution in EtOH (20.7 mL, 55.5 mmol) over a 10-minute period. The reaction mixture was then heated at reflux for 5 hours. The heterogeneous solution was cooled and poured into cold water (100 mL) to give a homogenous solution. The pH of the solution was adjusted to approximately 3.5 with conc. HCl and 1 N HCl. A solid precipitated from solution, which was collected by filtration. The light tan solid was washed with water and air-dried, yielding 2.9 g, (23%) of the title compound. MS (m/z)=250 (M+H)$^+$. $^1$H NMR (300 MHz, CD$_3$OD) δ 7.65 (br s, 1H), 3.55 (q, 4H), 3.30 (q, 2H), 1.25 (t, 6H).

Example 12

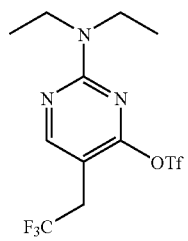

A flask was charged with the product of Example 11 (2.0 g, 8.02 mmol), DIEA (1.5 mL, 8.83 mmol), DMAP (0.98 g, 0.8 mmol), and dichloromethane (30 mL). The mixture was cooled to 0° C. and trifluoroacetic anhydride (1.5 mL, 8.83 mmol) was added. The reaction became homogeneous and was stirred at 0° C. for 3 hours. The mixture was quenched with sat. NaHCO$_3$ and extracted with dichlorormethane. The organic phase was washed with 0.2 N citric acid, dried over Na$_2$SO$_4$, filtered, and concentrated in vacuo to yield 2.87 g (94%) of the title compound as a brown solid. $^1$H NMR (300 MHz, CDCl$_3$) δ 8.28 (s, 1H), 3.65-3.52 (m, 4H), 3.29-3.19 (q, 2H), 1.22-1.17 (t, 6H).

Example 13

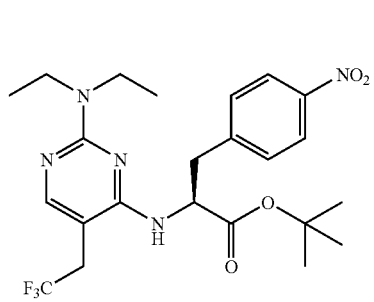

A solution of the product of Example 12 (1.3 g, 3.5 mmol), H-Phe(p-NO$_2$)OtBu (1.1 g, 4.2 mmol), and DIEA (0.9 mL, 5.3 mmol) in CH$_3$CN (14 mL) under N$_2$ was heated to reflux overnight. The next day additional H-Phe(p-NO$_2$)OtBu (0.8 g, 3 mmol) was added and reflux was continued for 3 days. The reaction mixture was then cooled and concentrated The residue taken-up in EtOAc (50 mL) and the organic portion washed with 0.5 N KHSO$_4$ (3×50 mL), water (1×50 mL), brine (1×10 mL), dried (MgSO$_4$), filtered and concentrated to a brownish gum. The crude material was purified by flash chromatography (5:1 hexanes/EtOAc) to yield 640 mg (38%) of the title compound as a golden gum. TLC: 3:1 hexanes/EtOAc, R$_f$=0.30, MS (m/z)=498 (M+H)$^+$, $^1$H NMR, (300 MHz, CDCl$_3$) δ 8.19 (d, 2H), 7.80 (s, 1H), 7.25 (d, 2H), 5.19 (br d, 1H), 4.95 (q, 1H), 3.70-3.50 (m, 4 H), 3.45-3.25 (m, 2H), 3.10 (q, 2H), 1.40 (s, 9H), 1.05 (t, 6H).

Example 14

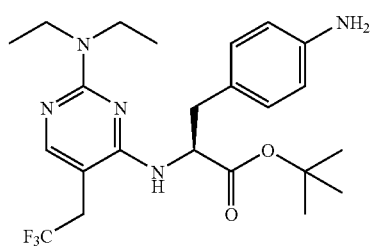

The product of Example 13 (635 mg, 1.27 mmol) was dissolved in absolute EtOH (5 mL) to which was added 35 mg of Pd/C, 10 wt %. The reaction was subjected to hydrogenation (45 psi H$_2$) for 2.5 hours at which time 50 mgs of Pd/C, 10 wt % was added and the reaction mixture again subjected to hydrogenation (45 psi H$_2$) overnight. The reaction mixture was filtered through a pad of Celite and the filtrate was concentrated to give 452 mg (76%) of the title compound. MS (m/z)=468 (M+H)$^+$, $^1$H NMR (300 MHz, CDCl$_3$) δ 7.75 (s, 1H), 6.90 (d, 2H), 6.60 (d, 2H), 5.05 (br d, 1H), 4.80 (q, 1H), 3.70-3.45 (m, 6H), 3.10-2.90 (m, 4H), 1.40 (s, 9H), 1.15 (t, 6H).

Example 15

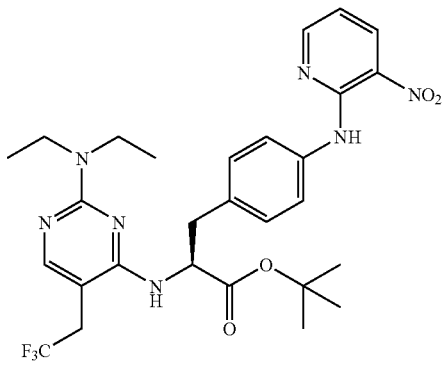

A solution of the product of Example 14 (598 mg, 1.28 mmol), 2-chloro-3-nitropyridine (243 mg, 1.53 mmol), and DIEA (0.67 mL, 3.83 mmol) in EtOH (5 mL) under N$_2$ was heated at reflux. The next day the reaction was cooled and additional 2-chloro-3-nitropyridine (40 mg, 0.25 mmol) and DIEA (0.11 mL, 0.60 mmol) was added and the reaction was heated at reflux for one day. The reaction mixture was then concentrated and the residue taken-up in EtOAc (20 mL). The organic phase was washed with water (2×20 mL). The combined aqueous washes was back extracted with EtOAc (2×10 mL). The combined organic extracts were washed with 0.2 N citric acid (3×20 mL), water (1×10 mL), sat. NaHCO3 (3×20 mL), brine (1×10 mL), dried (MgSO4), filtered and stripped to an orange gum. The crude product was purified by flash chromatography eluting with 4:1 hexanes/EtOAc (R$_f$=0.14) to yield 610 mg (81%) of the title compound as a red oil. MS (m/z)=590 (M+H)$^+$, $^1$H NMR (300 MHz, CDCl$_3$) δ 10.10 (s, 1H), 8.55 (d, 1H), 8.50 (m, 1H), 7.79 (s, 1 H), 7.75 (d, 2H), 7.15 (d, 2H), 6.80 (q, 1H), 5.10 (br d, 1H), 4.90 (m, 1H), 3.70-3.45 (m, 4H), 3.25 (m, 2H), 3.10 (q, 2 H), 1.40 (s, 9H), 1.10 (t, 6H)

Example 16

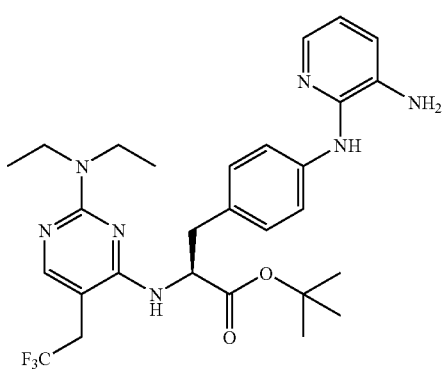

To a solution of the product of Example 15 (610 mg, 1.03 mmol) in absolute EtOH (5 mL) was added 60 mg of Pd/C, 10 wt %. The mixture was subjected to hydrogenation (45 psi H$_2$) overnight. The next day the reaction mix was filtered through Celite and the filtrate concentrated to give 500 mg (87%) of the title compound. MS (m/z)=560 (M+H)$^+$, $^1$H NMR (300 MHz CDCl$_3$) δ 7.85 (d, 2H), 7.80 (s, 1H), 7.20 (d, 2H), 7.05 (d, 2H), 7.00 (d, 1H), 7.75 (m, 1H), 6.20 (br s 1H), 5.15 (br s, 1H), 4.85 (m, 1H), 3.75-3.45 (m, 4H), 3.40 (br s, 2H), 3.15 (m, 2H), 3.05 (q, 2H), 1.40 (s, 9H), 1.15 (t, 6H).

Example 17

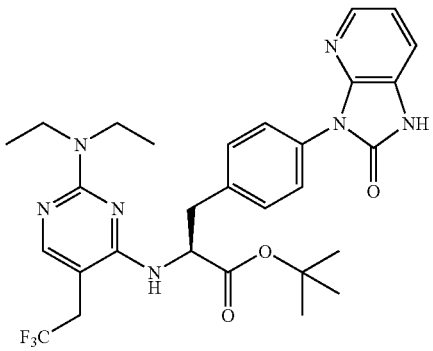

A solution of the product of Example 16 (141 mg, 0.250 mmol) and CDI (62 mg, 0.378 mmol) in CH$_2$Cl$_2$ (3 mL) was stirred overnight. The next day additional CDI (30 mg, 0.185 mmol) was added and the reaction was stirred another day. The reaction mixture was then concentrated and taken-up in EtOAc (10 mL) and the organic portion washed with 0.2 N citric acid (3×5 mL), water (1×5 mL), sat. NaHCO$_3$ (3×5 mL), brine (1×5 mL), dried (MgSO$_4$), filtered and concentrated to yield 69 mg (47%) the title compound as a foam which was used without further purification. MS (m/z)=586 (M+H)$^+$, $^1$H NMR (300 MHz, CDCl$_3$) δ 8.20 (br s, 1H), 8.05 (d, 1H), 7.80 (s, 1H), 7.65 (d, 2H), 7.90 (m, 3H), 7.05 (m, 1H), 5.15 (br d, 1H), 4.95 (m, 1H), 3.70-3.45 (m, 4H), 3.25 (app d, 2H), 3.10 (q, 2H), 1.40 (s, 9H), 1.15 (t, 6H).

Example 18

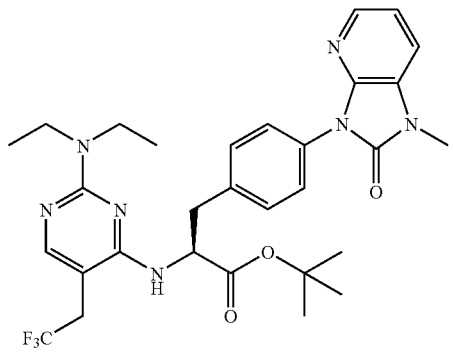

To a solution of the product of Example 17 (67 mg, 0.114 mmol) and K$_2$CO$_3$ (150 mg, 0.457 mmol) in acetone (1 mL) was added MeI (21 uL, 0.343 mmol). The suspension was stirred overnight at room temperature. The reaction mixture was then concentrated and the residue was taken-up in EtOAc (5 mL). The organic portion was washed with water (3×10 mL), brine (1×10 mL), dried (MgSO$_4$) filtered and concen- trated to yield 69 mg (100%) of the title compound as a clear oil which was used without further purification. MS (m/z)= 600 (M+H)$^+$, $^1$H NMR (300 MHz, CDCl$_3$) δ 8.10 (d, 1H), 7.75 (s, 1H), 7.61 (d, 2H), 7.30 (d, 2 H), 7.25 (m, 1H), 7.05 (m, 1H), 5.15 (br s, 1H), 4.95 (m, 1H), 3.75-3.40 (m, 7H), 3.25 (m, 2H), 3.10 (d, 2H), 1.40 (s, 9H), 1.15 (t, 6H).

Example 19

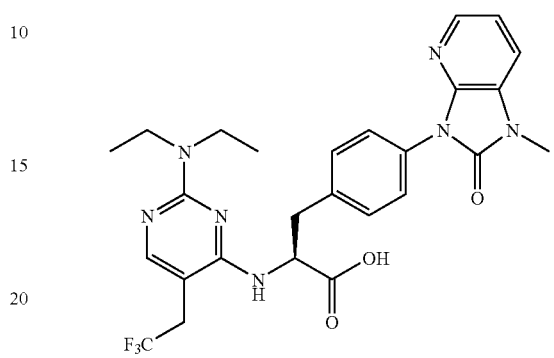

The product of Example 18 (69 mg, 0.115 mmol) was dissolved in formic acid (2 ml) and the solution was warmed at 40° C. overnight. The reaction mixture was concentrated to yield 55 mg (88%) of the title compound as a tan solid. TLC: R$_f$=0.50 (7:3 MeOH/H$_2$O+0.1% TFA, Reverse Phase C-18 silica), MS (m/z)=544 (M+H)$^+$, $^1$H NMR (300 MHz, DMSO-d$_6$) δ 7.15 (s, 1H), 7.99 (d, 2H), 7.70 (s, 1H), 7.65-7.55 (m, 2H), 7.45 (d, 2 H), 7.19 (m, 2H), 7.05 (app d, 1H), 7.61 (m, 1H), 3.65-3.10 (m, 11H), 1.10 (t, 6H), $^{13}$C NMR (75 MHz, DMSO-d6) δ 174.9, 164.2, 161.5, 160.7, 159.0, 153.3, 143.8, 141.1, 138.7, 132.7, 130.5, 129.5, 126.7, 125.8, 125.4, 118.9, 115.6, 96.0, 56.4, 41.9, 36.8, 31.4, 31.0, 27.8, 14.2.

Example 20

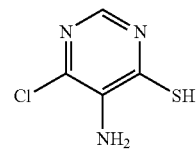

To a solution of 4,6-dichloro-5-aminopyrimidine (5.0 g, 30.7 mmol) in DMSO (30 mL) was added Na$_2$S.9H$_2$O (7.4 g, 30.8 mmol). The mixture was stirred at room temperature overnight. Water (40 mL) was then added to the mixture and the solution evaporated under reduced pressure to approximately 6 mL. To this solution was added conc. HCl (0.5 mL) and water to precipitate the product. The solution was filtered and the orange solid was washed with water and dried to afford 4.3 g (86%) of the title compound. $^1$H NMR (300 MHz, DMSO-d$_6$) δ 5.84 (2H, s), 7.79 (1H, s), 14.37 (1H, br s); MS (m/z): MH$^+$=162.

Example 21

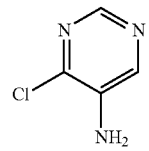

To the product of Example 20 (4.3 g, 26 mmol) dissolved in conc. NH$_4$OH (4 mL) was added EtOH (40 mL). To this solution, Raney Nickel (excess) was added in portions. The reaction was stirred at room temperature overnight and then heated at 80° C. for 2 hrs. The mixture was filtered through Celite and the filtrate concentrated. The crude product was purified by flash chromatography on silica using EtOAc/hexanes to afford 1.6 g (47%) of the title compound as a yellow solid. $^1$H NMR (300 MHz, DMSO-d$_6$) δ 5.90 (2H, s), 8.20 (2H, s); MS (m/z) MH$^+$=130.

Example 22

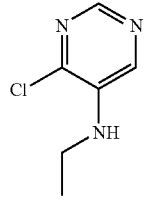

To the product of Example 21 (0.51 g, 3.9 mmol) in MeOH (20 mL) and HOAc (0.5 mL) was added CH$_3$CHO (0.52 mL, 9.2 mmol) Then NaBH$_3$CN (590 mg, 9.2 mmol) was added in one portion. The reaction was stirred at room temperature overnight and additional HOAc, CH$_3$CHO, and NaBH$_3$CN were added. The reaction was stirred overnight, concentrated, and the residue was taken up in EtOAc and sat. NaHCO$_3$. The separated aqueous layer was back extracted with EtOAc. The combined organic layer was dried and concentrated to a residue. The residue was dissolved in MeOH and treated with HOAc, CH$_3$CHO and NaBH$_3$CN as described above. Following the work up procedure described above the crude product was purified by flash chromatography on silica using EtOAc/hexanes, to afford 0.35 g (57%) of the title compound as a yellow oil. $^1$H NMR (300 MHz, CDCl$_3$) δ 1.35 (3H, q, J=12 Hz), 3.29 (2H, m), 4.21 (1H, bs), 8.04 (1H, s), 8.36 (1H, s); MS (m/z): MH$^+$=158.

Example 23

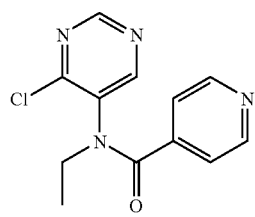

To the product of Example 22 (70 mg, 0.45 mmol) dissolved in DMF (1 mL) was added TEA (93 uL) and isonicotinoyl chloride (0.12 g, 0.67 mmol). The reaction mixture was stirred at room temperature for 2 days and then partitioned between EtOAc and sat. NaHCO$_3$. The separated aqueous layer was back extracted with EtOAc. The combined organic layer was dried and concentrated to give 67 mg (57%) of the title compound which was used without further purification. $^1$H NMR (300 MHz, CDCl$_3$) δ 1.26 (3H), 3.65-3.69 (1H), 4.21 (1H), 7.17 (2H), 8.43 (1H), 8.54 (2H), 8.86 (1H) Note:

$^1$H NMR shows evidence of rotamers as demonstrated of broadness of all peaks; MS (m/z): MH$^+$=263.

Example 24

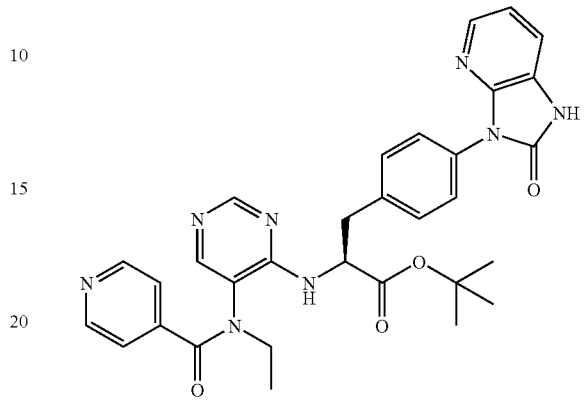

To a solution of the product of Example 23 (0.11 g, 0.42 mmol) and the product of Example 8 (0.135 g, 0.38 mmol) in IPA (2.5 ml) was added DIEA (0.35 ml, 1.9 mmol). The reaction mixture was stirred in a sealed tube at 130° C. for 2 days. The crude mixture was concentrated and the oil was purified by flash column chromatography with a solvent gradient of 0-10% MeOH in CH$_2$Cl$_2$ to yield the title compound as an oil. $^1$H NMR (300 MHz, CDCl$_3$) δ 1.16 (1.2H, m), 1.26-1.31 (1.8H, m), 1.50-1.53 (9H, d, J=9 Hz), 3.0 (1H, m), 3.2 (0.8H, m), 3.36 (1.2H, m), 4.12-4.18 (1.2H, m), 4.96-5.10 (0.8H, m), 5.80-5.95 (1H, m), 6.93-6.96 (1H, m), 7.07 (1H, m), 7.31-7.45 (5 H, m), 7.66-7.75 (3H, m), 8.06 (1H, m), 8.44-8.51 (2H, m); HPLC/MS: single peak at 1.29 min, MH$^+$=581.

Example 25

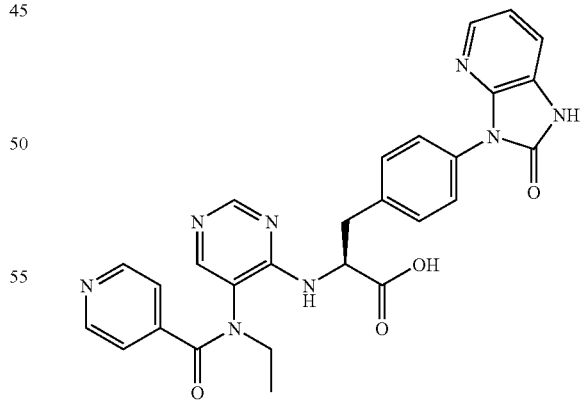

To the product of Example 24 (7.6 mg, 0.013 mmol) was dissolved in CH$_2$Cl$_2$ (0.1 ml) and TFA (0.05 ml). The reaction was stirred at room temperature overnight and then concentrated to yield the title compound. $^1$H NMR (300 MHz, CDCl$_3$) δ 1.07-1.21 (3H, m), 3.2-3.3 (2H, m), 3.65-3.8 (2H, m), 4.2-4.5 (2H, m), 5.54 (1H, bs), 7.15-7.18 (1H, m), 7.35

(1H, m), 7.46 (1H, m), 7.56-7.63 (4H, m), 7.81 (1H, bs), 7.95 (1H, m), 8.25 (1H, m), 8.58 (3H, m); HPLC/MS: single peak at 0.4 min, MH+=525.

Example 26

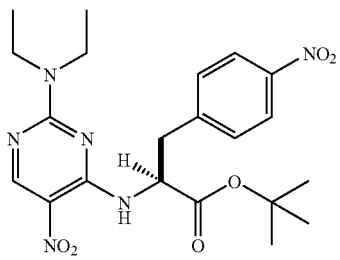

To a cold solution of 2,4-dichloro-5-nitropyrimidine (3.5 g, 18.1 mmol) and N,N-diisopropylethylamine (3.2 mL, 18.1 mmol) in THF (30 mL) was added a solution of L-4'-nitrophenylalanine t-butyl ester (4.84 g, 18.1 mmol) in THF (15 mL) via cannula. After complete addition, the mixture was stirred at 0° C. for 30 minutes. Diethylamine (3.0 mL, 29.0 mmol) was added and the reaction stirred for 18 hours at room temperature. The reaction mixture was concentrated in vacuo and the residue taken up in 0.5 N HCl (100 mL). The mixture was extracted with dichloromethane (3×50 mL) and the combined organic layers were washed with sat $NaHCO_3$, water, dried ($Na_2SO_4$), and concentrated in vacuo. The residue was purified by flash chromatography on silica using ethyl acetate/hexanes, to afford 5.9 g (70%) of the title compound as a white solid. $^1$H NMR (300 MHz, $CDCl_3$) δ 1.24 (6H, m), 1.40 (9H, s), 3.11 (2H, m), 3.51-3.72 (4H, m), 5.00 (1H, q, J=6 Hz), 7.35 (2H, d, J=9 Hz), 8.13 (2H, d, J=9 Hz), 8.73 (1H, brd), 8.97 (1H, s); $^{13}$C NMR (75 MHZ, $CDCl_3$) δ 12.7, 13.2, 27.8, 37.6, 42.6, 42.8, 54.7, 82.9, 120.0, 123.6, 130.1, 143.9, 147.0, 154.8, 157.6, 159.9, 169.2; HPLC/MS: single peak at 4.071 min, MH+=461.

Example 27

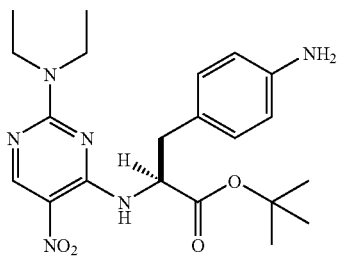

To a solution of the product of Example 26 (10.75 g, 23 mmol) in ethyl acetate (200 mL) was added of 10 wt % Pd/C (0.81 g). While stirring, the flask was connected to house vacuum for 15 minutes. The flask was capped with a septum, flushed with hydrogen gas via balloon, and stirred under the hydrogen atmosphere for 4 hours. The mixture was filtered through Celite and the filtrate was concentrated in vacuo to afford 9.87 g (98%) of the title compound as a clear oil. The product was used without further purification. $^1$H NMR (300 MHz, $CDCl_3$) δ 1.24 (6H, m), 1.40 (9H, s), 3.11 (2H, t, J=6 Hz), 3.51-3.70 (4H, m), 4.80 (1H, q, J=6 Hz), 6.60 (2H, d, J=9 Hz), 6.97 (2H, d, J=9 Hz), 8.64 (1H, brd), 8.97 (1H, s); $^{13}$C NMR (75 MHz, $CDCl_3$) δ 12.8, 13.4, 27.9, 37.0, 42.5, 42.8, 54.7, 82.0, 115.3, 120.1, 125.7, 130.2, 145.4, 154.9, 157.7, 160.1, 170.3; HPLC/MS: single peak at 2.704 min, MH+=431.

Example 28

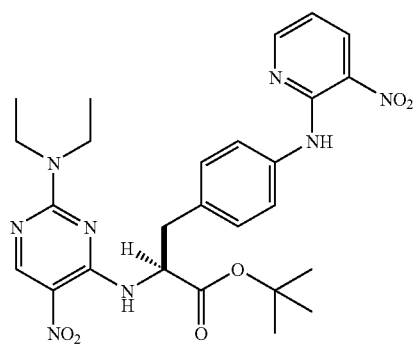

To a solution of the product of Example 27 (0.46 g, 1.1 mmol) and 2-chloro-3-nitropyrimidine (0.2 g, 1.3 mmol) in ethanol was added N,N-diisopropylethylamine (0.4 ml, 2.3 mmol). The reaction mixture was heated at reflux for 18 hours and then cooled to room temperature. The mixture was concentrated in vacuo and the residue taken up in ethyl acetate. This solution was washed with 0.2 N citric acid, water, sat $NaHCO_3$, brine, dried ($Na_2SO_4$), filtered, and concentrated in vacuo to yield the title compound which was used without further purification. $^1$H NMR (300 MHz, $CDCl_3$) δ 1.17-1.29 (6H, m), 1.40 (9H, s), 3.22 (2H, t, J=6 Hz), 3.64-3.71 (4H, m), 4.90 (1H, q, J=9 Hz), 6.80-6.85 (1H, m), 7.24 (2H, d, J=9 Hz), 7.60 (2H, d, J=9 Hz), 8.46-8.53 (2H, m), 8.72 (1H, d, J=6 Hz), 8.98 (1H, s), 10.11 (1H, s); $^{13}$C NMR (75 MHz, $CDCl_3$) δ 12.9, 13.3, 27.9, 37.4, 42.6, 42.9, 82.3, 113.9, 120.1, 122.5, 129.9, 132.4, 135.5, 136.9, 154.9, 155.2, 157.7, 160.1, 170.1; MS: single peak at 6.037 min, MH+=553.

Example 29

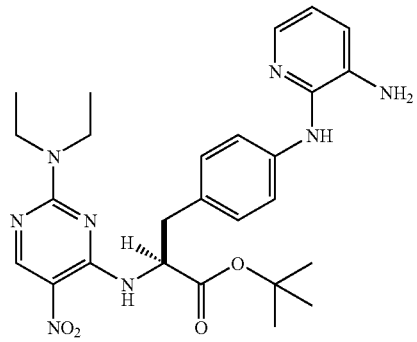

To a solution of the product of Example 28 (0.1 g, 0.17 mmol) in ethanol was added 10 wt % Pd/C (0.01 g). The reaction mixture was evacuated, flushed with hydrogen via balloon, and stirred under the hydrogen atmosphere for one hour. The reaction mixture was filtered through Celite and the filtrate concentrated in vacuo to give the title compound which was used without further purification. ¹H NMR (300 MHz, CDCl₃) δ 1.16-1.31 (6H, m), 1.42 (9H, s), 3.06-3.19 (2H, m), 3.47-3.71 (4 H, m), 4.84 (1H, q, J=6 Hz), 5.291 (1H, s), 6.29 (1H, bs), 6.74 (1H, t, J=7 Hz), 6.98 (1H, d, J=7.2 Hz), 7.12 (2H, d, J=7.8 Hz), 7.22 (2H, d, J=8.1 Hz), 7.78 (1H, d, J=4.5 Hz), 8.65 (1H, d, J=6.9 Hz), 8.95 (1H, s); ¹³C NMR (75 MHz, CDCl₃) δ 12.9, 13.4, 27.9, 37.2, 42.6, 42.9, 82.1, 117.2, 118.5, 120.1, 123.5, 128.6, 129.9, 131.0, 138.8, 140.4, 145.4, 154.9, 157.7, 160.0, 170.4; HPLC/MS: single peak at 2.645 min, MH⁺=523.

Example 30

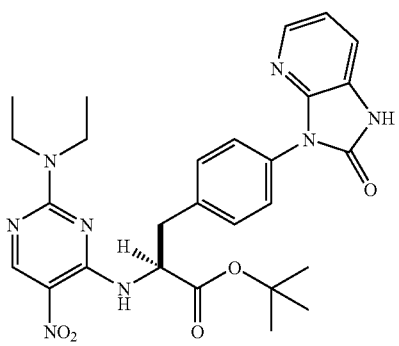

The product of Example 29 (0.075 g, 0.14 mmol) and carbonyl diimidazole (0.05 g, 0.31 mmol) in dichloromethane (3 mL) were stirred at room temperature overnight. The reaction mixture was washed with water, dried (Na₂SO₄), filtered, and concentrated in vacuo to yield the title compound which was used without further purification. ¹H NMR (300 MHz, CDCl₃) δ 1.17-1.28 (6H, m), 1.44 (9H, s), 3.18-3.35 (2H, m), 3.53-3.73 (4H, m), 4.87-4.94 (1H, m), 7.02-7.07 (1H, m), 7.36 (1H, d, J=9 Hz), 7.44 (2H, d, J=9 Hz), 7.70 (2H, d, J=9 Hz), 8.05 (1H, d, J=6 Hz), 8.76 (1H, d, J=6 Hz), 8.99 (1H, s), 10.40 (1H, s); ¹³C NMR (75 MHz, CDCl₃) δ 12.9, 13.3, 27.9, 37.7, 42.5, 42.8, 55.6, 82.4, 116.2, 118.2, 120.1, 122.2, 126.1, 130.0, 131.9, 136.0, 141.1, 143.8, 154.2, 155.1, 157.6, 160.0, 170.2; HPLC/MS: single peak at 2.2 min, MH⁺=549.

Example 31

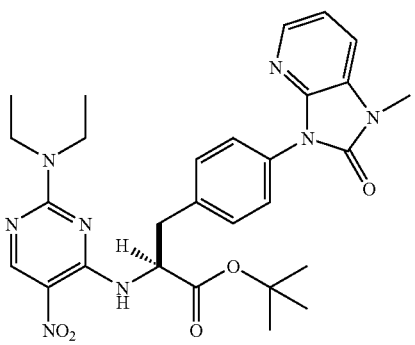

To a solution of the product of Example 30 (0.02 g, 0.037 mmol) in acetone (3 mL) was added Cs₂CO₃ (0.05 g, 0.15 mmol) and iodomethane (20 μL, 0.33 mmol). The reaction was stirred for 30 minutes, concentrated in vacuo, and the residue partitioned between dichloromethane and water. The organic portion was collected, dried (Na₂SO₄), filtered, and concentrated in vacuo to yield the title compound which was used without further purification. ¹H NMR (300 MHz, CDCl₃) δ 1.17-1.27 (6H, m), 1.41 (9H, s), 3.17-3.30 (2H, m), 3.49 (3 H, s), 3.56-3.72 (4H, m), 4.86-4.93 (1H, m), 7.05-7.09 (1H, m), 7.25 (1H, d, J=6 Hz), 7.39 (2H, d, J=9 Hz), 7.679 (2H, d, J=9 Hz), 8.04 (1H, d, J=6 Hz), 8.75 (1H, d, J=6 Hz), 8.98 (1H, s); ¹³C NMR (75 MHz, CDCl₃) δ 12.9, 13.3, 27.0, 27.9, 37.8, 42.5, 42.9, 55.6, 82.4, 113.5, 117.7, 120.1, 124.3, 125.8, 129.9, 132.3, 135.6, 140.8, 143.1, 155.0, 157.6, 160.0, 170.2; HPLC/MS: single peak at 2.6 min, MH⁺=563.

Example 32

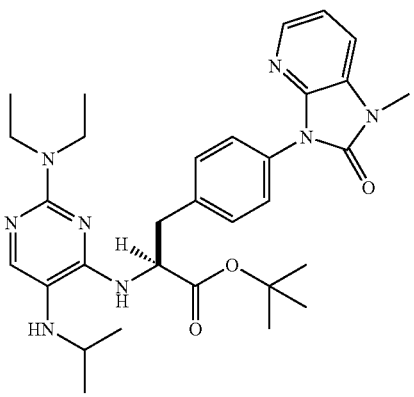

To a solution of the product of Example 31 (0.9 g 1.6 mmol) in ethanol (10 mL) and ethyl acetate (10 mL) was added 10 wt % Pd/C (0.15 g). The reaction mixture was hydrogenated for 18 hours (55 psi of H₂), filtered through Celite, and concentrated in vacuo. The residue was dissolved in ethanol (5 mL) and acetone (5 mL). Platinum oxide (0.09 g) and a few drops of glacial acetic acid were added and the reaction mixture was hydrogenated for 18 hours (55 psi of H₂). The mixture was filtered through Celite and the filtrate concentrated in vacuo. The residue was taken up in dichloromethane, washed with sat NaHCO₃, dried (Na₂SO₄), filtered and concentrated in vacuo. The residue was taken up in toluene and concentrated in vacuo yielding the title compound. ¹H NMR analysis of this residue demonstrated the product contained no residual acetic acid. ¹H NMR (300 MHz, CDCl₃) δ 1.05 (6H, d, J=6 Hz), 1.17 (6H, t, J=6 Hz), 1.39 (9H, s), 2.04 (1H, bs), 3.03 (1H, m), 3.24 (2H, d, J=6 Hz), 3.48 (3H, s), 3.51-3.64 (4H, m), 4.83 (1H, m), 5.92 (1H, d, J=6 Hz), 7.03-7.08 (1H, m), 7.22 (1H, m), 7.35 (2H, d, J=9 Hz), 7.62 (3H, m), 8.03 (1H, d, J=6 Hz); ¹³C NMR (75 MHz, CDCl₃) δ 13.2, 22.8, 22.9, 26.9, 27.9, 37.4, 42.0, 48.2, 54.8, 82.0, 113.6, 116.2, 117.7, 124.3, 125.6, 129.9, 132.1, 136.1, 140.7, 143.1, 144.1, 152.7, 155.68, 159.0, 171.1; HPLC/MS: single peak at 2.8 min, MH+=575.

$^{13}$C NMR shows evidence of rotamers; HPLC/MS (m/z): single peak at 2.7 min, MH+=653.

Example 33

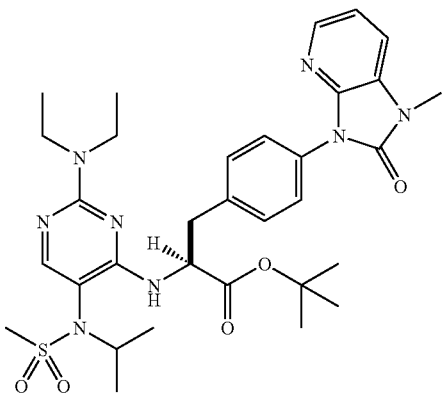

Example 34

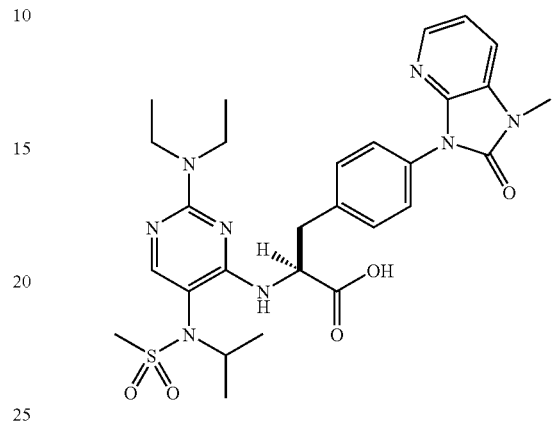

To a solution of the product of Example 32 (0.38 g, 0.66 mmol) in pyridine (3 mL) at 0° C. was added methanesulfonyl chloride (0.3 mL, 3.9 mmol). The reaction was allowed to warm to room temperature overnight and was concentrated in vacuo. The residue was taken up in ethyl acetate, washed with 0.2 N citric acid, water, sat NaHCO$_3$, brine, dried (Na$_2$SO$_4$), filtered, and concentrated in vacuo to give the title compound which was used without further purification. $^1$H NMR (300 MHz, CDCl$_3$) δ 0.85 (1.5H, d, J=7 Hz), 1.02 (1.5H, d, J=7 Hz), 1.13-1.24 (9H, m), 1.37 (4.5H, s), 1.39 (4.5H, s), 2.77 (1.5H, s), 2.89 (1.5H, s), 3.19-3.27 (2H, m), 3.45 (3H, s), 3.47-3.62 (4H, m), 4.36-4.40 (1H, m), 4.76-4.83 (1H, m), 5.64 (0.5H, d, J=7 Hz), 5.71 (0.5H, d, J=7 Hz), 7.01-7.05 (1H, m), 7.20 (1H, d, J=8 Hz), 7.29-7.35 (2H, m), 7.58-7.62 (2H, m), 7.75 (1H, s), 7.98-7.99 (1H, d, J=1 Hz), $^1$H NMR shows evidence of rotamers; $^{13}$C NMR (75 MHz, CDCl$_3$) δ 13.3, 20.9, 21.4, 21.5, 37.5, 37.6, 39.9, 39.9, 41.9, 51.8, 51.9, 54.6, 55.1, 81.9, 82.2, 103.9, 104.2, 113.9, 104.2, 113.5, 113.6, 117.7, 124.3, 125.7, 125.9, 129.9, 130.1, 132.1, 132.2, 135.9, 136.2, 140.7, 143.2, 152.7, 157.4, 159.6, 160.3, 160.6, 170.1, The product of Example 33 (0.05 g, 0.077 mmol) was dissolved in formic acid and heated at 40° C. for 18 hours. The reaction mixture was concentrated in vacuo to yield the title compound. $^1$H NMR (300 MHz, CDCl$_3$) δ 0.81 (1.5H, d, J=9 Hz), 1.03 (1.5H, d, J=9 Hz), 1.13-1.48 (9H, m), 2.92 (1.5H, s), 2.98 (1.5H, s), 3.21-3.56 (9H, m), 4.24-4.35 (1H, m), 4.82 (0.5H, d, J=6 Hz), 4.92 (0.5H, d, J=6 Hz), 7.01-7.11 (2H, m), 7.26-7.30 (2H, m), 7.35-7.38 (1H, m), 7.50-7.58 (2H, m), 8.00 (0.5H, s), 8.01 (0.5H, s), 8.09 (1H, d, J=9 Hz), $^1$H NMR shows evidence of rotamers; $^{13}$C NMR (75 MHz, CDCl$_3$) δ 12.6, 12.7, 21.4, 27.1, 39.8, 39.9, 52.7, 106.8, 107.1, 114.2, 118.0, 124.4, 126.3, 126.4, 130.1, 130.4, 132.0, 135.7, 136.2, 140.5, 142.9, 144.4, 151.2, 151.3, 152.9, 161.1, 161.4, 165.1, 173.9, $^{13}$C NMR shows evidence of rotamers; HPLC/MS (m/z): single peak at 2.27 min, MH+=597.

Example 35

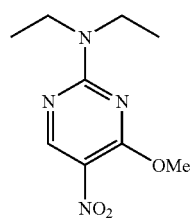

To 2,4-dichloro-5-nitropyrimidine (2.0 g, 10.3 mmol) in MeOH (7 mL) at 0° C. under N$_2$ was added NaOMe (0.5 M in MeOH, 25 mL) dropwise. After the addition was completed, the reaction mixture was stirred at 0 C for 15 min. Then diethylamine (5 mL) was added and the mixture was stirred at rt overnight. The reaction mixture was concentrated and the residue was partitioned between EtOAc and H₂O. The organic layer was dried and concentrated to a residue which was purified by flash chromatography on silica using EtOAc/Hexanes, to afford the title compounds as an off white solid (1.1 g, 4.9 mmol, 47% yield). ¹H NMR (300 MHz, CDCl3) δ 1.26 (6H, t, J=6.6 Hz), 3.70 (4H, m), 4.08 (3H, s), 9.01 (1H, s); HPLC/MS: MH⁺=227.

Example 36

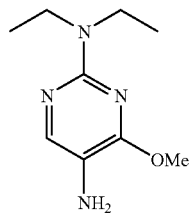

To the product of Example 35 (1.1 g, 4.9 mmol) in MeOH/EtOAc (1:1, 20 mL) was reduced with Pd/C (5% degussa, 0.5 g) and H₂ (50 psi) in a Parr shaker overnight. The reaction mixture was filtered and the filtrated was concentrated under reduced pressure to afford the title compound as a solid (0.85 g, 4.3 mmol, 88.5% yield). ¹H NMR (300 MHz, CDCl₃) δ 1.18 (6H, t, J=6.9 Hz), 3.03 (2H, br), 3.57 (6H, t, J=6.9 Hz), 3.96 (3H, s), 7.71 (1H, s); HPLC/MS: MH⁺=197.

Example 37

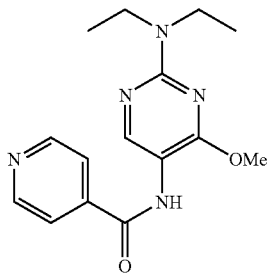

To the product of Example 36 (0.85 g, 4.3 mmol) in CH₂Cl₂ (15 mL) and TEA (1.4 mL, 10 mmol) was added isonicotinyl chloride HCl salt (1.13 g, 6.3 mmol). After 15 min, TLC showed no starting material. The mixture was extracted between EtOAc and sat. NaHCO₃. The aqueous layer was washed with EtOAc twice. The combined organic layers were washed with sat. NaHCO₃ and brine. It was dried over MgSO₄ and filtered. The filtrate was concentrated to give the title compound as a brown solid (1.3 g, 4.3 mmol, 100% yield). ¹H NMR (300 MHz, CDCl₃) δ 1.20 (6H, t, J=6.9 Hz), 3.60 (4H, q, J=6.9 Hz), 3.96 (3H, s), 7.72 (2H, d, J=6.0 Hz), 7.75 (1H, bs), 8.80 (2H, d, J=6.0 Hz), 8.89 (1H, s); HPLC/MS: MH⁺=302.

Example 38

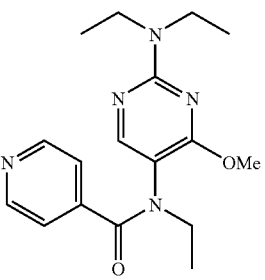

To the product of Example 37 (100 mg, 0.33 mmol) in THF (1 mL) was added KOtBu (1M in THF, 0.5 mL) slowly followed by EtI (40 µL, 0.5 mmol). The reaction mixture was stirred at rt overnight. TLC showed the disappearance of the starting material. The mixture was partitioned between EtOAc and H₂O. The aqueous layer was washed with EtOAc. The combined organic layers were washed with sat. NaHCO₃ and brine. It was dried and concentrated to give the title compound (90 mg, 0.27 mmol, 83%) that was used without further purification. ¹H NMR (300 MHz, CDCl₃) δ 1.10 (9H, m), 3.47 (5H, m), 3.92 (1H, m), 7.14 (2H, d, J=6.0 Hz), 7.78 (1H, bs), 8.44 (2H, d, J=6.0 Hz); HPLC/MS: MH⁺=330.

Example 39

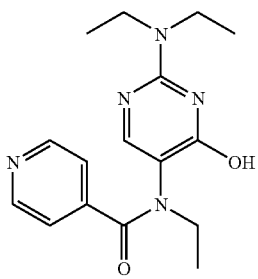

To the product of Example 38 (200 mg, 0.61 mmol) in DMF (4 mL) was added EtSNa (66 mg, 0.79 mmol) and the reaction mixture was heated at 100 C for 1 hr. LC/MS showed starting material still present. Another portion of NaSEt (66 mg, 0.79 mmol) was added and the reaction heated for another 2 hr. LC/MS showed product only. DMF was removed under reduced pressure and H₂O (10 mL) was added followed by conc. HCl (0.132 mL). Evaporating of the solvent left a residue. It was dissolved in EtOH and filtered. The filtrate was concentrated to yield the title compound (190 mg, 100%) that was used without further purification. ¹H NMR (300 MHz, CD$_3$OD) δ 1.24 (9H, m), 3.60 (4H, m), 3.60-4.00 (2H, br), 8.12 (3H, d, J=5.7 Hz), 8.92 (2H, d, J=5.7 Hz); HPLC/MS: MH$^+$=316.

Example 40

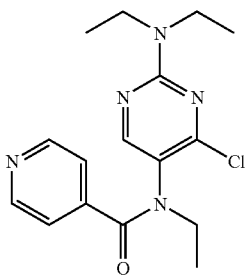

To the product of Example 39 (70 mg, 0.22 mmol) in POCl$_3$ (3 mL) at rt was added diethylaniline (30 μL). The reaction mixture was heated to 100 C for 30 min. Then it was concentrated. The residue was partitioned between EtOAc and H$_2$O. The organic layer was washed with H$_2$O twice. Then it was dried and concentrated to give the title compound (50 mg, 0.15 mmol, 68%) and used for the next reaction without further purification. HPLC/MS: MH$^+$=334

Example 41

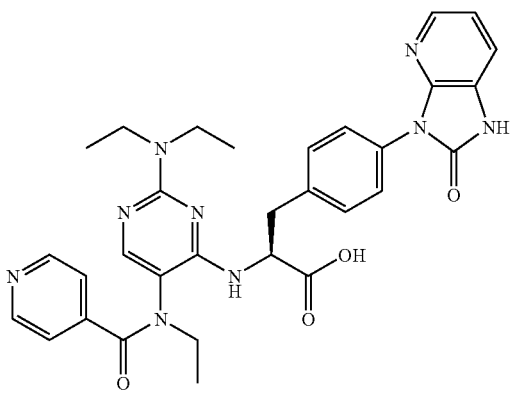

To a solution of the product of Example 40 (50 mg, 0.15 mmol) and the product of Example 8 (60 mg, 0.17 mmol) in IPA (0.75 mL) was added DIEA (0.15 mL, 0.8 mmol). The reaction mixture was stirred in a sealed tube at 130 degrees for 7 days. The crude mixture was concentrated and the residue was purified by preparative HPLC and silica gel flash chromatography to yield an off white solid (10 mg) that was contaminated with some silica. To this solid was added 0.5 mL HCOOH and the reaction was heated at 40° C. overnight. Then the acid was removed and the residue was purified by preparative HPLC to afford the title compound (3.4 mg, 0.0057 mmol, 3.8%). $^1$H NMR (300 MHz, CD$_3$OD) δ 1.00-1.30 (9H, m), 2.65-3.00 (2H, m), 3.30-3.70 (5H, m), 4.24 (1H, m), 4.90-5.30 (1H, m, overlap with CD$_3$OD), 7.15 (1H, m), 7.25-7.75 (8H, m), 7.90 (1H, m), 8.69 (2H, br); HPLC/MS: MH$^+$=596.

Biological Examples

Example A

In Vitro Assay for Determining Binding of Candidate Compounds to VLA-4

An in vitro assay was used to assess binding of candidate compounds to $\alpha_4\beta_1$ integrin. Compounds which bind in this assay can be used to assess VCAM-1 levels in biological samples by conventional assays (e.g., competitive assays). This assay is sensitive to IC$_{50}$ values as low as about 1 nM.

The activity of $\alpha_4\beta_1$ integrin was measured by the interaction of soluble VCAM-1 with Jurkat cells (e.g., American Type Culture Collection Nos. TIB 152, TIB 153, and CRL 8163), a human T-cell line which expresses high levels of $\alpha_4\beta_1$ integrin. VCAM-1 interacts with the cell surface in an $\alpha_4\beta_1$ integrin-dependent fashion (Yednock, et al. J. Biol. Chem., 1995, 270:28740).

Recombinant soluble VCAM-1 was expressed as a chimeric fusion protein containing the seven extracellular domains of VCAM-1 on the N-terminus and the human IgG$_1$ heavy chain constant region on the C-terminus. The VCAM-1 fusion protein was made and purified by the manner described by Yednock, supra.

Jurkat cells were grown in RPMI 1640 supplemented with 10% fetal bovine serum, penicillin, streptomycin and glutamine as described by Yednock, supra.

Jurkat cells were incubated with 1.5 mM MnCl$_2$ and 5 μg/mL 15/7 antibody for 30 minutes on ice. Mn$^{+2}$ activates the receptor to enhance ligand binding, and 15/7 is a monoclonal antibody that recognizes an activated/ligand occupied conformation of $\alpha_4\beta_1$ integrin and locks the molecule into this conformation thereby stabilizing the VCAM-1/$\alpha_4\beta_1$ integrin interaction. Yednock, et al., supra. Antibodies similar to the 15/7 antibody have been prepared by other investigators (Luque, et al, 1996, J. Biol. Chem. 271:11067) and may be used in this assay.

Cells were then incubated for 30 minutes at room temperature with candidate compounds, in various concentrations ranging from 66 μM to 0.01 μM using a standard 5-point serial dilution. 15 μL soluble recombinant VCAM-1 fusion protein was then added to Jurkat cells and incubated for 30 minutes on ice. (Yednock et al., supra.).

Cells were then washed two times and resuspended in PE-conjugated goat F(ab')$_2$ anti-mouse IgG Fc (Immunotech, Westbrook, Me.) at 1:200 and incubated on ice, in the dark, for 30 minutes. Cells were washed twice and analyzed with a standard fluorescence activated cell sorter ("FACS") analysis as described in Yednock, et al., supra.

Compounds having an IC$_{50}$ of less than about 15 μM possess binding affinity to $\alpha_4\beta_1$.

When tested in this assay, each of the compounds prepared in the above examples has or is expected to have an IC$_{50}$ of 15 μM or less (or is expected to be active in vivo).

Example B

In Vitro Saturation Assay for Determining Binding of Candidate Compounds to $\alpha_4\beta_1$ The following describes an in vitro assay to determine the plasma levels needed for a compound to be active in the Experimental Autoimmune Encephalomyelitis ("EAE") model, described in the next example, or in other in vivo models.

Log-growth Jurkat cells are washed and resuspended in normal animal plasma containing 20 µg/ml of the 15/7 antibody (described in the above example).

The Jurkat cells are diluted two-fold into either normal plasma samples containing known candidate compound amounts in various concentrations ranging from 66 µM to 0.01 µM, using a standard 12 point serial dilution for a standard curve, or into plasma samples obtained from the peripheral blood of candidate compound-treated animals.

Cells are then incubated for 30 minutes at room temperature, washed twice with phosphate-buffered saline ("PBS") containing 2% fetal bovine serum and 1 mM each of calcium chloride and magnesium chloride (assay medium) to remove unbound 15/7 antibody.

The cells are then exposed to phycoerythrin-conjugated goat F(ab')$_2$ anti-mouse IgG Fc (Immunotech, Westbrook, Me.), which has been adsorbed for any non-specific cross-reactivity by co-incubation with 5% serum from the animal species being studied, at 1:200 and incubated in the dark at 4° C. for 30 minutes.

Cells are washed twice with assay medium and resuspended in the same. They are then analyzed with a standard fluorescence activated cell sorter ("FACS") analysis as described in Yednock et al. J. Biol. Chem., 1995, 270:28740.

The data is then graphed as fluorescence versus dose, e.g., in a normal dose-response fashion. The dose levels that result in the upper plateau of the curve represent the levels needed to obtain efficacy in an in vivo model.

This assay may also be used to determine the plasma levels needed to saturate the binding sites of other integrins, such as the $\alpha_9\beta_1$ integrin, which is the integrin most closely related $\alpha_4\beta_1$ (Palmer et al, 1993, J. Cell Bio., 123:1289). Such binding is predictive of in vivo utility for inflammatory conditions mediated by $\alpha_9\beta_1$ integrin, including by way of example, airway hyper-responsiveness and occlusion that occurs with chronic asthma, smooth muscle cell proliferation in atherosclerosis, vascular occlusion following angioplasty, fibrosis and glomerular scarring as a result of renal disease, aortic stenosis, hypertrophy of synovial membranes in rheumatoid arthritis, and inflammation and scarring that occur with the progression of ulcerative colitis and Crohn's disease.

Accordingly, the above-described assay may be performed with a human colon carcinoma cell line, SW 480 (ATTC #CCL228) transfected with cDNA encoding $\alpha_9$ integrin (Yokosaki et al., 1994, J. Biol. Chem., 269:26691), in place of the Jurkat cells, to measure the binding of the $\alpha_9\beta_1$ integrin. As a control, SW 480 cells which express other $\alpha$ and $\beta_1$ subunits may be used.

Accordingly, another aspect of this invention is directed to a method for treating a disease in a mammalian patient, which disease is mediated by $\alpha_9\beta_1$, and which method comprises administering to said patient a therapeutically effective amount of a compound of this invention. Such compounds are preferably administered in a pharmaceutical composition described herein above. Effective daily dosing will depend upon the age, weight, condition of the patient which factors can be readily ascertained by the attending clinician. However, in a preferred embodiment, the compounds are administered from about 20 to 500 µg/kg per day.

Example C

In Vivo Evaluation

The standard multiple sclerosis model, Experimental Autoimmune (or Allergic) Encephalomyelitis ("EAE"), was used to determine the effect of candidate compounds to reduce motor impairment in rats or guinea pigs. Reduction in motor impairment is based on blocking adhesion between leukocytes and the endothelium and correlates with anti-inflammatory activity in the candidate compound. This model has been previously described by Keszthelyi et al., Neurology, 1996, 47:1053-1059, and measures the delay of onset of disease.

Brains and spinal cords of adult Hartley guinea pigs were homogenized in an equal volume of phosphate-buffered saline. An equal volume of Freund's complete adjuvant (100 mg mycobacterium tuberculosis plus 10 ml Freund's incomplete adjuvant) was added to the homogenate. The mixture was emulsified by circulating it repeatedly through a 20 ml syringe with a peristaltic pump for about 20 minutes.

Female Lewis rats (2-3 months old, 170-220 g) or Hartley guinea pigs (20 day old, 180-200 g) were anesthetized with isoflurane and three injections of the emulsion, 0.1 ml each, were made in each flank. Motor impairment onset is seen in approximately 9 days.

Candidate compound treatment began on Day 8, just before onset of symptoms. Compounds were administered subcutaneously ("SC"), orally ("PO") or intraperitoneally ("IP"). Doses were given in a range of 10 mg/kg to 200 mg/kg, bid, for five days, with typical dosing of 10 to 100 mg/kg SC, 10 to 50 mg/kg PO, and 10 to 100 mg/kg IP.

Antibody GG5/3 against $\alpha_4\beta_1$ integrin (Keszthelyi et al., Neurology, 1996, 47:1053-1059), which delays the onset of symptoms, was used as a positive control and was injected subcutaneously at 3 mg/kg on Day 8 and 11.

Body weight and motor impairment were measured daily. Motor impairment was rated with the following clinical score:

0 no change
1 tail weakness or paralysis
2 hindlimb weakness
3 hindlimb paralysis
4 moribund or dead A candidate compound was considered active if it delayed the onset of symptoms, e.g., produced clinical scores no greater than 2 or slowed body weight loss as compared to the control.

Example D

Asthma Model

Inflammatory conditions mediated by $\alpha_4\beta_1$ integrin include, for example, airway hyper-responsiveness and occlusion that occurs with chronic asthma. The following describes an asthma model which can be used to study the in vivo effects of the compounds of this invention for use in treating asthma.

Following the procedures described by Abraham et al, J. Clin. Invest, 93:776-787 (1994) and Abraham et al, Am J. Respir Crit Care Med, 156:696-703 (1997), both of which are incorporated by reference in their entirety. Compounds of this invention are formulated into an aerosol and administered to sheep which are hypersensitive to Ascaris suum antigen. Compounds which decrease the early antigen-induced bronchial response and/or block the late-phase airway response, e.g., have a protective effect against antigen-induced late responses and airway hyper-responsiveness ("AHR"), are considered to be active in this model.

Allergic sheep which are shown to develop both early and late bronchial responses to inhaled Ascaris suum antigen are used to study the airway effects of the candidate compounds.

Following topical anesthesia of the nasal passages with 2% lidocaine, a balloon catheter is advanced through one nostril into the lower esophagus. The animals are then intubated with a cuffed endotracheal tube through the other nostril with a flexible fiberoptic bronchoscope as a guide.

Pleural pressure is estimated according to Abraham (1994). Aerosols (see formulation below) are generated using a disposable medical nebulizer that provides an aerosol with a mass median aerodynamic diameter of 3.2 µm as determined with an Andersen cascade impactor. The nebulizer is connected to a dosimeter system consisting of a solenoid valve and a source of compressed air (20 psi). The output of the nebulizer is directed into a plastic T-piece, one end of which is connected to the inspiratory port of a piston respirator. The solenoid valve is activated for 1 second at the beginning of the inspiratory cycle of the respirator. Aerosols are delivered at VT of 500 ml and a rate of 20 breaths/minute. A 0.5% sodium bicarbonate solution only is used as a control.

To assess bronchial responsiveness, cumulative concentration-response curves to carbachol can be generated according to Abraham (1994). Bronchial biopsies can be taken prior to and following the initiation of treatment and 24 hours after antigen challenge. Bronchial biopsies can be preformed according to Abraham (1994).

An in vitro adhesion study of alveolar macrophages can also be performed according to Abraham (1994), and a percentage of adherent cells is calculated.

Aerosol Formulation

A solution of the candidate compound in 0.5% sodium bicarbonate/saline (w/v) at a concentration of 30.0 mg/mL is prepared using the following procedure:

A. Preparation of 0.5% Sodium Bicarbonate/Saline Stock Solution: 100.0 mL

| Ingredient | Gram/100.0 mL | Final Concentration |
|---|---|---|
| Sodium Bicarbonate | 0.5 g | 0.5% |
| Saline | q.s. ad 100.0 mL | q.s. ad 100% |

Procedure:
1. Add 0.5 g sodium bicarbonate into a 100 mL volumetric flask.
2. Add approximately 90.0 mL saline and sonicate until dissolved.
3. Q.S. to 100.0 mL with saline and mix thoroughly.

B. Preparation of 30.0 mg/mL Candidate Compound: 10.0 mL

| Ingredient | Gram/10.0 mL | Final Concentration |
|---|---|---|
| Candidate Compound | 0.300 g | 30.0 mg/mL |
| 0.5% Sodium Bicarbonate/Saline Stock Solution | q.s. ad 10.0 mL | q.s ad 100% |

Procedure:
1. Add 0.300 g of the candidate compound into a 10.0 mL volumetric flask.
2. Add approximately 9.7 mL of 0.5% sodium bicarbonate/saline stock solution.
3. Sonicate until the candidate compound is completely dissolved.
4. Q.S. to 10.0 mL with 0.5% sodium bicarbonate/saline stock solution and mix thoroughly.

Using a conventional oral formulation, compounds of this invention would be active in this model.

Example E

Allograft Model

Allograft rejection, associated with infiltration of inflammatory cells, is the leading obstacle to long-term allograft survival. Cell surface adhesion molecules facilitate alloantigen recognition in vitro and may be critical for lymphocyte traffic in vivo. The following describes a model which can be used to study the in vivo effects of the compounds of this invention in the control of allograft rejection.

The following procedures are described in Coito et al., Transplantation (1998) 65 (6):699-706 and in Korom et al., Transplantation (1998) 65 (6):854-859, both of which are incorporated by reference in their entirety.

Following the procedures described in Coito and Korom, male adult rats weighing approximately 200-250 g are used in this model. Lewis rats are used as the recipients of cardiac allografts from Lewis X Brown Norway rats. Hearts are transplanted into the abdominal great vessels using standard microvascular techniques. A candidate compound is administered to the transplant recipient in a suitable pharmaceutical carrier for a 7-day course of treatment starting the day of the engraftment. Doses range from 0.3 to 30 mg/kg/day. Control recipients receive the pharmaceutical carrier only. The rats are euthanized and their cardiac allografts are analyzed as described in Coito and Korom.

Using conventional formulations, compounds of this invention would be active in this model.

Example F

In vitro Saturation Assay for Determining Binding of Candidate Compounds to α4β1

The following describes an in vitro assay to determine the plasma levels needed for a compound to be active in the Experimental Autoimmune Encephalomyelitis ("EAE") model, described in the next example, or in other in vivo models.

Log-growth Jurkat cells are washed and resuspended in normal animal plasma containing 20 µg/ml of the 15/7 antibody (described in the above example).

The Jurkat cells are diluted two-fold into either normal plasma samples containing known candidate compound amounts in various concentrations ranging from 66 µM to 0.01 µM, using a standard 12 point serial dilution for a standard curve, or into plasma samples obtained from the peripheral blood of candidate compound-treated animals.

Cells are then incubated for 30 minutes at room temperature, washed twice with phosphate-buffered saline ("PBS") containing 2% fetal bovine serum and 1 mM each of calcium chloride and magnesium chloride (assay medium) to remove unbound 15/7 antibody.

The cells are then exposed to phycoerythrin-conjugated goat F(ab')$_2$ anti-mouse IgG Fc (Immunotech, Westbrook, Me.), which has been adsorbed for any non-specific cross-reactivity by co-incubation with 5% serum from the animal species being studied, at 1:200 and incubated in the dark at 4° C. for 30 minutes.

Cells are washed twice with assay medium and resuspended in the same. They are then analyzed with a standard fluorescence activated cell sorter ("FACS") analysis as described in Yednock et al. J. Biol. Chem., 1995, 270:28740.

The data is then graphed as fluorescence versus dose, e.g., in a normal dose-response fashion. By measuring the fluorescence generated by test samples at various dilutions against the standard curve, the concentration of a compound in the blood can be determined. Compound half life can be determined, as well as the frequency of dosing required to maintain levels in the upper plateau of the curve, which represents the levels needed to obtain efficacy in an in vivo model.

Example G

Adjuvant-Induced Arthritis in Rats

Adjuvant induced arthritis ("AIA") is an animal model useful in the study of rheumatoid arthritis (RA), which is induced by injecting *M. tuberculosis* in the base of the tail of Lewis rats. Between 10 and 15 days following injection, animals develop a severe, progressive arthritis.

Generally, compounds are tested for their ability to alter hind paw swelling and bone damage resulting from adjuvant-induced edema in rats. To quantitate the inhibition of hind paw swelling resulting from AIA, two phases of inflammation have been defined: (1) the primary and secondary injected hind paw, and (2) the secondary uninjected hind paw, which generally begins developing about eleven days from the induction of inflammation in the injected paw. Reduction of the latter type of inflammation is an indication of immunosuppressive activity. Cf. Chang, Arth. Rheum., 20, 1135-1141 (1977).

Using an animal model of RA, such as AIA, enables one to study the cellular events involved in the early stages of the disease. CD44 expression on macrophages and lymphocytes is up-regulated during the early development of adjuvant arthritis, whereas LFA-1 expression is up-regulated later in the development of the disease. Understanding the interactions between adhesion molecules and endothelium at the earliest stages of adjuvant arthritis could lead to significant advances in the methods used in the treatment of RA.

The invention has been described with reference to various specific and preferred embodiments and techniques. However, it should be understood that many variations and modifications may be made while remaining within the spirit and scope of the invention.

REFERENCES

The following publications, patents and patent applications, certain of which are cited in this application as superscript numbers, are herein incorporated by reference in their entirety to the same extent as if each individual publication, patent or patent application was specifically and individually indicated to be incorporated by reference in its entirety.

1 Hemler and Takada, European Patent Application Publication No. 330,506, published Aug. 30, 1989
2 Elices, et al., Cell, 60:577-584 (1990)
3 Springer, Nature, 346:425-434 (1990)
4 Osborn, Cell, 62:3-6 (1990)
5 Vedder, et al., Surgery, 106:509 (1989)
6 Pretolani, et al., J. Exp. Med., 180:795 (1994)
7 Abraham, et al., J. Clin. Invest., 93:776 (1994)
8 Mulligan, et al., J. Immunology, 150:2407 (1993)
9 Cybulsky, et al., Science, 251:788 (1991)
10 Li, et al., Arterioscler. Thromb., 13:197 (1993)
11 Sasseville, et al., Am. J. Path., 144:27 (1994)
12 Yang, et al., Proc. Nat. Acad. Science (USA), 90:10494 (1993)
13 Burkly, et al., Diabetes, 43:529 (1994)
14 Baron, et al., J. Clin. Invest., 93:1700 (1994)
15 Hamann, et al., J. Immunology, 152:3238 (1994)
16 Yednock, et al., Nature, 356:63 (1992)
17 Baron, et al., J. Exp. Med., 177:57 (1993)
18 van Dinther-Janssen, et al., J. Immunology, 147:4207 (1991)
19 van Dinther-Janssen, et al., Annals. Rheumatic Dis., 52:672 (1993)
20 Elices, et al., J. Clin. Invest., 93:405 (1994)
21 Postigo, et al., J. Clin. Invest., 89:1445 (1991)
22 Paul, et al., Transpl. Proceed., 25:813 (1993)
23 Okarhara, et al., Can. Res., 54:3233 (1994)
24 Paavonen, et al., Int. J. Can., 58:298 (1994)
25 Schadendorf, et al., J. Path., 170:429 (1993)
26 Bao, et al., Diff., 52:239 (1993)
27 Lauri, et al., British J. Cancer, 68:862 (1993)
28 Kawaguchi, et al., Japanese J. Cancer Res., 83:1304 (1992)
29 Kogan, et al., U.S. Pat. No. 5,510,332, issued Apr. 23, 1996
30 International Patent Appl. Publication No. WO 96/01644
31 Thorsett, et al., U.S. Pat. No. 6,489,300, issued Dec. 3, 2002 and Konradi, et al., U.S. Pat. No. 6,492,372, issued Dec. 10, 2002.

What is claimed is:
1. A compound of the formula:

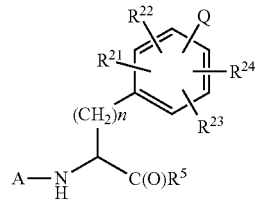

or a pharmaceutically acceptable salt thereof wherein
A is —H, optionally substituted aryl, optionally substituted heteroaryl or the group —C(X)D(R$^3$)Z, wherein D is a carbon atom (when part of a substituted aryl or substituted heteroaryl), CH, N or O, with the proviso that if D is oxygen, then Z is not present;
Z is —H, —NO$_2$, haloalkyl or the group —N(YR$^1$)R$^2$ wherein Y is a covalent bond, —C(O)— or —SO$_2$—, R$^1$ is R$^{1'}$, N(R$^{1'}$)$_2$, or —OR$^{1'}$ wherein each R$^{1'}$ is independently hydrogen, an optionally substituted straight or branched C$_1$-C$_6$alkyl, optionally substituted cycloalkyl, optionally substituted aryl, optionally substituted heterocyclic or an optionally substituted heteroaryl, wherein optional substitutions are halide, C$_1$-C$_6$alkyl, —OC$_1$-C$_6$alkyl and R$^2$ is hydrogen or R$^{1'}$;
X is selected from the group consisting of oxygen, sulfur, CHR$^4$ and NR$^4$, wherein R$^4$ is —H, alkyl or substituted alkyl;
R$^3$ is hydrogen, alkyl, substituted alkyl, cycloalkyl, substituted cycloalkyl, aryl, substituted aryl, heteroaryl, substituted heteroaryl, heterocyclic, or substituted heterocyclic; or
D, R$^3$ and Z together form a heterocyclic or a substituted heterocyclic group, wherein said group contains 1, 2, or 3 heteroatoms selected from O, N, and S; or X, D and R³ together with the carbon atom carrying D and X form an optionally substituted carbocyclic or optionally substituted heterocyclic group, wherein said heterocyclic group contains 1, 2, or 3 heteroatoms selected from O, N, and S;

R³ and R⁴ together with the nitrogen atom bound to R⁴ and the carbon atom bound to R³ form a heterocyclic or a substituted heterocyclic group, wherein said group contains 1, 2, or 3 heteroatoms selected from O, N, and S;

R⁵ is selected from the group consisting of amino, substituted amino, alkoxy, substituted alkoxy, cycloalkyloxy, substituted cycloalkyloxy, aryloxy and substituted aryloxy, and —OH;

n is 0 or an integer from 1 to 4;

Q is a group of the formula V1 or V2

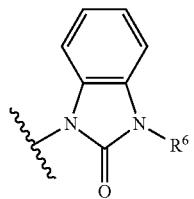

V1

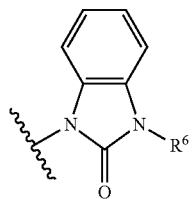

V2 wherein the pyrido portion of V1 and the benzo portion of V2 are each optionally substituted; and R⁶ is —H, alkyl, substituted alkyl, or —CH₂C(O)R⁷ wherein R⁷ is —OH, —OR⁸, or —NHR⁸ wherein R⁸ is alkyl, substituted alkyl, aryl or substituted aryl;

R²¹, R²², R²³, and R²⁴ are independently selected from the group consisting of hydrogen, —C₁-C₃alkyl, —OC₁-C₃alkyl and halogen.

2. A compound according to claim 1, wherein R² and R³ together with the nitrogen atom bound to R² and the carbon atom bound to R³ can form a heterocyclic or a substituted heterocyclic group, wherein said group contains 1, 2, or 3 heteroatoms selected from O, N, and S; or, R³ and R⁴ together with the nitrogen atom bound to R⁴ and the carbon atom bound to R³ can form a heterocyclic or a substituted heterocyclic group, wherein said group contains 1, 2, or 3 heteroatoms selected from O, N, and S.

3. A compound according to claim 1 where R⁶ is hydrogen or substituted alkyl.

4. A compound according to claim 3, where R⁶ is hydrogen or alkyl substituted with amino, aminocarbonyl, C₁-C₄ alkoxy(C₁-C₄)alkylaminocarbonyl, hydroxy(C₁-C₄)alkylaminocarbonyl, or aminoalkoxyalkoxyalkyl.

5. A compound according to claim 1, of the formula:

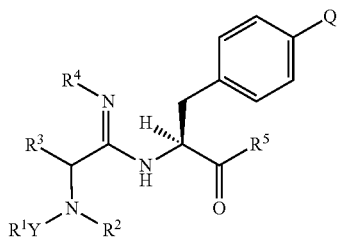

wherein

R³ and R⁴, together with the carbon atom and nitrogen atom to which they are bound respectively, are joined to form a heterocyclic group having at least five atoms in the heterocyclic group and optionally additionally containing 1 to 3 heteroatoms selected from the group consisting of oxygen, nitrogen and sulfur, and wherein the heterocyclic group is mono-cyclic; and where the heterocyclic group is optionally substituted, on any ring atom capable of substitution, with 1-3 substituents selected from the group consisting of alkyl, substituted alkyl, alkoxy, substituted alkoxy, acyl, acylamino, thiocarbonylamino, acyloxy, amino, substituted amino, amidino, alkyl amidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, cyano, halogen, hydroxyl, nitro, oxo, carboxyl, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkyloxy, substituted cycloalkyloxy, heteroaryloxy, substituted heteroaryloxy, heterocyclyloxy, substituted heterocyclyloxy, oxycarbonylamino, oxythiocarbonylamino, —OS(O)₂-alkyl, —OS(O)₂-substituted alkyl, —OS(O)₂-aryl, —OS(O)₂-substituted aryl, —OS(O)₂-heteroaryl, —OS(O)₂-substituted heteroaryl, —OS(O)₂-heterocyclic, —OS(O)₂-substituted heterocyclic, —OSO₂—NRR where each R is independently hydrogen or alkyl, —NRS(O)₂-alkyl, —NRS(O)₂-substituted alkyl, —NRS(O)₂-aryl, —NRS(O)₂-substituted aryl, —NRS(O)₂-heteroaryl, —NRS(O)₂-substituted heteroaryl, —NRS(O)₂-heterocyclic, —NRS(O)₂-substituted heterocyclic, —NRS(O)₂—NR-alkyl, —NRS(O)₂—NR-substituted alkyl, —NRS(O)₂—NR-aryl, —NRS(O)₂—NR-substituted aryl, —NRS(O)₂—NR-heteroaryl, —NRS(O)₂—NR-substituted heteroaryl, —NRS(O)₂—NR-heterocyclic, —NRS(O)₂—NR-substituted heterocyclic where R is hydrogen or alkyl, —N[S(O)—R']₂ and —N[S(O)₂—NR']₂ where each R' is independently selected from the group consisting of alkyl, substituted alkyl, aryl, substituted aryl, heteroaryl, substituted heteroaryl, heterocyclic and substituted heterocyclic.

6. A compound according to claim 1 of the formula:

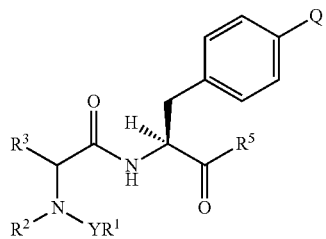

or a pharmaceutically acceptable salt thereof,
where $R^2$ and $R^3$, together with the nitrogen atom and carbon atom to which they are bound respectively, are joined to form a heterocyclic group having at least five atoms and optionally additionally containing 1 to 3 heteroatoms selected from the group consisting of oxygen, nitrogen and sulfur, and wherein the heterocyclic group is mono-cyclic; and
where the heterocyclic group is optionally substituted, on any ring atom capable of substitution, with 1-3 substituents selected from the group consisting of alkyl, substituted alkyl, alkoxy, substituted alkoxy, acyl, acylamino, thiocarbonylamino, acyloxy, amino, substituted amino, amidino, alkyl amidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, cyano, halogen, hydroxyl, nitro, oxo, carboxyl, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkyloxy, substituted cycloalkyloxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where each R is independently hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, —N[S(O)—R']$_2$ and —N[S(O)$_2$—NR']$_2$ where each R' is independently selected from the group consisting of alkyl, substituted alkyl, aryl, substituted aryl, heteroaryl, substituted heteroaryl, heterocyclic and substituted heterocyclic.

7. A compound according to claim 1 of the formula:

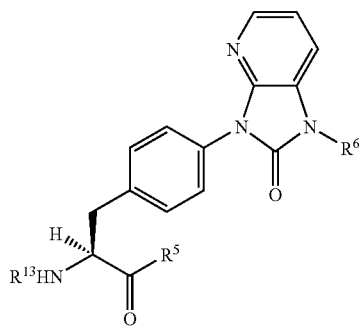

or a pharmaceutically acceptable salt thereof,
wherein $R^{13}$ is —H, or the group —C(O)OR$^{13'}$ wherein $R^{13'}$ is an optionally substituted alkyl, optionally substituted aryl or optionally substituted heteroaryl group.

8. A compound according to claim 1 of the formula

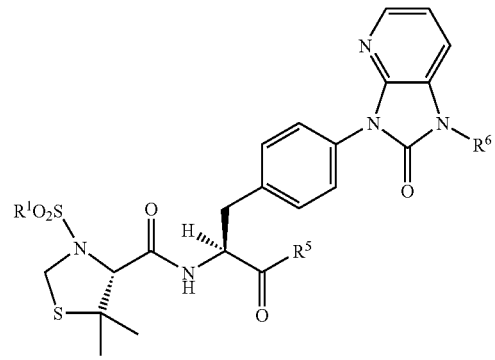

or a pharmaceutically acceptable salt thereof, wherein
$R^1$ is selected from the group consisting of straight or branched (C$_1$-C$_6$)alkyl, substituted straight or branched (C$_1$-C$_6$)alkyl, aryl, substituted aryl, cycloalkyl, substituted cycloalkyl, heterocyclic, substituted heterocyclic, heteroaryl and substituted heteroaryl.

9. A compound according to claim 8, where $R^6$ is hydrogen, alkyl or substituted alkyl.

10. A compound according to claim 8, where $R^6$ is hydrogen or alkyl substituted with hydroxy, halogen, amino, aminocarbonyl, C$_1$-C$_4$ alkoxy(C$_1$-C$_4$)alkylaminocarbonyl, hydroxy(C$_1$-C$_4$)alkylaminocarbonyl, or aminoalkoxyalkoxyalkyl.

11. A compound according to claim 8, where $R^1$ is phenyl or a 5- or 6-membered heteroaryl group having at least one nitrogen atom, and $R^1$ is optionally substituted with halogen, hydroxy, C$_1$-C$_6$ alkoxy, C$_1$-C$_6$ alkyl, nitro, trifluoromethyl, amino, mono- or di(C$_1$-C$_6$)alkylamino, amino(C$_1$-C$_6$)alkyl, C$_2$-C$_6$ acyl, C$_2$-C$_6$ acylamino, or amino(C$_1$-C$_6$)acyl.

12. A compound according to claim 8, where $R^1$ is pyridyl optionally substituted with amino(C$_1$-C$_6$)alkyl, C$_2$-C$_6$ acyl, C$_2$-C$_6$ acylamino, or amino(C$_1$-C$_6$)acyl.

13. A compound according to claim 8, wherein $R^1$ is pyridyl optionally substituted with C$_1$-C$_6$ alkyl, hydroxy, halogen, C$_1$-C$_6$ alkoxy, nitro, trifluoromethyl, amino, or mono- or di(C$_1$-C$_6$)alkylamino.

14. A compound according to claim 1, of the formula

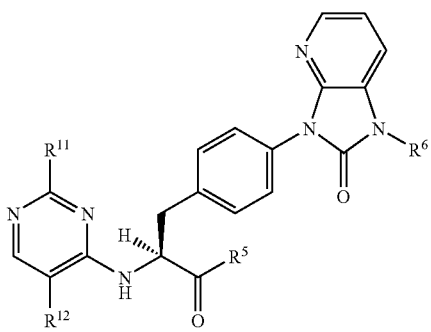

or a pharmaceutically acceptable salt thereof, wherein
$R^{11}$ is —H, —NH$_2$, (C$_1$-C$_6$)alkylamino or di(C$_1$-C$_6$)alkylamino; and
$R^{12}$ is —H, —NO$_2$, haloalkyl or —N(YR$^1$)R$^2$, where
Y is —C(O)— or —SO$_2$—,
R$^1$ is alkyl, substituted alkyl, aryl, substituted aryl, cycloalkyl, substituted cycloalkyl, heterocyclic, substituted heterocyclic, heteroaryl or substituted heteroaryl; and
R$^2$ is hydrogen, alkyl, cycloalkyl, substituted cycloalkyl, cycloalkenyl, substituted cycloalkenyl, heterocyclic, substituted heterocyclic, substituted alkyl, aryl, substituted aryl, heteroaryl, or substituted heteroaryl.

15. A compound according to claim 14, wherein R$^6$ is hydrogen or substituted alkyl.

16. A compound according to claim 15, where R$^6$ is hydrogen or alkyl substituted with amino, hydroxy, aminocarbonyl, C$_1$-C$_4$ alkoxy(C$_1$-C$_4$)alkylaminocarbonyl, hydroxy(C$_1$-C$_4$)alkylaminocarbonyl, or aminoalkoxyalkoxyalkyl.

17. A compound according to claim 14, where
R$^{11}$ is amino; —NHC$_1$-C$_3$alkyl or —NC$_1$-C$_3$dialkyl; and
R$^{12}$ is —H, —NO$_2$ or haloalkyl.

18. A compound according to claim 14, wherein
R$^{11}$ is amino, —NHC$_1$-C$_3$alkyl, or —NC$_1$-C$_3$dialkyl; and
R$^{12}$ is —N(YR$^1$)R$^2$; where
Y is —SO$_2$— or —CO—;
R$^1$ is
C$_1$-C$_6$ alkyl optionally substituted with halogen, hydroxy, C$_1$-C$_6$ alkoxy, amino, or mono- or di(C$_1$-C$_6$)alkylamino; or
phenyl or a 5- or 6-membered heteroaryl containing at least one nitrogen, and R$^1$ is optionally substituted with halogen, hydroxy, C$_1$-C$_6$ alkyl, C$_1$-C$_6$ alkoxy, C$_3$-C$_7$cycloalkyl, amino, nitro, trifluoromethyl, or mono- or di(C$_1$-C$_6$)alkylamino; and
R$^2$ is hydrogen, C$_1$-C$_6$alkyl, or C$_3$-C$_7$cycloalkyl.

19. A compound according to claim 14, wherein R$^{12}$ is —N(YR$^1$)R$^2$ wherein
R$^1$ is
C$_1$-C$_4$ alkyl optionally substituted with halogen, hydroxy, C$_1$-C$_6$ alkoxy, amino, or mono- or di(C$_1$-C$_6$)alkylamino; or
pyridyl or pyrimidinyl, each of which is optionally substituted with halogen, hydroxy, C$_1$-C$_3$ alkyl, C$_1$-C$_3$ alkoxy, amino, or mono- or di(C$_1$-C$_4$)alkylamino; and
R$^2$ is hydrogen, C$_1$-C$_4$alkyl, or C$_3$-C$_7$cycloalkyl.

20. A compound according to claim 1, which is selected from the group consisting of:
(S)-2-(2-(diethylamino)-5-(N-isopropylmethan-5-ylsulfonamido)pyrimidin-4-ylamino)-3-(4-(1-methyl-2-oxo-1,2-dihydroimidazo[4,5-b]pyridin-3-yl)phenyl)propanoic acid;

(S)-2-(2-(diethylamino)-5-(N-isopropylacetamido)pyrimidin-4-ylamino)-3-(4-(1-methyl-2-oxo-1,2-dihydroimidazo[4,5-b]pyridin-3-yl)phenyl)propanoic acid;
(S)-tert-butyl 2-(2-(diethylamino)-5-nitropyrimidin-4-ylamino)-3-(4-(1-methyl-2-oxo-1,2-dihydroimidazo[4,5-b]pyridin-3-yl)phenyl)propanoate;
(S)-2-((R)-5,5-dimethyl-3-(pyridin-3-ylsulfonyl)thiazolidine-4-carboxamido)-3-(4-(1-(2-(2-methoxyethylamino)-2-oxoethyl)-2-oxo-1,2-dihydroimidazo[4,5-b]pyridin-3-yl)phenyl)propanoic acid;
(S)-2-(2-(diethylamino)-5-(2,2,2-trifluoroethyl)pyrimidin-4-ylamino)-3-(4-(1-methyl-2-oxo-1,2-dihydroimidazo[4,5-b]pyridin-3-yl)phenyl)propanoic acid;
2-(3-(4-((S)-3-tert-butoxy-2-((R)-5,5-dimethyl-3-(pyridin-3-ylsulfonyl)thiazolidine-4-carboxamido)-3-oxopropyl)phenyl)-2-oxo-2,3-dihydroimidazo[4,5-b]pyridin-1-yl)acetic acid;
(S)-tert-butyl 2-((R)-5,5-dimethyl-3-(pyridin-3-ylsulfonyl)thiazolidine-4-carboxamido)-3-(4-(1-(2-(4-nitrophenoxy)-2-oxoethyl)-2-oxo-1,2-dihydroimidazo[4,5-b]pyridin-3-yl)phenyl)propanoate;
(S)-tert-butyl 2-((R)-5,5-dimethyl-3-(pyridin-3-ylsulfonyl)thiazolidine-4-carboxamido)-3-(4-(2-oxo-1,2-dihydroimidazo[4,5-b]pyridin-3-yl)phenyl)propanoate;
(S)-tert-butyl 2-amino-3-(4-(2-oxo-1,2-dihydroimidazo[4,5-b]pyridin-3-yl)phenyl)propanoate;
(S)-2-((R)-5,5-dimethyl-3-(pyridin-3-ylsulfonyl)thiazolidine-4-carboxamido)-3-(4-(2-oxo-1,2-dihydroimidazo[4,5-b]pyridin-3-yl)phenyl)propanoic acid;
(S)-2-(5-(N-ethylisonicotinamido)pyrimidin-4-ylamino)-3-(4-(2-oxo-1,2-dihydroimidazo[4,5-b]pyridin-3-yl)phenyl)propanoic acid;
(S)-3-(4-(1-(2-(2-(2-aminoethoxy)ethoxy)ethyl)-2-oxo-1,2-dihydroimidazo[4,5-b]pyridin-3-yl)phenyl)-2-((R)-5,5-dimethyl-3-(pyridin-3-ylsulfonyl)thiazolidine-4-carboxamido)propanoic acid;
(S)-tert-butyl 2-(benzyloxycarbonyl)-3-(4-(1-(2-methoxy-2-oxoethyl)-2-oxo-1,2-dihydroimidazo[4,5-b]pyridin-3-yl)phenyl)propanoate;
(S)-tert-butyl 2-amino-3-(4-(1-(2-methoxy-2-oxoethyl)-2-oxo-1H-imidazo[4,5-b]pyridin-3(2H)-yl)phenyl)propanoate;
(S)-tert-butyl 2-((R)-5,5-dimethyl-3-(pyridin-3-ylsulfonyl)thiazolidine-4-carboxamido)-3-(4-(1-(2-methoxy-2-oxoethyl)-2-oxo-1H-imidazo[4,5-b]pyridin-3(2H)-yl)phenyl)propanoate;
(S)-tert-butyl 2-(2-(diethylamino)-5-(2,2,2-trifluoroethyl)pyrimidin-4-ylamino)-3-(4-(2-oxo-1H-imidazo[4,5-b]pyridin-3(2H)-yl)phenyl)propanoate;
(S)-tert-butyl 2-(2-(diethylamino)-5-(2,2,2-trifluoroethyl)pyrimidin-4-ylamino)-3-(4-(1-methyl-2-oxo-1H-imidazo[4,5-b]pyridin-3(2H)-yl)phenyl)propanoate;
(S)-tert-butyl 2-(5-(N-ethylisonicotinamido)pyrimidin-4-ylamino)-3-(4-(2-oxo-1H-imidazo[4,5-b]pyridin-3(2H)-yl)phenyl)propanoate;
(S)-tert-butyl 2-(2-(diethylamino)-5-nitropyrimidin-4-ylamino)-3-(4-(2-oxo-1H-imidazo[4,5-b]pyridin-3(2H)-yl)phenyl)propanoate;
(S)-tert-butyl 2-(2-(diethylamino)-5-(isopropylamino)pyrimidin-4-ylamino)-3-(4-(1-methyl-2-oxo-1H-imidazo[4,5-b]pyridin-3(2H)-yl)phenyl)propanoate;
(S)-tert-butyl 2-(2-(diethylamino)-5-(N-isopropylmethylsulfonamido)pyrimidin-4-ylamino)-3-(4-(1-methyl-2-oxo-1H-imidazo[4,5-b]pyridin-3(2H)-yl)phenyl)propanoate; and (S)-2-(2-(diethylamino)-5-(N-ethylisonicotinamido)pyrimidin-4-ylamino)-3-(4-(2-oxo-1H-imidazo[4,5-b]pyridin-3(2H)-yl)phenyl)propanoic acid;
or pharmaceutically acceptable salts thereof.

21. A pharmaceutical composition comprising a pharmaceutically acceptable excipient and a compound according to claim 1.

22. A pharmaceutical composition comprising a compound according to claim 1 in combination with an $\alpha_4\beta_7$ inhibitor.

23. A method for treating a disease state selected from multiple sclerosis, asthma, and rheumatoid arthritis in a patient, which method comprises administering an effective amount of a compound according to claim 1 to the patient.

24. A method of claim 23 wherein the disease state is multiple sclerosis.

25. A method according to claim 23 wherein the disease state is asthma.

26. A method according to claim 23 wherein the disease state is rheumatoid arthritis.

27. A method for treating a disease state selected from multiple sclerosis, asthma, and rheumatoid arthritis in a patient, which method comprises co-administration of an effective amount of a compound according to claim 1 and an effective amount of an $\alpha_4\beta_7$ inhibitor.

* * * * *